US007807433B2

(12) United States Patent
Bylina et al.

(10) Patent No.: US 7,807,433 B2

(45) Date of Patent: Oct. 5, 2010

(54) GLYCOSIDASE ENZYMES

(75) Inventors: Edward J. Bylina, San Diego, CA (US); Ronald Swanson, Del Mar, CA (US); Eric Mathur, Carlsbad, CA (US); David E. Lam, Carlsbad, CA (US)

(73) Assignee: Verenium Corporation, San Diego, CA (US)

(*) Notice: Subject to any disclaimer, the term of this patent is extended or adjusted under 35 U.S.C. 154(b) by 87 days.

(21) Appl. No.: 11/866,279

(22) Filed: Oct. 2, 2007

(65) Prior Publication Data

US 2009/0142326 A1 Jun. 4, 2009

Related U.S. Application Data

(60) Division of application No. 09/134,078, filed on Aug. 13, 1998, now Pat. No. 6,368,844, which is a continuation of application No. 08/949,026, filed on Oct. 10, 1997, now abandoned.

(60) Provisional application No. 60/056,916, filed on Dec. 6, 1996.

(51) Int. Cl.

| | |
|---|---|
| ***C12N 9/24*** | (2006.01) |
| ***C12N 1/20*** | (2006.01) |
| ***C12N 15/00*** | (2006.01) |
| ***C12Q 1/00*** | (2006.01) |
| ***C12Q 1/68*** | (2006.01) |
| ***C12Q 1/34*** | (2006.01) |
| ***C12P 21/04*** | (2006.01) |
| ***C07H 21/04*** | (2006.01) |

(52) U.S. Cl. ............................... 435/200; 435/4; 435/6; 435/18; 435/440; 435/69.1; 435/71.1; 435/252.3; 435/320.1; 536/23.2

(58) Field of Classification Search ....................... None
See application file for complete search history.

(56) References Cited

OTHER PUBLICATIONS

Branden et al. Introduction to Protein Structure, Garland Publishing Inc., New York, p. 247, 1991.*

Yague et al. Nucleotide sequence and deletion analysis of the cellulase-encoding gene celH of Clostridium thermocellum. Gene. Apr. 30;89(1):61-7.*

* cited by examiner

*Primary Examiner*—Yong D Pak

(57) ABSTRACT

A thermostable glycosidase enzymes derived from various *Thermococcus, Staphylothermus* and *Pyrococcus* organisms is disclosed. The enzymes are produced from native or recombinant host cells and can be utilized in the food processing industry, pharmaceutical industry and in the textile industry, detergent industry and in the baking industry.

9 Claims, 46 Drawing Sheets

M11TL GLYCOSIDASE - 29G
COMPLETE GENE SEQUENCE - 9/95

```
TTG AAA TTC CCC AAA GAC TTC ATG ATA GGC TAC TCA TCT TCA CCG TTT      48
Leu Lys Phe Pro Lys Asp Phe Met Ile Gly Tyr Ser Ser Ser Pro Phe
  1               5                  10                  15

CAA TTT GAA GCT GGT ATT CCC GGG TCC GAG GAT CCG AAT AGT GAT TGG      96
Gln Phe Glu Ala Gly Ile Pro Gly Ser Glu Asp Pro Asn Ser Asp Trp
             20                  25                  30

TGG GTA TGG GTG CAT GAT CCG GAG AAC ACA GCA GCT GGA CTA GTC AGC     144
Trp Val Trp Val His Asp Pro Glu Asn Thr Ala Ala Gly Leu Val Ser
         35                  40                  45

GGC GAT TTT CCC GAG AAC GGC CCA GGT TAC TGG AAT TTA AAC CAA AAT     192
Gly Asp Phe Pro Glu Asn Gly Pro Gly Tyr Trp Asn Leu Asn Gln Asn
     50                  55                  60

GAC CAC GAC CTG GCT GAG AAG CTG GGG GTT AAC ACT ATT AGA GTA GGC     240
Asp His Asp Leu Ala Glu Lys Leu Gly Val Asn Thr Ile Arg Val Gly
 65                  70                  75                  80

GTT GAG TGG AGT AGG ATT TTT CCA AAG CCA ACT TTC AAT GTT AAA GTC     288
Val Glu Trp Ser Arg Ile Phe Pro Lys Pro Thr Phe Asn Val Lys Val
                 85                  90                  95

CCT GTA GAG AGA GAT GAG AAC GGC AGC ATT GTT CAC GTA GAT GTC GAT     336
Pro Val Glu Arg Asp Glu Asn Gly Ser Ile Val His Val Asp Val Asp
            100                 105                 110

GAT AAA GCG GTT GAA AGA CTT GAT GAA TTA GCC AAC AAG GAG GCC GTA     384
Asp Lys Ala Val Glu Arg Leu Asp Glu Leu Ala Asn Lys Glu Ala Val
        115                 120                 125

AAC CAT TAC GTA GAA ATG TAT AAA GAC TGG GTT GAA AGA GGT AGA AAA     432
Asn His Tyr Val Glu Met Tyr Lys Asp Trp Val Glu Arg Gly Arg Lys
    130                 135                 140

CTT ATA CTC AAT TTA TAC CAT TGG CCC CTG CCT CTC TGG CTT CAC AAC     480
Leu Ile Leu Asn Leu Tyr His Trp Pro Leu Pro Leu Trp Leu His Asn
145                 150                 155                 160

CCA ATC ATG GTG AGA AGA ATG GGC CCG GAC AGA GCG CCC TCA GGC TGG     528
Pro Ile Met Val Arg Arg Met Gly Pro Asp Arg Ala Pro Ser Gly Trp
                165                 170                 175

CTT AAC GAG GAG TCC GTG GTG GAG TTT GCC AAA TAC GCC GCA TAC ATT     576
Leu Asn Glu Glu Ser Val Val Glu Phe Ala Lys Tyr Ala Ala Tyr Ile
            180                 185                 190

GCT TGG AAA ATG GGC GAG CTA CCT GTT ATG TGG AGC ACC ATG AAC GAA     624
Ala Trp Lys Met Gly Glu Leu Pro Val Met Trp Ser Thr Met Asn Glu
        195                 200                 205

CCC AAC GTC GTT TAT GAG CAA GGA TAC ATG TTC GTT AAA GGG GGT TTC     672
Pro Asn Val Val Tyr Glu Gln Gly Tyr Met Phe Val Lys Gly Gly Phe
    210                 215                 220

CCA CCC GGC TAC TTG AGT TTG GAA GCT GCT GAT AAG GCC AGG AGA AAT     720
Pro Pro Gly Tyr Leu Ser Leu Glu Ala Ala Asp Lys Ala Arg Arg Asn
225                 230                 235                 240
```

FIG. 1a

```
ATG ATC CAG GCT CAT GCA CGG GCC TAT GAC AAT ATT AAA CGC TTC AGT     768
Met Ile Gln Ala His Ala Arg Ala Tyr Asp Asn Ile Lys Arg Phe Ser
                245                 250                 255

AAG AAA CCT GTT GGA CTA ATA TAC GCT TTC CAA TGG TTC GAA CTA TTA     816
Lys Lys Pro Val Gly Leu Ile Tyr Ala Phe Gln Trp Phe Glu Leu Leu
            260                 265                 270

GAG GGT CCA GCA GAA GTA TTT GAT AAG TTT AAG AGC TCT AAG TTA TAC     864
Glu Gly Pro Ala Glu Val Phe Asp Lys Phe Lys Ser Ser Lys Leu Tyr
        275                 280                 285

TAT TTC ACA GAC ATA GTA TCG AAG GGT AGT TCA ATC ATC AAT GTT GAA     912
Tyr Phe Thr Asp Ile Val Ser Lys Gly Ser Ser Ile Ile Asn Val Glu
    290                 295                 300

TAC AGG AGA GAT CTT GCC AAT AGG CTA GAC TGG TTG GGC GTT AAC TAC     960
Tyr Arg Arg Asp Leu Ala Asn Arg Leu Asp Trp Leu Gly Val Asn Tyr
305                 310                 315                 320

TAT AGC CGT TTA GTC TAC AAA ATC GTC GAT GAC AAA CCT ATA ATC CTG    1008
Tyr Ser Arg Leu Val Tyr Lys Ile Val Asp Asp Lys Pro Ile Ile Leu
                325                 330                 335

CAC GGG TAT GGA TTC CTT TGT ACA CCT GGG GGG ATC AGC CCG GCT GAA    1056
His Gly Tyr Gly Phe Leu Cys Thr Pro Gly Gly Ile Ser Pro Ala Glu
            340                 345                 350

AAT CCT TGT AGC GAT TTT GGG TGG GAG GTG TAT CCT GAA GGA CTC TAC    1104
Asn Pro Cys Ser Asp Phe Gly Trp Glu Val Tyr Pro Glu Gly Leu Tyr
        355                 360                 365

CTA CTT CTA AAA GAA CTT TAC AAC CGA TAC GGG GTA GAC TTG ATC GTG    1152
Leu Leu Leu Lys Glu Leu Tyr Asn Arg Tyr Gly Val Asp Leu Ile Val
    370                 375                 380

ACC GAG AAC GGT GTT TCA GAC AGC AGG GAT GCG TTG AGA CCG GCA TAC    1200
Thr Glu Asn Gly Val Ser Asp Ser Arg Asp Ala Leu Arg Pro Ala Tyr
385                 390                 395                 400

CTG GTC TCG CAT GTT TAC AGC GTA TGG AAA GCC GCT AAC GAG GGC ATT    1248
Leu Val Ser His Val Tyr Ser Val Trp Lys Ala Ala Asn Glu Gly Ile
                405                 410                 415

CCC GTC AAA GGC TAC CTC CAC TGG AGC TTG ACA GAC AAT TAC GAG TGG    1296
Pro Val Lys Gly Tyr Leu His Trp Ser Leu Thr Asp Asn Tyr Glu Trp
            420                 425                 430

GCC CAG GGC TTC AGG CAG AAA TTC GGT TTA GTC ATG GTT GAC TTC AAA    1344
Ala Gln Gly Phe Arg Gln Lys Phe Gly Leu Val Met Val Asp Phe Lys
        435                 440                 445

ACT AAG AAA AGG TAT CTC CGC CCA AGC GCC CTA GTG TTC CGG GAG ATC    1392
Thr Lys Lys Arg Tyr Leu Arg Pro Ser Ala Leu Val Phe Arg Glu Ile
    450                 455                 460

GCA ACG CAT AAC GGA ATA CCG GAT GAG CTA CAG CAT CTT ACA CTG ATC    1440
Ala Thr His Asn Gly Ile Pro Asp Glu Leu Gln His Leu Thr Leu Ile
465                 470                 475                 480

CAG TAA                                                            1446
Gln
```

FIG. 1b

OC1/4 GLYCOSIDASE - 33G/B
COMPLETE GENE SEQUENCE - 9/95

```
ATG ATA AGA AGG TCC GAT TTT CCA AAA GAT TTT ATC TTC GGA ACG GCT     48
Met Ile Arg Arg Ser Asp Phe Pro Lys Asp Phe Ile Phe Gly Thr Ala
  1               5                  10                  15

ACG GCA GCA TAC CAG ATT GAA GGT GCA GCA AAC GAA GAT GGC AGA GGG     96
Thr Ala Ala Tyr Gln Ile Glu Gly Ala Ala Asn Glu Asp Gly Arg Gly
             20                  25                  30

CCA TCA ATT TGG GAT GTC TTT TCA CAC ACG CCT GGC AAA ACC CTG AAC    144
Pro Ser Ile Trp Asp Val Phe Ser His Thr Pro Gly Lys Thr Leu Asn
         35                  40                  45

GGT GAC ACA GGA GAC GTT GCG TGT GAC CAT TAT CAC CGA TAC AAG GAA    192
Gly Asp Thr Gly Asp Val Ala Cys Asp His Tyr His Arg Tyr Lys Glu
     50                  55                  60

GAT ATC CAG CTG ATG AAA GAA ATA GGG TTA GAC GCT TAC AGG TTC TCT    240
Asp Ile Gln Leu Met Lys Glu Ile Gly Leu Asp Ala Tyr Arg Phe Ser
 65                  70                  75                  80

ATC TCC TGG CCC AGA ATT ATG CCA GAT GGG AAG AAC ATC AAC CAA AAG    288
Ile Ser Trp Pro Arg Ile Met Pro Asp Gly Lys Asn Ile Asn Gln Lys
                 85                  90                  95

GGT GTG GAT TTC TAC AAC AGA CTC GTT GAT GAG CTT TTG AAG AAT GAT    336
Gly Val Asp Phe Tyr Asn Arg Leu Val Asp Glu Leu Leu Lys Asn Asp
            100                 105                 110

ATC ATA CCA TTC GTA ACA CTC TAT CAC TGG GAC TTA CCC TAC GCA CTT    384
Ile Ile Pro Phe Val Thr Leu Tyr His Trp Asp Leu Pro Tyr Ala Leu
        115                 120                 125

TAT GAA AAA GGT GGA TGG CTT AAC CCA GAT ATA GCG CTC TAT TTC AGA    432
Tyr Glu Lys Gly Gly Trp Leu Asn Pro Asp Ile Ala Leu Tyr Phe Arg
    130                 135                 140

GCA TAC GCA ACG TTT ATG TTC AAC GAA CTC GGT GAT CGT GTG AAA CAT    480
Ala Tyr Ala Thr Phe Met Phe Asn Glu Leu Gly Asp Arg Val Lys His
145                 150                 155                 160

TGG ATT ACA CTG AAC GAA CCA TGG TGT TCT TCT TTC TCG GGT TAT TAC    528
Trp Ile Thr Leu Asn Glu Pro Trp Cys Ser Ser Phe Ser Gly Tyr Tyr
                165                 170                 175

ACG GGA GAG CAT GCC CCG GGT CAT CAA AAT TTA CAA GAA GCG ATA ATC    576
Thr Gly Glu His Ala Pro Gly His Gln Asn Leu Gln Glu Ala Ile Ile
            180                 185                 190

GCG GCG CAC AAC CTG TTG AGG GAA CAT GGA CAT GCC GTC CAG GCG TCC    624
Ala Ala His Asn Leu Leu Arg Glu His Gly His Ala Val Gln Ala Ser
        195                 200                 205

AGA GAA GAA GTA AAA GAT GGG GAA GTT GGC TTA ACC AAC GTT GTG ATG    672
Arg Glu Glu Val Lys Asp Gly Glu Val Gly Leu Thr Asn Val Val Met
    210                 215                 220
```

FIG. 2a

```
AAA ATA GAA CCG GGC GAT GCA AAA CCC GAA AGT TTC TTG GTC GCA AGT    720
Lys Ile Glu Pro Gly Asp Ala Lys Pro Glu Ser Phe Leu Val Ala Ser
225                 230                 235                 240

CTT GTT GAT AAG TTC GTT AAT GCA TGG TCC CAT GAC CCT GTT GTT TTC    768
Leu Val Asp Lys Phe Val Asn Ala Trp Ser His Asp Pro Val Val Phe
                245                 250                 255

GGA AAA TAT CCC GAA GAA GCA GTT GCA CTT TAT ACG GAA AAA GGG TTG    816
Gly Lys Tyr Pro Glu Glu Ala Val Ala Leu Tyr Thr Glu Lys Gly Leu
            260                 265                 270

CAA GTT CTC GAT AGC GAT ATG AAT ATT ATT TCG ACT CCT ATA GAC TTC    864
Gln Val Leu Asp Ser Asp Met Asn Ile Ile Ser Thr Pro Ile Asp Phe
        275                 280                 285

TTT GGT GTG AAT TAT TAC ACA AGA ACA CTT GTT GTT TTT GAT ATG AAC    912
Phe Gly Val Asn Tyr Tyr Thr Arg Thr Leu Val Val Phe Asp Met Asn
    290                 295                 300

AAT CCT CTT GGA TTT TCG TAT GTT CAG GGA GAC CTT CCC AAA ACG GAG    960
Asn Pro Leu Gly Phe Ser Tyr Val Gln Gly Asp Leu Pro Lys Thr Glu
305                 310                 315                 320

ATG GGA TGG GAA ATC TAC CCG CAG GGA TTA TTT GAT ATG CTG GTC TAT   1008
Met Gly Trp Glu Ile Tyr Pro Gln Gly Leu Phe Asp Met Leu Val Tyr
                325                 330                 335

CTG AAG GAA AGA TAT AAA CTA CCA CTT TAT ATC ACA GAG AAC GGG ATG   1056
Leu Lys Glu Arg Tyr Lys Leu Pro Leu Tyr Ile Thr Glu Asn Gly Met
            340                 345                 350

GCT GGA CCT GAT AAA TTG GAA AAC GGA AGA GTT CAT GAT AAT TAC CGA   1104
Ala Gly Pro Asp Lys Leu Glu Asn Gly Arg Val His Asp Asn Tyr Arg
        355                 360                 365

ATT GAA TAT TTG GAA AAG CAC TTT GAA AAA GCA CTT GAA GCA ATC AAT   1152
Ile Glu Tyr Leu Glu Lys His Phe Glu Lys Ala Leu Glu Ala Ile Asn
    370                 375                 380

GCA GAT GTT GAT TTG AAA GGT TAC TTC ATT TGG TCT TTG ATG GAT AAC   1200
Ala Asp Val Asp Leu Lys Gly Tyr Phe Ile Trp Ser Leu Met Asp Asn
385                 390                 395                 400

TTC GAA TGG GCG TGC GGA TAC TCC AAA CGT TTC GGT ATA ATC TAC GTA   1248
Phe Glu Trp Ala Cys Gly Tyr Ser Lys Arg Phe Gly Ile Ile Tyr Val
                405                 410                 415

GAT TAC AAT ACC CCA AAA AGG ATA TTG AAA GAT TCA GCG ATG TGG TTG   1296
Asp Tyr Asn Thr Pro Lys Arg Ile Leu Lys Asp Ser Ala Met Trp Leu
            420                 425                 430

AAG GAA TTT CTA AAA TCT TAA                                       1317
Lys Glu Phe Leu Lys Ser
        43
```

FIG. 2b

STAPHYLOTHERMUS MARINUS GLYCOSIDASE - 12G
COMPLETE GENE SEQUENCE 9/95

```
TTG ATA AGG TTT CCT GAT TAT TTC TTG TTT GGA ACA GCT ACA TCA TCG      48
Leu Ile Arg Phe Pro Asp Tyr Phe Leu Phe Gly Thr Ala Thr Ser Ser
  1               5                  10                  15

CAC CAG ATC GAG GGT AAT AAC ATA TTT AAT GAT TGG TGG GAG TGG GAG      96
His Gln Ile Glu Gly Asn Asn Ile Phe Asn Asp Trp Trp Glu Trp Glu
 20                  25                  30

ACT AAA GGC AGG ATT AAG GTG AGA TCG GGT AAG GCA TGT AAT CAT TGG     144
Thr Lys Gly Arg Ile Lys Val Arg Ser Gly Lys Ala Cys Asn His Trp
         35                  40                  45

GAA CTC TAT AAA GAA GAC ATA GAG CTT ATG GCT GAG CTG GGA TAT AAT     192
Glu Leu Tyr Lys Glu Asp Ile Glu Leu Met Ala Glu Leu Gly Tyr Asn
     50                  55                  60

GCT TAT AGG TTC TCC ATA GAG TGG AGT AGA ATA TTT CCC AGA AAA GAT     240
Ala Tyr Arg Phe Ser Ile Glu Trp Ser Arg Ile Phe Pro Arg Lys Asp
 65                  70                  75                  80

CAT ATA GAT TAT GAG TCG CTT AAT AAG TAT AAG GAA ATA GTT AAT CTA     288
His Ile Asp Tyr Glu Ser Leu Asn Lys Tyr Lys Glu Ile Val Asn Leu
                 85                  90                  95

CTT AGA AAA TAC GGG ATA GAA CCT GTA ATC ACT CTT CAC CAC TTC ACA     336
Leu Arg Lys Tyr Gly Ile Glu Pro Val Ile Thr Leu His His Phe Thr
            100                 105                 110

AAC CCG CAA TGG TTT ATG AAA ATT GGT GGA TGG ACT AGG GAA GAG AAC     384
Asn Pro Gln Trp Phe Met Lys Ile Gly Gly Trp Thr Arg Glu Glu Asn
        115                 120                 125

ATA AAA TAT TTT ATA AAA TAT GTA GAA CTT ATA GCT TCC GAG ATA AAA     432
Ile Lys Tyr Phe Ile Lys Tyr Val Glu Leu Ile Ala Ser Glu Ile Lys
    130                 135                 140

GAC GTG AAA ATA TGG ATC ACT ATT AAT GAA CCA ATA ATA TAT GTT TTA     480
Asp Val Lys Ile Trp Ile Thr Ile Asn Glu Pro Ile Ile Tyr Val Leu
145                 150                 155                 160

CAA GGA TAT ATT TCC GGC GAA TGG CCA CCT GGA ATT AAA AAT TTA AAA     528
Gln Gly Tyr Ile Ser Gly Glu Trp Pro Pro Gly Ile Lys Asn Leu Lys
                165                 170                 175

ATA GCT GAT CAA GTA ACT AAG AAT CTT TTA AAA GCA CAT AAT GAA GCC     576
Ile Ala Asp Gln Val Thr Lys Asn Leu Leu Lys Ala His Asn Glu Ala
            180                 185                 190

TAT AAT ATA CTT CAT AAA CAC GGT ATT GTA GGC ATA GCT AAA AAC ATG     624
Tyr Asn Ile Leu His Lys His Gly Ile Val Gly Ile Ala Lys Asn Met
        195                 200                 205

ATA GCA TTT AAA CCA GGA TCT AAT AGA GGA AAA GAC ATT AAT ATT TAT     672
Ile Ala Phe Lys Pro Gly Ser Asn Arg Gly Lys Asp Ile Asn Ile Tyr
    210                 215                 220
```

FIG. 3a

```
CAT AAA GTC GAT AAA GCA TTC AAC TGG GGA TTT CTC AAC GGA ATA TTA      720
His Lys Val Asp Lys Ala Phe Asn Trp Gly Phe Leu Asn Gly Ile Leu
225                 230                 235                 240

AGG GGA GAA CTA GAA ACT CTC CGT GGA AAA TAC CGA GTT GAG CCC GGA      768
Arg Gly Glu Leu Glu Thr Leu Arg Gly Lys Tyr Arg Val Glu Pro Gly
                245                 250                 255

AAT ATT GAT TTC ATA GGC ATA AAC TAT TAT TCA TCA TAT ATT GTA AAA      816
Asn Ile Asp Phe Ile Gly Ile Asn Tyr Tyr Ser Ser Tyr Ile Val Lys
            260                 265                 270

TAT ACT TGG AAT CCT TTT AAA CTA CAT ATT AAA GTC GAA CCA TTA GAT      864
Tyr Thr Trp Asn Pro Phe Lys Leu His Ile Lys Val Glu Pro Leu Asp
        275                 280                 285

ACA GGT CTA TGG ACA ACT ATG GGT TAC TGC ATA TAT CCT AGA GGA ATA      912
Thr Gly Leu Trp Thr Thr Met Gly Tyr Cys Ile Tyr Pro Arg Gly Ile
    290                 295                 300

TAT GAA GTT GTA ATG AAA ACT CAT GAG AAA TAC GGC AAA GAA ATA ATC      960
Tyr Glu Val Val Met Lys Thr His Glu Lys Tyr Gly Lys Glu Ile Ile
305                 310                 315                 320

ATT ACA GAG AAC GGT GTT GCA GTA GAA AAT GAT GAA TTA AGG ATT TTA     1008
Ile Thr Glu Asn Gly Val Ala Val Glu Asn Asp Glu Leu Arg Ile Leu
                325                 330                 335

TCC ATT ATC AGG CAC TTA CAA TAC TTA TAT AAA GCC ATG AAT GAA GGA     1056
Ser Ile Ile Arg His Leu Gln Tyr Leu Tyr Lys Ala Met Asn Glu Gly
            340                 345                 350

GCA AAG GTG AAA GGA TAT TTC TAC TGG AGC TTC ATG GAT AAT TTT GAG     1104
Ala Lys Val Lys Gly Tyr Phe Tyr Trp Ser Phe Met Asp Asn Phe Glu
        355                 360                 365

TGG GAT AAA GGA TTT AAC CAA AGG TTC GGA CTA GTA GAA GTT GAT TAT     1152
Trp Asp Lys Gly Phe Asn Gln Arg Phe Gly Leu Val Glu Val Asp Tyr
    370                 375                 380

AAG ACT TTT GAG AGA AAA CCT AGA AAA AGC GCA TAT GTA TAT AGT CAA     1200
Lys Thr Phe Glu Arg Lys Pro Arg Lys Ser Ala Tyr Val Tyr Ser Gln
385                 390                 395                 400

ATA GCA CGT ACC AAG ACT ATA AGT GAT GAA TAC CTA GAA AAA TAT GGA     1248
Ile Ala Arg Thr Lys Thr Ile Ser Asp Glu Tyr Leu Glu Lys Tyr Gly
                405                 410                 415

TTA AAG AAC CTC GAA TAA                                             1266
Leu Lys Asn Leu Glu
            420
```

FIG. 3b

THERMOCOCCUS 9N2 GLYCOSIDASE - 31B/G
COMPLETE GENE SEQUENCE 9/95

```
ATG CTA CCA GAA GGC TTT CTC TGG GGC GTG TCC CAG TCC GGC TTT CAG      48
Met Leu Pro Glu Gly Phe Leu Trp Gly Val Ser Gln Ser Gly Phe Gln
  1               5                  10                  15

TTC GAG ATG GGC GAC AAG CTC AGG AGG AAC ATT GAT CCG AAC ACA GAC      96
Phe Glu Met Gly Asp Lys Leu Arg Arg Asn Ile Asp Pro Asn Thr Asp
             20                  25                  30

TGG TGG AAG TGG GTC AGG GAT CCC TTC AAC ATA AAG AGG GAA CTC GTC     144
Trp Trp Lys Trp Val Arg Asp Pro Phe Asn Ile Lys Arg Glu Leu Val
         35                  40                  45

AGC GGC GAC CTG CCC GAG GAG GGG ATA AAC AAC TAC GAA CTT TAC GAG     192
Ser Gly Asp Leu Pro Glu Glu Gly Ile Asn Asn Tyr Glu Leu Tyr Glu
     50                  55                  60

AAG GAT CAC CGC CTC GCC AGA GAC CTC GGT CTG AAC GTT TAC AGG ATT     240
Lys Asp His Arg Leu Ala Arg Asp Leu Gly Leu Asn Val Tyr Arg Ile
 65                  70                  75                  80

GGA ATA GAG TGG AGC AGG ATC TTT CCC TGG CCA ACG TGG TTT GTG GAG     288
Gly Ile Glu Trp Ser Arg Ile Phe Pro Trp Pro Thr Trp Phe Val Glu
                 85                  90                  95

GTT GAC GTT GAG CGG GAC AGC TAC GGA CTC GTG AAG GAC GTC AAA ATC     336
Val Asp Val Glu Arg Asp Ser Tyr Gly Leu Val Lys Asp Val Lys Ile
            100                 105                 110

GAT AAA GAC ACG CTC GAA GAG CTC GAC GAG ATA GCG AAT CAT CAG GAG     384
Asp Lys Asp Thr Leu Glu Glu Leu Asp Glu Ile Ala Asn His Gln Glu
        115                 120                 125

ATA GCC TAC TAC CGC CGC GTT ATA GAG CAC CTC AGG GAG CTG GGC TTC     432
Ile Ala Tyr Tyr Arg Arg Val Ile Glu His Leu Arg Glu Leu Gly Phe
    130                 135                 140

AAG GTC ATC GTG AAC CTC AAC CAC TTC ACG CTC CCC CTC TGG CTT CAC     480
Lys Val Ile Val Asn Leu Asn His Phe Thr Leu Pro Leu Trp Leu His
145                 150                 155                 160

GAT CCG ATA ATC GCG AGG GAG AAG GCC CTC ACC AAC GGT AGG ATT GGC     528
Asp Pro Ile Ile Ala Arg Glu Lys Ala Leu Thr Asn Gly Arg Ile Gly
                165                 170                 175

TGG GTC GGG CAG GAG AGC GTG GTG GAG TTC GCC AAG TAC GCG GCG TAC     576
Trp Val Gly Gln Glu Ser Val Val Glu Phe Ala Lys Tyr Ala Ala Tyr
            180                 185                 190

ATC GCG AAC GCA CTC GGG GAC CTC GTT GAT ATG TGG AGC ACC TTC AAC     624
Ile Ala Asn Ala Leu Gly Asp Leu Val Asp Met Trp Ser Thr Phe Asn
        195                 200                 205

GAG CCG ATG GTC GTT GTG GAG CTC GGT TAC CTC GCG CCC TAC TCC GGC     672
Glu Pro Met Val Val Val Glu Leu Gly Tyr Leu Ala Pro Tyr Ser Gly
    210                 215                 220

TTT CCG CCG GGG GTT ATG AAC CCC GAG GCG GCA AAG CTG GCA ATC CTC     720
Phe Pro Pro Gly Val Met Asn Pro Glu Ala Ala Lys Leu Ala Ile Leu
225                 230                 235                 240

AAC ATG ATA AAC GCC CAC GCA CTG GCC TAC AAG ATG ATA AAG AAG TTC     768
Asn Met Ile Asn Ala His Ala Leu Ala Tyr Lys Met Ile Lys Lys Phe
                245                 250                 255
```

FIG. 4a

```
GAC AGG GTA AAG GCC GAT AAG GAT TCC CGC TCC GAG GCC GAG GTC GGG      816
Asp Arg Val Lys Ala Asp Lys Asp Ser Arg Ser Glu Ala Glu Val Gly
            260                 265                 270

ATA ATC TAC AAC AAC ATA GGC GTT GCC TAT CCA TAC GAC TCC AAC GAC      864
Ile Ile Tyr Asn Asn Ile Gly Val Ala Tyr Pro Tyr Asp Ser Asn Asp
        275                 280                 285

CCA AAG GAC GTG AAA GCT GCA GAA AAC GAC AAC TAC TTC CAC AGC GGG      912
Pro Lys Asp Val Lys Ala Ala Glu Asn Asp Asn Tyr Phe His Ser Gly
295                 300

CTC TTC TTC GAC GCA ATC CAC AAG GGC AAG CTC AAC ATC GAG TTC GAC      960
Leu Phe Phe Asp Ala Ile His Lys Gly Lys Leu Asn Ile Glu Phe Asp
305                 310                 315                 320

GGT GAG ACC TTC GTC AAA GTT CGG CAT CTC AGG GGG AAC GAC TGG ATA     1008
Gly Glu Thr Phe Val Lys Val Arg His Leu Arg Gly Asn Asp Trp Ile
                325                 330                 335

GGC GTT AAC TAC TAC ACG AGA GAA GTC GTC AGG TAT TCG GAG CCC AAG     1056
Gly Val Asn Tyr Tyr Thr Arg Glu Val Val Arg Tyr Ser Glu Pro Lys
            340                 345                 350

TTC CCG AGC ATA CCC CTG ATA TCC TTC CGG GGA GTT CAC AAC TAC GGC     1104
Phe Pro Ser Ile Pro Leu Ile Ser Phe Arg Gly Val His Asn Tyr Gly
        355                 360                 365

TAC GCC TGC AGG CCC GGG AGT TCT TCC GCC GAC GGA AGG CCC GTA AGC     1152
Tyr Ala Cys Arg Pro Gly Ser Ser Ser Ala Asp Gly Arg Pro Val Ser
    370                 375                 380

GAC ATC GGC TGG GAG ATC TAT CCG GAG GGG ATC TAC GAC TCG ATA AGA     1200
Asp Ile Gly Trp Glu Ile Tyr Pro Glu Gly Ile Tyr Asp Ser Ile Arg
385                 390                 395                 400

GAG GCC AAC AAA TAC GGG GTC CCG GTT TAC GTC ACC GAA AAC GGA ATA     1248
Glu Ala Asn Lys Tyr Gly Val Pro Val Tyr Val Thr Glu Asn Gly Ile
                405                 410                 415

GCC GAT TCA ACT GAC ACC CTG CGG CCG TAC TAC CTC GCG AGC CAT GTA     1296
Ala Asp Ser Thr Asp Thr Leu Arg Pro Tyr Tyr Leu Ala Ser His Val
            420                 425                 430

GCG AAG ATT GAG GAG GCG TAC GAG GCG GGT TAC GAC GTC AGG GGC TAC     1344
Ala Lys Ile Glu Glu Ala Tyr Glu Ala Gly Tyr Asp Val Arg Gly Tyr
        435                 440                 445

CTC TAC TGG GCG CTG ACC GAC AAC TAC GAG TGG GCC CTC GGT TTC AGG     1392
Leu Tyr Trp Ala Leu Thr Asp Asn Tyr Glu Trp Ala Leu Gly Phe Arg
    450                 455                 460

ATG AGG TTC GGC CTC TAT AAA GTG GAT CTC ATA ACC AAG GAG AGA ACA     1440
Met Arg Phe Gly Leu Tyr Lys Val Asp Leu Ile Thr Lys Glu Arg Thr
465                 470                 475                 480

CCG CGG GAG GAA AGC GTA AAG GTT TAT AGG GGC ATC GTG GAG AAC AAC     1488
Pro Arg Glu Glu Ser Val Lys Val Tyr Arg Gly Ile Val Glu Asn Asn
                485                 490                 495

GGA GTG AGC AAG GAA ATC CGG GAG AAG TTC GGA CTT GGG TGA             1530
Gly Val Ser Lys Glu Ile Arg Glu Lys Phe Gly Leu Gly
             500                 505
```

FIG. 4b

```
ATG GAA AGG ATC GAT GAA ATT CTC TCT CAG TTA ACT ACA GAG GAA AAG      48
Met Glu Arg Ile Asp Glu Ile Leu Ser Gln Leu Thr Thr Glu Glu Lys
 1               5                  10                  15

GTG AAG CTC GTT GTG GGG GTT GGT CTT CCA GGA CTT TTT GGG AAC CCA      96
Val Lys Leu Val Val Gly Val Gly Leu Pro Gly Leu Phe Gly Asn Pro
            20                  25                  30

CAT TCC AGA GTG GCG GGT GCG GCT GGA GAA ACA CAT CCC GTT CCA AGA     144
His Ser Arg Val Ala Gly Ala Ala Gly Glu Thr His Pro Val Pro Arg
        35                  40                  45

CTT GGA ATT CCT GCG TTT GTC CTG GCA GAT GGT CCC GCA GGA CTC AGA     192
Leu Gly Ile Pro Ala Phe Val Leu Ala Asp Gly Pro Ala Gly Leu Arg
    50                  55                  60

ATA AAT CCC ACA AGG GAA AAC GAT GAA AAC ACT TAC TAC ACG ACG GCA     240
Ile Asn Pro Thr Arg Glu Asn Asp Glu Asn Thr Tyr Tyr Thr Thr Ala
65                  70                  75                  80

TTT CCC GTT GAA ATC ATG CTC GCT TCT ACC TGG AAC AGA GAC CTT CTG     288
Phe Pro Val Glu Ile Met Leu Ala Ser Thr Trp Asn Arg Asp Leu Leu
                85                  90                  95

GAA GAA GTG GGA AAA GCC ATG GGA GAA GAA GTT AGG GAA TAC GGT GTC     336
Glu Glu Val Gly Lys Ala Met Gly Glu Glu Val Arg Glu Tyr Gly Val
            100                 105                 110

GAT GTG CTT CTT GCA CCT GCG ATG AAC ATT CAC AGA AAC CCT CTT TGT     384
Asp Val Leu Leu Ala Pro Ala Met Asn Ile His Arg Asn Pro Leu Cys
        115                 120                 125

GGA AGG AAT TTC GAG TAC TAC TCA GAA GAT CCT GTC CTT TCC GGT GAA     432
Gly Arg Asn Phe Glu Tyr Tyr Ser Glu Asp Pro Val Leu Ser Gly Glu
    130                 135                 140

ATG GCT TCA GCC TTT GTC AAG GGA GTT CAA TCT CAA GGG GTG GGA GCC     480
Met Ala Ser Ala Phe Val Lys Gly Val Gln Ser Gln Gly Val Gly Ala
145                 150                 155                 160

TGC ATA AAA CAC TTT GTC GCG AAC AAC CAG GAA ACG AAC AGG ATG GTA     528
Cys Ile Lys His Phe Val Ala Asn Asn Gln Glu Thr Asn Arg Met Val
                165                 170                 175

GTG GAC ACG ATC GTG TCC GAG CGA GCC CTC AGA GAA ATA TAT CTG AAA     576
Val Asp Thr Ile Val Ser Glu Arg Ala Leu Arg Glu Ile Tyr Leu Lys
            180                 185                 190

GGT TTT GAA ATT GCT GTC AAG AAA GCA AGA CCC TGG ACC GTG ATG AGC     624
Gly Phe Glu Ile Ala Val Lys Lys Ala Arg Pro Trp Thr Val Met Ser
        195                 200                 205

GCT TAC AAC AAA CTG AAT GGA AAA TAC TGT TCA CAG AAC GAA TGG CTT     672
Ala Tyr Asn Lys Leu Asn Gly Lys Tyr Cys Ser Gln Asn Glu Trp Leu
    210                 215                 220

TTG AAG AAG GTT CTC AGG GAA GAA TGG GGA TTT GGC GGT TTC GTG ATG     720
Leu Lys Lys Val Leu Arg Glu Glu Trp Gly Phe Gly Gly Phe Val Met
225                 230                 235                 240

AGC GAC TGG TAC GCG GGA GAC AAC CCT GTA GAA CAG CTC AAG GCC GGA     768
Ser Asp Trp Tyr Ala Gly Asp Asn Pro Val Glu Gln Leu Lys Ala Gly
                245                 250                 255
```

FIG. 5a

```
AAC GAT ATG ATC ATG CCT GGG AAA GCG TAT CAG GTG AAC ACA GAA AGA      816
Asn Asp Met Ile Met Pro Gly Lys Ala Tyr Gln Val Asn Thr Glu Arg
            260                 265                 270

AGA GAT GAA ATA GAA GAA ATC ATG GAG GCG TTG AAG GAG GGA AAA TTG      864
Arg Asp Glu Ile Glu Glu Ile Met Glu Ala Leu Lys Glu Gly Lys Leu
        275                 280                 285

AGT GAG GAG GTT CTC GAT GAG TGT GTG AGA AAC ATT CTC AAA GTT CTT      912
Ser Glu Glu Val Leu Asp Glu Cys Val Arg Asn Ile Leu Lys Val Leu
    290                 295                 300

GTG AAC GCG CCT TCC TTC AAA GGG TAC AGG TAC TCA AAC AAG CCG GAT      960
Val Asn Ala Pro Ser Phe Lys Gly Tyr Arg Tyr Ser Asn Lys Pro Asp
305                 310                 315                 320

CTC GAA TCT CAC GCG GAA GTC GCC TAC GAA GCA GGT GCG GAG GGT GTT     1008
Leu Glu Ser His Ala Glu Val Ala Tyr Glu Ala Gly Ala Glu Gly Val
                325                 330                 335

GTC CTT CTT GAG AAC AAC GGT GTT CTT CCG TTC GAT GAA AAT ACC CAT     1056
Val Leu Leu Glu Asn Asn Gly Val Leu Pro Phe Asp Glu Asn Thr His
            340                 345                 350

GTC GCC GTC TTT GGC ACC GGT CAA ATC GAA ACA ATA AAG GGA GGA ACG     1104
Val Ala Val Phe Gly Thr Gly Gln Ile Glu Thr Ile Lys Gly Gly Thr
        355                 360                 365

GGA AGT GGA GAC ACC CAT CCG AGA TAC ACG ATC TCT ATC CTT GAA GGC     1152
Gly Ser Gly Asp Thr His Pro Arg Tyr Thr Ile Ser Ile Leu Glu Gly
    370                 375                 380

ATA AAA GAA AGA AAC ATG AAG TTC GAC GAA GAA CTC GCT TCC ACT TAT     1200
Ile Lys Glu Arg Asn Met Lys Phe Asp Glu Glu Leu Ala Ser Thr Tyr
385                 390                 395                 400

GAG GAG TAC ATA AAA AAG ATG AGA GAA ACA GAG GAA TAT AAA CCC AGA     1248
Glu Glu Tyr Ile Lys Lys Met Arg Glu Thr Glu Glu Tyr Lys Pro Arg
                405                 410                 415

ACC GAC TCT TGG GGA ACG GTC ATA AAA CCG AAA CTC CCA GAG AAT TTC     1296
Thr Asp Ser Trp Gly Thr Val Ile Lys Pro Lys Leu Pro Glu Asn Phe
            420                 425                 430

CTC TCA GAA AAA GAG ATA AAG AAA CCT CCA AAG AAA AAC GAT GTT GCA     1344
Leu Ser Glu Lys Glu Ile Lys Lys Pro Pro Lys Lys Asn Asp Val Ala
        435                 440                 445

GTT GTT GTG ATC AGT AGG ATC TCC GGT GAG GGA TAC GAC AGA AAG CCG     1392
Val Val Val Ile Ser Arg Ile Ser Gly Glu Gly Tyr Asp Arg Lys Pro
    450                 455                 460

GTG AAA GGT GAC TTC TAC CTC TCC GAT GAC GAG CTG GAA CTC ATA AAA     1440
Val Lys Gly Asp Phe Tyr Leu Ser Asp Asp Glu Leu Glu Leu Ile Lys
465                 470                 475                 480

ACC GTC TCG AAA GAA TTC CAC GAT CAG GGT AAG AAA GTT GTG GTT CTT     1488
Thr Val Ser Lys Glu Phe His Asp Gln Gly Lys Lys Val Val Val Leu
485                 490                 495

CTG AAC ATC GGA AGT CCC ATC GAA GTC GCA AGC TGG AGA GAC CTT GTG     1536
Leu Asn Ile Gly Ser Pro Ile Glu Val Ala Ser Trp Arg Asp Leu Val
            500                 505                 510
```

FIG. 5b

```
GAT GGA ATT CTT CTC GTC TGG CAG GCG GGA CAG GAG ATG GGA AGA ATA    1584
Asp Gly Ile Leu Leu Val Trp Gln Ala Gly Gln Glu Met Gly Arg Ile
        515                     520                     525

GTG GCC GAT GTT CTT GTG GGA AAG ATT AAT CCC TCC GGA AAA CTT CCA    1632
Val Ala Asp Val Leu Val Gly Lys Ile Asn Pro Ser Gly Lys Leu Pro
    530                     535                     540

ACG ACC TTC CCG AAG GAT TAC TCG GAC GTT CCA TCC TGG ACG TTC CCA    1680
Thr Thr Phe Pro Lys Asp Tyr Ser Asp Val Pro Ser Trp Thr Phe Pro
545                     550                     555                     560

GGA GAG CCA AAG GAC AAT CCG CAA AGA GTG GTG TAC GAG GAA GAC ATC    1728
Gly Glu Pro Lys Asp Asn Pro Gln Arg Val Val Tyr Glu Glu Asp Ile
                565                     570                     575

TAC GTG GGA TAC AGG TAC TAC GAC ACC TTC GGT GTG GAA CCT GCC TAC    1776
Tyr Val Gly Tyr Arg Tyr Tyr Asp Thr Phe Gly Val Glu Pro Ala Tyr
            580                     585                     590

GAA TTC GGC TAC GGC CTC TCT TAC ACA AAG TTT GAA TAC AAA GAT TTA    1824
Glu Phe Gly Tyr Gly Leu Ser Tyr Thr Lys Phe Glu Tyr Lys Asp Leu
        595                     600                     605

AAA ATC GCT ATC GAC GGT GAG ACG CTC AGA GTG TCG TAC ACG ATC ACA    1872
Lys Ile Ala Ile Asp Gly Glu Thr Leu Arg Val Ser Tyr Thr Ile Thr
    610                     615                     620

AAC ACT GGG GAC AGA GCT GGA AAG GAA GTC TCA CAG GTC TAC ATC AAA    1920
Asn Thr Gly Asp Arg Ala Gly Lys Glu Val Ser Gln Val Tyr Ile Lys
625                     630                     635                     640

GCT CCA AAA GGA AAA ATA GAC AAA CCC TTC CAG GAG CTG AAA GCG TTT    1968
Ala Pro Lys Gly Lys Ile Asp Lys Pro Phe Gln Glu Leu Lys Ala Phe
                645                     650                     655

CAC AAA ACA AAA CTT TTG AAC CCG GGT GAA TCA GAA GAA ATC TCC TTG    2016
His Lys Thr Lys Leu Leu Asn Pro Gly Glu Ser Glu Glu Ile Ser Leu
            660                     665                     670

GAA ATT CCT CTC AGA GAT CTT GCG AGT TTC GAT GGG AAA GAA TGG GTT    2064
Glu Ile Pro Leu Arg Asp Leu Ala Ser Phe Asp Gly Lys Glu Trp Val
        675                     680                     685

GTC GAG TCA GGA GAA TAC GAG GTC AGG GTC GGT GCA TCT TCG AGG GAT    2112
Val Glu Ser Gly Glu Tyr Glu Val Arg Val Gly Ala Ser Ser Arg Asp
    690                     695                     700

ATA AGG TTG AGA GAT ATT TTT CTG GTT GAG GGA GAG AAG AGA TTC AAA    2160
Ile Arg Leu Arg Asp Ile Phe Leu Val Glu Gly Glu Lys Arg Phe Lys
705                     710                     715                     720

CCA TGA                                                            2166
Pro
```

FIG. 5c

THERMOCOCCUS AEDII 12RA GLYCOSIDASE (18B/G)
COMPLETE GENE SEQUENCE - 9/95

```
ATG ATC CAC TGC CCG GTT AAA GGG ATT ATA TCT GAG GCT CGC GGC ATA      48
Met Ile His Cys Pro Val Lys Gly Ile Ile Ser Glu Ala Arg Gly Ile
  1               5                  10                  15

ACC ATC ACA ATA GAT TTA AGT TTT CAA GGC CAA ATA AAT AAT TTG GTG      96
Thr Ile Thr Ile Asp Leu Ser Phe Gln Gly Gln Ile Asn Asn Leu Val
             20                  25                  30

AAT GCT ATG ATT GTC TTT CCG GAG TTC TTC CTC TTT GGA ACC GCC ACA     144
Asn Ala Met Ile Val Phe Pro Glu Phe Phe Leu Phe Gly Thr Ala Thr
         35                  40                  45

TCT TCT CAT CAG ATC GAG GGA GAT AAT AAA TGG AAC GAC TGG TGG TAT     192
Ser Ser His Gln Ile Glu Gly Asp Asn Lys Trp Asn Asp Trp Trp Tyr
     50                  55                  60

TAT GAG GAG ATA GGT AAG CTC CCC TAC AAA TCC GGT AAA GCC TGC AAT     240
Tyr Glu Glu Ile Gly Lys Leu Pro Tyr Lys Ser Gly Lys Ala Cys Asn
 65                  70                  75                  80

CAC TGG GAG CTT TAC AGG GAA GAT ATA GAG CTA ATG GCA CAG CTC GGC     288
His Trp Glu Leu Tyr Arg Glu Asp Ile Glu Leu Met Ala Gln Leu Gly
                 85                  90                  95

TAC AAT GCC TAC CGC TTT TCG ATA GAG TGG AGC CGT CTC TTC CCG GAA     336
Tyr Asn Ala Tyr Arg Phe Ser Ile Glu Trp Ser Arg Leu Phe Pro Glu
            100                 105                 110

GAG GGC AAA TTC AAT GAA GAA GCC TTC AAC CGC TAC CGT GAA ATA ATT     384
Glu Gly Lys Phe Asn Glu Glu Ala Phe Asn Arg Tyr Arg Glu Ile Ile
        115                 120                 125

GAA ATC CTC CTT GAG AAG GGG ATT ACT CCA AAC GTT ACA CTG CAC CAC     432
Glu Ile Leu Leu Glu Lys Gly Ile Thr Pro Asn Val Thr Leu His His
    130                 135                 140

TTC ACA TCA CCG CTG TGG TTC ATG CGG AAG GGA GGC TTT TTG AAG GAA     480
Phe Thr Ser Pro Leu Trp Phe Met Arg Lys Gly Gly Phe Leu Lys Glu
145                 150                 155                 160

GAA AAC CTC AAG TAC TGG GAG CAG TAC GTT GAT AAA GCC GCG GAG CTC     528
Glu Asn Leu Lys Tyr Trp Glu Gln Tyr Val Asp Lys Ala Ala Glu Leu
                165                 170                 175

CTC AAG GGA GTC AAG CTT GTA GCT ACA TTC AAC GAG CCG ATG GTC TAT     576
Leu Lys Gly Val Lys Leu Val Ala Thr Phe Asn Glu Pro Met Val Tyr
            180                 185                 190

GTT ATG ATG GGC TAC CTC ACA GCC TAC TGG CCG CCC TTC ATC AAG AGT     624
Val Met Met Gly Tyr Leu Thr Ala Tyr Trp Pro Pro Phe Ile Lys Ser
        195                 200                 205

CCC TTT AAA GCC TTT AAA GTT GCC GCA AAC CTC CTT AAG GCC CAT GCA     672
Pro Phe Lys Ala Phe Lys Val Ala Ala Asn Leu Leu Lys Ala His Ala
    210                 215                 220
```

FIG. 6a

```
ATG GCA TAT GAT ATC CTC CAT GGT AAC TTT GAT GTG GGG ATA GTT AAA    720
Met Ala Tyr Asp Ile Leu His Gly Asn Phe Asp Val Gly Ile Val Lys
225                 230                 235                 240

AAC ATC CCC ATA ATG CTC CCT GCA AGC AAC AGA GAG AAA GAC GTA GAA    768
Asn Ile Pro Ile Met Leu Pro Ala Ser Asn Arg Glu Lys Asp Val Glu
                245                 250                 255

GCT GCC CAA AAG GCG GAT AAC CTC TTT AAC TGG AAC TTC CTT GAT GCA    816
Ala Ala Gln Lys Ala Asp Asn Leu Phe Asn Trp Asn Phe Leu Asp Ala
            260                 265                 270

ATA TGG AGC GGA AAA TAT AAA GGA GCT TTT GGA ACT TAC AAA ACT CCA    864
Ile Trp Ser Gly Lys Tyr Lys Gly Ala Phe Gly Thr Tyr Lys Thr Pro
        275                 280                 285

GAA AGC GAT GCA GAC TTC ATA GGG ATA AAC TAC TAC ACA GCC AGC GAG    912
Glu Ser Asp Ala Asp Phe Ile Gly Ile Asn Tyr Tyr Thr Ala Ser Glu
    290                 295                 300

GTA AGG CAT AGC TGG AAT CCG CTA AAG TTT TTC TTC GAT GCC AAG CTT    960
Val Arg His Ser Trp Asn Pro Leu Lys Phe Phe Phe Asp Ala Lys Leu
305                 310                 315                 320

GCA GAC TTA AGC GAG AGA AAA ACA GAT ATG GGT TGG AGT GTC TAT CCA   1008
Ala Asp Leu Ser Glu Arg Lys Thr Asp Met Gly Trp Ser Val Tyr Pro
                325                 330                 335

AAG GGC ATA TAC GAA GCT ATA GCA AAG GTT TCA CAC TAC GGA AAG CCA   1056
Lys Gly Ile Tyr Glu Ala Ile Ala Lys Val Ser His Tyr Gly Lys Pro
            340                 345                 350

ATG TAC ATC ACG GAA AAC GGG ATA GCT ACC TTA GAC GAT GAG TGG AGG   1104
Met Tyr Ile Thr Glu Asn Gly Ile Ala Thr Leu Asp Asp Glu Trp Arg
        355                 360                 365

ATA GAG TTT ATC ATC CAG CAC CTC CAG TAC GTT CAC AAA GCC TTA AAC   1152
Ile Glu Phe Ile Ile Gln His Leu Gln Tyr Val His Lys Ala Leu Asn
    370                 375                 380

GAT GGC TTT GAC TTG AGA GGC TAC TTC TAT TGG TCT TTT ATG GAT AAC   1200
Asp Gly Phe Asp Leu Arg Gly Tyr Phe Tyr Trp Ser Phe Met Asp Asn
385                 390                 395                 400

TTC GAG TGG GCT GAG GGT TTT AGA CCA CGC TTT GGG CTG GTC GAG GTG   1248
Phe Glu Trp Ala Glu Gly Phe Arg Pro Arg Phe Gly Leu Val Glu Val
                405                 410                 415

GAC TAC ACG ACC TTC AAG AGG AGA CCG AGA AAG AGT GCT TAC ATA TAT   1296
Asp Tyr Thr Thr Phe Lys Arg Arg Pro Arg Lys Ser Ala Tyr Ile Tyr
            420                 425                 430

GGA GAA ATT GCA AGG GAA AAG AAA ATA AAA GAC GAA CTG CTG GCA AAG   1344
Gly Glu Ile Ala Arg Glu Lys Lys Ile Lys Asp Glu Leu Leu Ala Lys
        435                 440                 445

TAT GGG CTT CCG GAG CTA TGA                                      1365
Tyr Gly Leu Pro Glu Leu
        450
```

FIG. 6b

THERMOCOCCUS CHITONPHAGUS GLYCOSIDASE - 22G
COMPLETE SEQUENCE - 9/95

```
TTG CTT CCA GAG AAC TTT CTC TGG GGA GTT TCA CAG TCC GGA TTC CAG      48
Leu Leu Pro Glu Asn Phe Leu Trp Gly Val Ser Gln Ser Gly Phe Gln
 1               5                  10                  15

TTT GAA ATG GGG GAC AGA CTG AGG AGG CAC ATT GAT CCA AAC ACA GAT      96
Phe Glu Met Gly Asp Arg Leu Arg Arg His Ile Asp Pro Asn Thr Asp
            20                  25                  30

TGG TGG TAC TGG GTA AGA GAT GAA TAT AAT ATC AAA AAA GGA CTA GTA     144
Trp Trp Tyr Trp Val Arg Asp Glu Tyr Asn Ile Lys Lys Gly Leu Val
        35                  40                  45

AGT GGG GAT CTT CCC GAA GAC GGT ATA AAT TCA TAT GAA TTA TAT GAG     192
Ser Gly Asp Leu Pro Glu Asp Gly Ile Asn Ser Tyr Glu Leu Tyr Glu
    50                  55                  60

AGA GAC CAA GAA ATT GCA AAG GAT TTA GGG CTC AAC ACA TAT AGG ATC     240
Arg Asp Gln Glu Ile Ala Lys Asp Leu Gly Leu Asn Thr Tyr Arg Ile
 65                  70                  75                  80

GGA ATT GAA TGG AGC AGA GTA TTT CCA TGG CCA ACG ACT TTT GTC GAC     288
Gly Ile Glu Trp Ser Arg Val Phe Pro Trp Pro Thr Thr Phe Val Asp
                85                  90                  95

GTG GAG TAT GAA ATT GAT GAG TCT TAC GGG TTG GTA AAG GAT GTG AAG     336
Val Glu Tyr Glu Ile Asp Glu Ser Tyr Gly Leu Val Lys Asp Val Lys
            100                 105                 110

ATT TCT AAA GAC GCA TTA GAA AAA CTT GAT GAA ATC GCT AAC CAA AGG     384
Ile Ser Lys Asp Ala Leu Glu Lys Leu Asp Glu Ile Ala Asn Gln Arg
        115                 120                 125

GAA ATA ATA TAT TAT AGG AAC CTA ATA AAT TCC CTA AGA AAG AGG GGT     432
Glu Ile Ile Tyr Tyr Arg Asn Leu Ile Asn Ser Leu Arg Lys Arg Gly
    130                 135                 140

TTT AAG GTA ATA CTA AAC CTA AAT CAT TTT ACC CTC CCA ATA TGG CTT     480
Phe Lys Val Ile Leu Asn Leu Asn His Phe Thr Leu Pro Ile Trp Leu
145                 150                 155                 160

CAT GAT CCT ATC GAA TCT AGA GAA AAA GCC CTG ACC AAT AAG AGA AAC     528
His Asp Pro Ile Glu Ser Arg Glu Lys Ala Leu Thr Asn Lys Arg Asn
                165                 170                 175

GGA TGG GTA AGC GAA AGG AGT GTT ATA GAG TTT GCA AAA TTT GCC GCG     576
Gly Trp Val Ser Glu Arg Ser Val Ile Glu Phe Ala Lys Phe Ala Ala
            180                 185                 190

TAT TTA GCA TAT AAA TTC GGA GAC ATA GTA GAC ATG TGG AGC ACA TTT     624
Tyr Leu Ala Tyr Lys Phe Gly Asp Ile Val Asp Met Trp Ser Thr Phe
        195                 200                 205

AAT GAA CCT ATG GTG GTC GCC GAG TTG GGG TAT TTA GCC CCA TAC TCA     672
Asn Glu Pro Met Val Val Ala Glu Leu Gly Tyr Leu Ala Pro Tyr Ser
    210                 215                 220

GGA TTC CCC CCG GGA GTC ATG AAT CCA GAA GCA GCA AAG TTA GTT ATG     720
Gly Phe Pro Pro Gly Val Met Asn Pro Glu Ala Ala Lys Leu Val Met
225                 230                 235                 240

CTA CAT ATG ATA AAC GCC CAT GCT TTA GCA TAT AGG ATG ATA AAG AAA     768
Leu His Met Ile Asn Ala His Ala Leu Ala Tyr Arg Met Ile Lys Lys
                245                 250                 255
```

FIG. 7a

```
TTT GAC AGA AAA AAA GCT GAT CCA GAA TCA AAA GAA CCA GCT GAA ATA     816
Phe Asp Arg Lys Lys Ala Asp Pro Glu Ser Lys Glu Pro Ala Glu Ile
            260                 265                 270

GGA ATT ATA TAC AAT AAC ATC GGC GTC ACA TAT CCG TTT AAT CCG AAA     864
Gly Ile Ile Tyr Asn Asn Ile Gly Val Thr Tyr Pro Phe Asn Pro Lys
        275                 280                 285

GAC TCA AAG GAT CTA CAA GCA TCC GAT AAT GCC AAT TTC TTC CAC AGT     912
Asp Ser Lys Asp Leu Gln Ala Ser Asp Asn Ala Asn Phe Phe His Ser
    290                 295                 300

 GG CTA TTC TTA ACG GCT ATC CAC AGG GGA AAA TTA AAT ATC GAA TTT     960
Gly Leu Phe Leu Thr Ala Ile His Arg Gly Lys Leu Asn Ile Glu Phe
305                 310                 315                 320

GAC GGA GAG ACA TTT GTT TAC CTT CCA TAT TTA AAG GGC AAT GAT TGG    1008
Asp Gly Glu Thr Phe Val Tyr Leu Pro Tyr Leu Lys Gly Asn Asp Trp
                325                 330                 335

CTG GGA GTG AAT TAT TAT ACA AGA GAA GTC GTT AAA TAC CAA GAT CCC    1056
Leu Gly Val Asn Tyr Tyr Thr Arg Glu Val Val Lys Tyr Gln Asp Pro
            340                 345                 350

ATG TTT CCA AGT ATC CCT CTC ATA AGC TTC AAG GGC GTT CCA GAT TAT    1104
Met Phe Pro Ser Ile Pro Leu Ile Ser Phe Lys Gly Val Pro Asp Tyr
        355                 360                 365

GGA TAC GGA TGT AGA CCA GGA ACG ACG TCA AAG GAC GGT AAT CCT GTT    1152
Gly Tyr Gly Cys Arg Pro Gly Thr Thr Ser Lys Asp Gly Asn Pro Val
    370                 375                 380

AGT GAC ATT GGA TGG GAG GTA TAT CCC AAA GGC ATG TAC GAC TCT ATA    1200
Ser Asp Ile Gly Trp Glu Val Tyr Pro Lys Gly Met Tyr Asp Ser Ile
385                 390                 395                 400

GTA GCT GCC AAT GAA TAT GGA GTT CCT GTA TAC GTA ACA GAA AAC GGA    1248
Val Ala Ala Asn Glu Tyr Gly Val Pro Val Tyr Val Thr Glu Asn Gly
                405                 410                 415

ATA GCA GAT TCA AAA GAT GTA TTA AGG CCC TAT TAC ATC GCA TCT CAC    1296
Ile Ala Asp Ser Lys Asp Val Leu Arg Pro Tyr Tyr Ile Ala Ser His
            420                 425                 430

ATT GAA GCC ATG GAA GAG GCT TAC GAA AAT GGT TAT GAC GTG AGA GGA    1344
Ile Glu Ala Met Glu Glu Ala Tyr Glu Asn Gly Tyr Asp Val Arg Gly
        435                 440                 445

TAC TTA CAC TGG GCA TTA ACC GAT AAT TAC GAA TGG GCC TTA GGG TTC    1392
Tyr Leu His Trp Ala Leu Thr Asp Asn Tyr Glu Trp Ala Leu Gly Phe
    450                 455                 460

AGA ATG AGG TTT GGC TTG TAC GAA GTA AAC TTG ATA ACC AAA GAG AGA    1440
Arg Met Arg Phe Gly Leu Tyr Glu Val Asn Leu Ile Thr Lys Glu Arg
465                 470                 475                 480

AAA CCC AGG AAA AAG AGT GTA AGA GTA TTC AGA GAG ATA GTT ATT AAT    1488
Lys Pro Arg Lys Lys Ser Val Arg Val Phe Arg Glu Ile Val Ile Asn
                485                 490                 495

AAT GGG CTA ACA AGC AAC ATC AGG AAA GAG ATC TTA GAG GAG GGG TAG    1536
Asn Gly Leu Thr Ser Asn Ile Arg Lys Glu Ile Leu Glu Glu Gly
            500                 505                 510
```

FIG. 7b

PYROCOCCUS FURIOSUS GLYCOSIDASE - 7G1
COMPLETE GENE SEQUENCE - 10/95

```
ATG TTC CCT GAA AAG TTC CTT TGG GGT GTG GCA CAA TCG GGT TTT CAG      48
Met Phe Pro Glu Lys Phe Leu Trp Gly Val Ala Gln Ser Gly Phe Gln
  1               5                  10                  15

TTT GAA ATG GGG GAT AAA CTC AGG AGG AAT ATT GAC ACT AAC ACT GAT      96
Phe Glu Met Gly Asp Lys Leu Arg Arg Asn Ile Asp Thr Asn Thr Asp
             20                  25                  30

TGG TGG CAC TGG GTA AGG GAT AAG ACA AAT ATA GAG AAA GGC CTC GTT     144
Trp Trp His Trp Val Arg Asp Lys Thr Asn Ile Glu Lys Gly Leu Val
         35                  40                  45

AGT GGA GAT CTT CCC GAG GAG GGG ATT AAC AAT TAC GAG CTT TAT GAG     192
Ser Gly Asp Leu Pro Glu Glu Gly Ile Asn Asn Tyr Glu Leu Tyr Glu
     50                  55                  60

AAG GAC CAT GAG ATT GCA AGA AAG CTG GGT CTT AAT GCT TAC AGA ATA     240
Lys Asp His Glu Ile Ala Arg Lys Leu Gly Leu Asn Ala Tyr Arg Ile
 65                  70                  75                  80

GGC ATA GAG TGG AGC AGA ATA TTC CCA TGG CCA ACG ACA TTT ATT GAT     288
Gly Ile Glu Trp Ser Arg Ile Phe Pro Trp Pro Thr Thr Phe Ile Asp
                 85                  90                  95

GTT GAT TAT AGC TAT AAT GAA TCA TAT AAC CTT ATA GAA GAT GTA AAG     336
Val Asp Tyr Ser Tyr Asn Glu Ser Tyr Asn Leu Ile Glu Asp Val Lys
            100                 105                 110

ATC ACC AAG GAC ACT TTG GAG GAG TTA GAT GAG ATC GCC AAC AAG AGG     384
Ile Thr Lys Asp Thr Leu Glu Glu Leu Asp Glu Ile Ala Asn Lys Arg
        115                 120                 125

GAG GTG GCC TAC TAT AGG TCA GTC ATA AAC AGC CTG AGG AGC AAG GGG     432
Glu Val Ala Tyr Tyr Arg Ser Val Ile Asn Ser Leu Arg Ser Lys Gly
    130                 135                 140

TTT AAG GTT ATA GTT AAT CTA AAT CAC TTC ACC CTT CCA TAT TGG TTG     480
Phe Lys Val Ile Val Asn Leu Asn His Phe Thr Leu Pro Tyr Trp Leu
145                 150                 155                 160

CAT GAT CCC ATT GAG GCT AGG GAG AGG GCG TTA ACT AAT AAG AGG AAC     528
His Asp Pro Ile Glu Ala Arg Glu Arg Ala Leu Thr Asn Lys Arg Asn
                165                 170                 175

GGC TGG GTT AAC CCA AGA ACA GTT ATA GAG TTT GCA AAG TAT GCC GCT     576
Gly Trp Val Asn Pro Arg Thr Val Ile Glu Phe Ala Lys Tyr Ala Ala
            180                 185                 190

TAC ATA GCC TAT AAG TTT GGA GAT ATA GTG GAT ATG TGG AGC ACG TTT     624
Tyr Ile Ala Tyr Lys Phe Gly Asp Ile Val Asp Met Trp Ser Thr Phe
        195                 200                 205

AAT GAG CCT ATG GTG GTT GTT GAG CTT GGC TAC CTA GCC CCC TAC TCT     672
Asn Glu Pro Met Val Val Val Glu Leu Gly Tyr Leu Ala Pro Tyr Ser
    210                 215                 220

GGC TTC CCT CCA GGG GTT CTA AAT CCA GAG GCC GCA AAG CTG GCG ATA     720
Gly Phe Pro Pro Gly Val Leu Asn Pro Glu Ala Ala Lys Leu Ala Ile
225                 230                 235                 240

CTT CAC ATG ATA AAT GCA CAT GCT TTA GCT TAT AGG CAG ATA AAG AAG     768
Leu His Met Ile Asn Ala His Ala Leu Ala Tyr Arg Gln Ile Lys Lys
                245                 250                 255
```

FIG. 8a

```
TTT GAC ACT GAG AAA GCT GAT AAG GAT TCT AAA GAG CCT GCA GAA GTT    816
Phe Asp Thr Glu Lys Ala Asp Lys Asp Ser Lys Glu Pro Ala Glu Val
            260                 265                 270

GGT ATA ATT TAC AAC AAC ATT GGA GTT GCT TAT CCC AAG GAT CCG AAC    864
Gly Ile Ile Tyr Asn Asn Ile Gly Val Ala Tyr Pro Lys Asp Pro Asn
        275                 280                 285

GAT TCC AAG GAT GTT AAG GCA GCA GAA AAC GAC AAC TTC TTC CAC TCA    912
Asp Ser Lys Asp Val Lys Ala Ala Glu Asn Asp Asn Phe Phe His Ser
    290                 295                 300

GGG CTG TTC TTC GAG GCC ATA CAC AAA GGA AAA CTT AAT ATA GAG TTT    960
Gly Leu Phe Phe Glu Ala Ile His Lys Gly Lys Leu Asn Ile Glu Phe
305                 310                 315                 320

GAC GGT GAA ACG TTT ATA GAT GCC CCC TAT CTA AAG GGC AAT GAC TGG   1008
Asp Gly Glu Thr Phe Ile Asp Ala Pro Tyr Leu Lys Gly Asn Asp Trp
                325                 330                 335

ATA GGG GTT AAT TAC TAC ACA AGG GAA GTA GTT ACG TAT CAG GAA CCA   1056
Ile Gly Val Asn Tyr Tyr Thr Arg Glu Val Val Thr Tyr Gln Glu Pro
            340                 345                 350

ATG TTT CCT TCA ATC CCG CTG ATC ACC TTT AAG GGA GTT CAA GGA TAT   1104
Met Phe Pro Ser Ile Pro Leu Ile Thr Phe Lys Gly Val Gln Gly Tyr
        355                 360                 365

GGC TAT GCC TGC AGA CCT GGA ACT CTG TCA AAG GAT GAC AGA CCC GTC   1152
Gly Tyr Ala Cys Arg Pro Gly Thr Leu Ser Lys Asp Asp Arg Pro Val
    370                 375                 380

AGC GAC ATA GGA TGG GAA CTC TAT CCA GAG GGG ATG TAC GAT TCA ATA   1200
Ser Asp Ile Gly Trp Glu Leu Tyr Pro Glu Gly Met Tyr Asp Ser Ile
385                 390                 395                 400

GTT GAA GCT CAC AAG TAC GGC GTT CCA GTT TAC GTG ACG GAG AAC GGA   1248
Val Glu Ala His Lys Tyr Gly Val Pro Val Tyr Val Thr Glu Asn Gly
                405                 410                 415

ATA GCG GAT TCA AAG GAC ATC CTA AGA CCT TAC TAC ATA GCG AGC CAC   1296
Ile Ala Asp Ser Lys Asp Ile Leu Arg Pro Tyr Tyr Ile Ala Ser His
            420                 425                 430

ATA AAG ATG ATA GAG AAG GCC TTT GAG GAT GGG TAT GAA GTT AAG GGC   1344
Ile Lys Met Ile Glu Lys Ala Phe Glu Asp Gly Tyr Glu Val Lys Gly
        435                 440                 445

TAC TTC CAC TGG GCA TTA ACT GAC AAC TTC GAG TGG GCT CTC GGG TTT   1392
Tyr Phe His Trp Ala Leu Thr Asp Asn Phe Glu Trp Ala Leu Gly Phe
    450                 455                 460

AGA ATG CGC TTT GGC CTC TAC GAA GTC AAC CTA ATT ACA AAG GAG AGA   1440
Arg Met Arg Phe Gly Leu Tyr Glu Val Asn Leu Ile Thr Lys Glu Arg
465                 470                 475                 480

ATT CCC AGG GAG AAG AGC GTG TCG ATA TTC AGA GAG ATA GTA GCC AAT   1488
Ile Pro Arg Glu Lys Ser Val Ser Ile Phe Arg Glu Ile Val Ala Asn
                485                 490                 495

AAT GGT GTT ACG AAA AAG ATT GAA GAG GAA TTG CTG AGG GGA TGA       1533
Asn Gly Val Thr Lys Lys Ile Glu Glu Glu Leu Leu Arg Gly
            500                 505                 510
```

FIG. 8b

BANKIA GOULDI ENDOGLUCANASE (37GF1)

```
ATG AGA ATA CGT TTA GCG ACG CTC GCG CTC TGC GCA GCG CTG AGC CCA     48
Met Arg Ile Arg Leu Ala Thr Leu Ala Leu Cys Ala Ala Leu Ser Pro
 1               5                  10                  15

GTC ACC TTT GCA GAT AAT GTA ACC GTA CAA ATC GAC GCC GAC GGC GGT     96
Val Thr Phe Ala Asp Asn Val Thr Val Gln Ile Asp Ala Asp Gly Gly
            20                  25                  30

AAA AAA CTC ATC AGC CGA GCC CTT TAC GGC ATG AAT AAC TCC AAC GCA    144
Lys Lys Leu Ile Ser Arg Ala Leu Tyr Gly Met Asn Asn Ser Asn Ala
        35                  40                  45

GAA AGC CTT ACC GAT ACT GAC TGG CAG CGT TTT CGC GAT GCA GGT GTG    192
Glu Ser Leu Thr Asp Thr Asp Trp Gln Arg Phe Arg Asp Ala Gly Val
    50                  55                  60

CGC ATG CTG CGG GAA AAT GGC GGC AAC AAC AGC ACC AAA TAT AAC TGG    240
Arg Met Leu Arg Glu Asn Gly Gly Asn Asn Ser Thr Lys Tyr Asn Trp
65                  70                  75                  80

CAA CTG CAC CTG AGC AGT CAT CCG GAT TGG TAC AAC AAT GTC TAC GCC    288
Gln Leu His Leu Ser Ser His Pro Asp Trp Tyr Asn Asn Val Tyr Ala
                85                  90                  95

GGC AAC AAC AAC TGG GAC AAC CGG GTA GCC CTG ATT CAG GAA AAC CTG    336
Gly Asn Asn Asn Trp Asp Asn Arg Val Ala Leu Ile Gln Glu Asn Leu
            100                 105                 110

CCC GGC GCC GAC ACC ATG TGG GCA TTC CAG CTC ATC GGT AAG GTC GCG    384
Pro Gly Ala Asp Thr Met Trp Ala Phe Gln Leu Ile Gly Lys Val Ala
        115                 120                 125

GCG ACT TCT GCC TAC AAC TTT AAC GAT TGG GAA TTC AAC CAG TCG CAA    432
Ala Thr Ser Ala Tyr Asn Phe Asn Asp Trp Glu Phe Asn Gln Ser Gln
    130                 135                 140

TGG TGG ACC GGC GTC GCT CAG AAT CTC GCT GGC GGC GGT GAA CCC AAT    480
Trp Trp Thr Gly Val Ala Gln Asn Leu Ala Gly Gly Gly Glu Pro Asn
145                 150                 155                 160

CTG GAC GGC GGC GGC GAA GCG CTG GTT GAA GGA GAC CCC AAT CTC TAC    528
Leu Asp Gly Gly Gly Glu Ala Leu Val Glu Gly Asp Pro Asn Leu Tyr
                165                 170                 175

CTC ATG GAT TGG TCG CCA GCC GAC ACT GTG GGT ATT CTC GAC CAC TGG    576
Leu Met Asp Trp Ser Pro Ala Asp Thr Val Gly Ile Leu Asp His Trp
            180                 185                 190

TTT GGC GTA AAC GGG CTG GGC GTG CGG CGT GGC AAA GCC AAA TAC TGG    624
Phe Gly Val Asn Gly Leu Gly Val Arg Arg Gly Lys Ala Lys Tyr Trp
        195                 200                 205

AGT ATG GAT AAC GAG CCC GGC ATC TGG GTT GGC ACC CAC GAC GAT GTA    672
Ser Met Asp Asn Glu Pro Gly Ile Trp Val Gly Thr His Asp Asp Val
    210                 215                 220
```

FIG. 9a

BANKIA GOULDI ENDOGLUCANASE (37GF1)(CONTINUED)

```
GTG AAA GAA CAA ACG CCG GTA GAA GAT TTC CTG CAC ACC TAT TTC GAA    720
Val Lys Glu Gln Thr Pro Val Glu Asp Phe Leu His Thr Tyr Phe Glu
225                 230                 235                 240

ACC GCC AAA AAA GCC CGC GCC AAA TTT CCC GGT ATT AAA ATC ACC GGT    768
Thr Ala Lys Lys Ala Arg Ala Lys Phe Pro Gly Ile Lys Ile Thr Gly
                245                 250                 255

CCG GTG CCC GCT AAT GAG TGG CAG TGG TAT GCC TGG GGC GGT TTC TCG    816
Pro Val Pro Ala Asn Glu Trp Gln Trp Tyr Ala Trp Gly Gly Phe Ser
            260                 265                 270

GTA CCC CAG GAA CAA GGG TTT ATG AGC TGG ATG GAG TAT TTC ATC AAG    864
Val Pro Gln Glu Gln Gly Phe Met Ser Trp Met Glu Tyr Phe Ile Lys
        275                 280                 285

CGG GTG TCT GAA GAG CAA CGC GCA AGT GGT GTT CGC CTC CTC GAT GTA    912
Arg Val Ser Glu Glu Gln Arg Ala Ser Gly Val Arg Leu Leu Asp Val
    290                 295                 300

CTC GAT CTG CAC TAC TAC CCC GGC GCT TAC AAT GCG GAA GAT ATC GTG    960
Leu Asp Leu His Tyr Tyr Pro Gly Ala Tyr Asn Ala Glu Asp Ile Val
305                 310                 315                 320

CAA TTA CAT CGC ACG TTC TTC GAC CGC GAC TTT GTT TCA CTG GAT GCC   1008
Gln Leu His Arg Thr Phe Phe Asp Arg Asp Phe Val Ser Leu Asp Ala
                325                 330                 335

AAC GGG GTG AAA ATG GTA GAA GGT GGC TGG GAT GAC AGC ATC AAC AAG   1056
Asn Gly Val Lys Met Val Glu Gly Gly Trp Asp Asp Ser Ile Asn Lys
            340                 345                 350

GAA TAT ATT TTC GGG CGA GTG AAC GAT TGG CTC GAG GAA TAT ATG GGG   1104
Glu Tyr Ile Phe Gly Arg Val Asn Asp Trp Leu Glu Glu Tyr Met Gly
        355                 360                 365

CCA GAC CAT GGT GTA ACC CTG GGC TTA ACC GAA ATG TGC GTG CGC AAT   1152
Pro Asp His Gly Val Thr Leu Gly Leu Thr Glu Met Cys Val Arg Asn
    370                 375                 380

GTG AAT CCG ATG ACT ACC GCC ATC TGG TAT GCC TCC ATG CTC GGC ACC   1200
Val Asn Pro Met Thr Thr Ala Ile Trp Tyr Ala Ser Met Leu Gly Thr
385                 390                 395                 400

TTC GCG GAT AAC GGC GTC GAA ATA TTC ACC CCA TGG TGC TGG AAC ACC   1248
Phe Ala Asp Asn Gly Val Glu Ile Phe Thr Pro Trp Cys Trp Asn Thr
                405                 410                 415

GGA ATG TGG GAA ACA CTC CAC CTC TTC AGC CGC TAC AAC AAA CCT TAT   1296
Gly Met Trp Glu Thr Leu His Leu Phe Ser Arg Tyr Asn Lys Pro Tyr
            420                 425                 430

CGG GTC GCC TCC AGC TCC AGT CTT GAA GAG TTT GTC AGC GCC TAC AGC   1344
Arg Val Ala Ser Ser Ser Ser Leu Glu Glu Phe Val Ser Ala Tyr Ser
        435                 440                 445

TCC ATT AAC GAA GCA GAA GAC GCC ATG ACG GTA CTT CTG GTG AAT CGT   1392
Ser Ile Asn Glu Ala Glu Asp Ala Met Thr Val Leu Leu Val Asn Arg
    450                 455                 460
```

FIG. 9b

BANKIA GOULDI ENDOGLUCANASE (37GF1)(CONTINUED)

```
TCC ACT AGC GAG ACC CAC ACC GCC ACT GTC GCT ATC GAC GAT TTC CCA   1440
Ser Thr Ser Glu Thr His Thr Ala Thr Val Ala Ile Asp Asp Phe Pro
465                 470                 475                 480

CTG GAT GGC CCC TAC CGC ACC CTG CGC TTA CAC AAC CTG CCG GGG GAG   1488
Leu Asp Gly Pro Tyr Arg Thr Leu Arg Leu His Asn Leu Pro Gly Glu
                485                 490                 495

GAA ACC TTC GTA TCT CAC CGA GAC AAC GCC CTG GAA AAA GGT ACA GTG   1536
Glu Thr Phe Val Ser His Arg Asp Asn Ala Leu Glu Lys Gly Thr Val
            500                 505                 510

CGC GCC AGC GAC AAT ACG GTA ACA CTG GAG TTG CCC CCT CTG TCC GTT   1584
Arg Ala Ser Asp Asn Thr Val Thr Leu Glu Leu Pro Pro Leu Ser Val
        515                 520                 525

ACT GCA ATA TTG CTC AAG GCC CGG CCC TAA                           1614
Thr Ala Ile Leu Leu Lys Ala Arg Pro
    530                 535
```

FIG. 9c

THERMOTOGA MARITIMA ALPHA-GALACTOSIDASE
COMPLETE GENE SEQUENCE (1 OF 3)

```
GTG ATC TGT GTG GAA ATA TTC GGA AAG ACC TTC AGA GAG GGA AGA TTC      48
Val Ile Cys Val Glu Ile Phe Gly Lys Thr Phe Arg Glu Gly Arg Phe
  1               5                  10                  15

GTT CTC AAA GAG AAA AAC TTC ACA GTT GAG TTC GCG GTG GAG AAG ATA      96
Val Leu Lys Glu Lys Asn Phe Thr Val Glu Phe Ala Val Glu Lys Ile
             20                  25                  30

CAC CTT GGC TGG AAG ATC TCC GGC AGG GTG AAG GGA AGT CCG GGA AGG     144
His Leu Gly Trp Lys Ile Ser Gly Arg Val Lys Gly Ser Pro Gly Arg
         35                  40                  45

CTT GAG GTT CTT CGA ACG AAA GCA CCG GAA AAG GTA CTT GTG AAC AAC     192
Leu Glu Val Leu Arg Thr Lys Ala Pro Glu Lys Val Leu Val Asn Asn
     50                  55                  60

TGG CAG TCC TGG GGA CCG TGC AGG GTG GTC GAT GCC TTT TCT TTC AAA     240
Trp Gln Ser Trp Gly Pro Cys Arg Val Val Asp Ala Phe Ser Phe Lys
 65                  70                  75                  80

CCA CCT GAA ATA GAT CCG AAC TGG AGA TAC ACC GCT TCG GTG GTG CCC     288
Pro Pro Glu Ile Asp Pro Asn Trp Arg Tyr Thr Ala Ser Val Val Pro
                 85                  90                  95

GAT GTA CTT GAA AGG AAC CTC CAG AGC GAC TAT TTC GTG GCT GAA GAA     336
Asp Val Leu Glu Arg Asn Leu Gln Ser Asp Tyr Phe Val Ala Glu Glu
            100                 105                 110

GGA AAA GTG TAC GGT TTT CTG AGT TCG AAA ATC GCA CAT CCT TTC TTC     384
Gly Lys Val Tyr Gly Phe Leu Ser Ser Lys Ile Ala His Pro Phe Phe
        115                 120                 125

GCT GTG GAA GAT GGG GAA CTT GTG GCA TAC CTC GAA TAT TTC GAT GTC     432
Ala Val Glu Asp Gly Glu Leu Val Ala Tyr Leu Glu Tyr Phe Asp Val
    130                 135                 140

GAG TTC GAC GAC TTT GTT CCT CTT GAA CCT CTC GTT GTA CTC GAG GAT     480
Glu Phe Asp Asp Phe Val Pro Leu Glu Pro Leu Val Val Leu Glu Asp
145                 150                 155                 160

CCC AAC ACA CCC CTT CTT CTG GAG AAA TAC GCG GAA CTC GTC GGA ATG     528
Pro Asn Thr Pro Leu Leu Leu Glu Lys Tyr Ala Glu Leu Val Gly Met
                165                 170                 175

GAA AAC AAC GCG AGA GTT CCA AAA CAC ACA CCC ACT GGA TGG TGC AGC     576
Glu Asn Asn Ala Arg Val Pro Lys His Thr Pro Thr Gly Trp Cys Ser
            180                 185                 190

TGG TAC CAT TAC TTC CTT GAT CTC ACC TGG GAA GAG ACC CTC AAG AAC     624
Trp Tyr His Tyr Phe Leu Asp Leu Thr Trp Glu Glu Thr Leu Lys Asn
        195                 200                 205

CTG AAG CTC GCG AAG AAT TTC CCG TTC GAG GTC TTC CAG ATA GAC GAC     672
Leu Lys Leu Ala Lys Asn Phe Pro Phe Glu Val Phe Gln Ile Asp Asp
    210                 215                 220
```

FIG. 10a

THERMOTOGA MARITIMA ALPHA-GALACTOSIDASE
COMPLETE GENE SEQUENCE (2 OF 3)

```
GCC TAC GAA AAG GAC ATA GGT GAC TGG CTC GTG ACA AGA GGA GAC TTT     720
Ala Tyr Glu Lys Asp Ile Gly Asp Trp Leu Val Thr Arg Gly Asp Phe
225                 230                 235                 240

CCA TCG GTG GAA GAG ATG GCA AAA GTT ATA GCG GAA AAC GGT TTC ATC     768
Pro Ser Val Glu Glu Met Ala Lys Val Ile Ala Glu Asn Gly Phe Ile
                245                 250                 255

CCG GGC ATA TGG ACC GCC CCG TTC AGT GTT TCT GAA ACC TCG GAT GTA     816
Pro Gly Ile Trp Thr Ala Pro Phe Ser Val Ser Glu Thr Ser Asp Val
            260                 265                 270

TTC AAC GAA CAT CCG GAC TGG GTA GTG AAG GAA AAC GGA GAG CCG AAG     864
Phe Asn Glu His Pro Asp Trp Val Val Lys Glu Asn Gly Glu Pro Lys
        275                 280                 285

ATG GCT TAC AGA AAC TGG AAC AAA AAG ATA TAC GCC CTC GAT CTT TCG     912
Met Ala Tyr Arg Asn Trp Asn Lys Lys Ile Tyr Ala Leu Asp Leu Ser
    290                 295                 300

AAA GAT GAG GTT CTG AAC TGG CTT TTC GAT CTC TTC TCA TCT CTG AGA     960
Lys Asp Glu Val Leu Asn Trp Leu Phe Asp Leu Phe Ser Ser Leu Arg
305                 310                 315                 320

AAG ATG GGC TAC AGG TAC TTC AAG ATC GAC TTT CTC TTC GCG GGT GCC    1008
Lys Met Gly Tyr Arg Tyr Phe Lys Ile Asp Phe Leu Phe Ala Gly Ala
                325                 330                 335

GTT CCA GGA GAA AGA AAA AAG AAC ATA ACA CCA ATT CAG GCG TTC AGA    1056
Val Pro Gly Glu Arg Lys Lys Asn Ile Thr Pro Ile Gln Ala Phe Arg
            340                 345                 350

AAA GGG ATT GAG ACG ATC AGA AAA GCG GTG GGA GAA GAT TCT TTC ATC    1104
Lys Gly Ile Glu Thr Ile Arg Lys Ala Val Gly Glu Asp Ser Phe Ile
        355                 360                 365

CTC GGA TGC GGC TCT CCC CTT CTT CCC GCA GTG GGA TGC GTC GAC GGG    1152
Leu Gly Cys Gly Ser Pro Leu Leu Pro Ala Val Gly Cys Val Asp Gly
    370                 375                 380

ATG AGG ATA GGA CCT GAC ACT GCG CCG TTC TGG GGA GAA CAT ATA GAA    1200
Met Arg Ile Gly Pro Asp Thr Ala Pro Phe Trp Gly Glu His Ile Glu
385                 390                 395                 400

GAC AAC GGA GCT CCC GCT GCA AGA TGG GCG CTG AGA AAC GCC ATA ACG    1248
Asp Asn Gly Ala Pro Ala Ala Arg Trp Ala Leu Arg Asn Ala Ile Thr
                405                 410                 415

AGG TAC TTC ATG CAC GAC AGG TTC TGG CTG AAC GAC CCC GAC TGT CTG    1296
Arg Tyr Phe Met His Asp Arg Phe Trp Leu Asn Asp Pro Asp Cys Leu
                    420                 425                 430
```

FIG. 10b

THERMOTOGA MARITIMA ALPHA-GALACTOSIDASE
COMPLETE GENE SEQUENCE (3 OF 3)

```
ATA CTG AGA GAG GAG AAA ACG GAT CTC ACA CAG AAG GAA AAG GAG CTC    344
Ile Leu Arg Glu Glu Lys Thr Asp Leu Thr Gln Lys Glu Lys Glu Leu
        435                 440                 445

TAC TCG TAC ACG TGT GGA GTG CTC GAC AAC ATG ATC ATA GAA AGC GAT   1392
Tyr Ser Tyr Thr Cys Gly Val Leu Asp Asn Met Ile Ile Glu Ser Asp
    450                 455                 460

GAT CTC TCG CTC GTC AGA GAT CAT GGA AAA AAG GTT CTG AAA GAA ACG   1440
Asp Leu Ser Leu Val Arg Asp His Gly Lys Lys Val Leu Lys Glu Thr
465                 470                 475                 480

CTC GAA CTC CTC GGT GGA AGA CCA CGG GTT CAA AAC ATC ATG TCG GAG   1488
Leu Glu Leu Leu Gly Gly Arg Pro Arg Val Gln Asn Ile Met Ser Glu
                485                 490                 495

GAT CTG AGA TAC GAG ATC GTC TCG TCT GGC ACT CTC TCA GGA AAC GTC   1536
Asp Leu Arg Tyr Glu Ile Val Ser Ser Gly Thr Leu Ser Gly Asn Val
            500                 505                 510

AAG ATC GTG GTC GAT CTG AAC AGC AGA GAG TAC CAC CTG GAA AAA GAA   1584
Lys Ile Val Val Asp Leu Asn Ser Arg Glu Tyr His Leu Glu Lys Glu
        515                 520                 525

GGA AAG TCC TCC CTG AAA AAA AGA GTC GTC AAA AGA GAA GAC GGA AGA   1632
Gly Lys Ser Ser Leu Lys Lys Arg Val Val Lys Arg Glu Asp Gly Arg
    530                 535                 540

AAC TTC TAC TTC TAC GAA GAG GGT GAG AGA GAA TGA                   1668
Asn Phe Tyr Phe Tyr Glu Glu Gly Glu Arg Glu
              545                 550                 555
```

FIG. 10c

THERMOTOGA MARITINA β - MANNANASE (6GP2)

```
ATG GGG ATT GGT GGC GAC GAC TCC TGG AGC CCG TCA GTA TCG GCG GAA      48
Met Gly Ile Gly Gly Asp Asp Ser Trp Ser Pro Ser Val Ser Ala Glu
  1               5                  10                  15

TTC CTT TTA TTG ATC GTT GAG CTC TCT TTC GTT CTC TTT GCA AGT GAC      96
Phe Leu Leu Leu Ile Val Glu Leu Ser Phe Val Leu Phe Ala Ser Asp
             20                  25                  30

GAG TTC GTG AAA GTG GAA AAC GGA AAA TTC GCT CTG AAC GGA AAA GAA     144
Glu Phe Val Lys Val Glu Asn Gly Lys Phe Ala Leu Asn Gly Lys Glu
         35                  40                  45

TTC AGA TTC ATT GGA AGC AAC AAC TAC TAC ATG CAC TAC AAG AGC AAC     192
Phe Arg Phe Ile Gly Ser Asn Asn Tyr Tyr Met His Tyr Lys Ser Asn
     50                  55                  60

GGA ATG ATA GAC AGT GTT CTG GAG AGT GCC AGA GAC ATG GGT ATA AAG     240
Gly Met Ile Asp Ser Val Leu Glu Ser Ala Arg Asp Met Gly Ile Lys
 65                  70                  75                  80

GTC CTC AGA ATC TGG GGT TTC CTC GAC GGG GAG AGT TAC TGC AGA GAC     288
Val Leu Arg Ile Trp Gly Phe Leu Asp Gly Glu Ser Tyr Cys Arg Asp
                 85                  90                  95

AAG AAC ACC TAC ATG CAT CCT GAG CCC GGT GTT TTC GGG GTG CCA GAA     336
Lys Asn Thr Tyr Met His Pro Glu Pro Gly Val Phe Gly Val Pro Glu
            100                 105                 110

GGA ATA TCG AAC GCC CAG AGC GGT TTC GAA AGA CTC GAC TAC ACA GTT     384
Gly Ile Ser Asn Ala Gln Ser Gly Phe Glu Arg Leu Asp Tyr Thr Val
        115                 120                 125

GCG AAA GCG AAA GAA CTC GGT ATA AAA CTT GTC ATT GTT CTT GTG AAC     432
Ala Lys Ala Lys Glu Leu Gly Ile Lys Leu Val Ile Val Leu Val Asn
    130                 135                 140

AAC TGG GAC GAC TTC GGT GGA ATG AAC CAG TAC GTG AGG TGG TTT GGA     480
Asn Trp Asp Asp Phe Gly Gly Met Asn Gln Tyr Val Arg Trp Phe Gly
145                 150                 155                 160

GGA ACC CAT CAC GAC GAT TTC TAC AGA GAT GAG AAG ATC AAA GAA GAG     528
Gly Thr His His Asp Asp Phe Tyr Arg Asp Glu Lys Ile Lys Glu Glu
                165                 170                 175

TAC AAA AAG TAC GTC TCC TTT CTC GTA AAC CAT GTC AAT ACC TAC ACG     576
Tyr Lys Lys Tyr Val Ser Phe Leu Val Asn His Val Asn Thr Tyr Thr
            180                 185                 190

GGA GTT CCT TAC AGG GAA GAG CCC ACC ATC ATG GCC TGG GAG CTT GCA     624
Gly Val Pro Tyr Arg Glu Glu Pro Thr Ile Met Ala Trp Glu Leu Ala
        195                 200                 205

AAC GAA CCG CGC TGT GAG ACG GAC AAA TCG GGG AAC ACG CTC GTT GAG     672
Asn Glu Pro Arg Cys Glu Thr Asp Lys Ser Gly Asn Thr Leu Val Glu
    210                 215                 220
```

FIG. 11a

THERMOTOGA MARITINA β - MANNANASE (CONTINUED) (6GP2)

```
TGG GTG AAG GAG ATG AGC TCC TAC ATA AAG AGT CTG GAT CCC AAC CAC      720
Trp Val Lys Glu Met Ser Ser Tyr Ile Lys Ser Leu Asp Pro Asn His
225                 230                 235                 240

CTC GTG GCT GTG GGG GAC GAA GGA TTC TTC AGC AAC TAC GAA GGA TTC      768
Leu Val Ala Val Gly Asp Glu Gly Phe Phe Ser Asn Tyr Glu Gly Phe
                245                 250                 255

AAA CCT TAC GGT GGA GAA GCC GAG TGG GCC TAC AAC GGC TGG TCC GGT      816
Lys Pro Tyr Gly Gly Glu Ala Glu Trp Ala Tyr Asn Gly Trp Ser Gly
            260                 265                 270

GTT GAC TGG AAG AAG CTC CTT TCG ATA GAG ACG GTG GAC TTC GGC ACG      864
Val Asp Trp Lys Lys Leu Leu Ser Ile Glu Thr Val Asp Phe Gly Thr
        275                 280                 285

TTC CAC CTC TAT CCG TCC CAC TGG GGT GTC AGT CCA GAG AAC TAT GCC      912
Phe His Leu Tyr Pro Ser His Trp Gly Val Ser Pro Glu Asn Tyr Ala
    290                 295                 300

CAG TGG GGA GCG AAG TGG ATA GAA GAC CAC ATA AAG ATC GCA AAA GAG      960
Gln Trp Gly Ala Lys Trp Ile Glu Asp His Ile Lys Ile Ala Lys Glu
305                 310                 315                 320

ATC GGA AAA CCC GTT GTT CTG GAA GAA TAT GGA ATT CCA AAG AGT GCG     1008
Ile Gly Lys Pro Val Val Leu Glu Glu Tyr Gly Ile Pro Lys Ser Ala
                325                 330                 335

CCA GTT AAC AGA ACG GCC ATC TAC AGA CTC TGG AAC GAT CTG GTC TAC     1056
Pro Val Asn Arg Thr Ala Ile Tyr Arg Leu Trp Asn Asp Leu Val Tyr
            340                 345                 350

GAT CTC GGT GGA GAT GGA GCG ATG TTC TGG ATG CTC GCG GGA ATC GGG     1104
Asp Leu Gly Gly Asp Gly Ala Met Phe Trp Met Leu Ala Gly Ile Gly
        355                 360                 365

GAA GGT TCG GAC AGA GAC GAG AGA GGG TAC TAT CCG GAC TAC GAC GGT     1152
Glu Gly Ser Asp Arg Asp Glu Arg Gly Tyr Tyr Pro Asp Tyr Asp Gly
    370                 375                 380

TTC AGA ATA GTG AAC GAC GAC AGT CCA GAA GCG GAA CTG ATA AGA GAA     1200
Phe Arg Ile Val Asn Asp Asp Ser Pro Glu Ala Glu Leu Ile Arg Glu
385                 390                 395                 400

TAC GCG AAG CTG TTC AAC ACA GGT GAA GAC ATA AGA GAA GAC ACC TGC     1248
Tyr Ala Lys Leu Phe Asn Thr Gly Glu Asp Ile Arg Glu Asp Thr Cys
                405                 410                 415

TCT TTC ATC CTT CCA AAA GAC GGC ATG GAG ATC AAA AAG ACC GTG GAA     1296
Ser Phe Ile Leu Pro Lys Asp Gly Met Glu Ile Lys Lys Thr Val Glu
            420                 425                 430

GTG AGG GCT GGT GTT TTC GAC TAC AGC AAC ACG TTT GAA AAG TTG TCT     1344
Val Arg Ala Gly Val Phe Asp Tyr Ser Asn Thr Phe Glu Lys Leu Ser
        435                 440                 445
```

FIG. 11b

THERMOTOGA MARITINA β - MANNANASE (CONTINUED) (6GP2)

```
GTC AAA GTC GAA GAT CTG GTT TTT GAA AAT GAG ATA GAG CAT CTC GGA   1392
Val Lys Val Glu Asp Leu Val Phe Glu Asn Glu Ile Glu His Leu Gly
    450                 455                 460

TAC GGA ATT TAC GGC TTT GAT CTC GAC ACA ACC CGG ATC CCG GAT GGA   1440
Tyr Gly Ile Tyr Gly Phe Asp Leu Asp Thr Thr Arg Ile Pro Asp Gly
465                 470                 475                 480

GAA CAT GAA ATG TTC CTT GAA GGC CAC TTT CAG GGA AAA ACG GTG AAA   1488
Glu His Glu Met Phe Leu Glu Gly His Phe Gln Gly Lys Thr Val Lys
                485                 490                 495

GAC TCT ATC AAA GCG AAA GTG GTG AAC GAA GCA CGG TAC GTG CTC GCA   1536
Asp Ser Ile Lys Ala Lys Val Val Asn Glu Ala Arg Tyr Val Leu Ala
            500                 505                 510

GAG GAA GTT GAT TTT TCC TCT CCA GAA GAG GTG AAA AAC TGG TGG AAC   1584
Glu Glu Val Asp Phe Ser Ser Pro Glu Glu Val Lys Asn Trp Trp Asn
        515                 520                 525

AGC GGA ACC TGG CAG GCA GAG TTC GGG TCA CCT GAC ATT GAA TGG AAC   1632
Ser Gly Thr Trp Gln Ala Glu Phe Gly Ser Pro Asp Ile Glu Trp Asn
    530                 535                 540

GGT GAG GTG GGA AAT GGA GCA CTG CAG CTG AAC GTG AAA CTG CCC GGA   1680
Gly Glu Val Gly Asn Gly Ala Leu Gln Leu Asn Val Lys Leu Pro Gly
545                 550                 555                 560

AAG AGC GAC TGG GAA GAA GTG AGA GTA GCA AGG AAG TTC GAA AGA CTC   1728
Lys Ser Asp Trp Glu Glu Val Arg Val Ala Arg Lys Phe Glu Arg Leu
                565                 570                 575

TCA GAA TGT GAG ATC CTC GAG TAC GAC ATC TAC ATT CCA AAC GTC GAG   1776
Ser Glu Cys Glu Ile Leu Glu Tyr Asp Ile Tyr Ile Pro Asn Val Glu
            580                 585                 590

GGA CTC AAG GGA AGG TTG AGG CCG TAC GCG GTT CTG AAC CCC GGC TGG   1824
Gly Leu Lys Gly Arg Leu Arg Pro Tyr Ala Val Leu Asn Pro Gly Trp
        595                 600                 605

GTG AAG ATA GGC CTC GAC ATG AAC AAC GCG AAC GTG GAA AGT GCG GAG   1872
Val Lys Ile Gly Leu Asp Met Asn Asn Ala Asn Val Glu Ser Ala Glu
    610                 615                 620

ATC ATC ACT TTC GGC GGA AAA GAG TAC AGA AGA TTC CAT GTA AGA ATT   1920
Ile Ile Thr Phe Gly Gly Lys Glu Tyr Arg Arg Phe His Val Arg Ile
625                 630                 635                 640

GAG TTC GAC AGA ACA GCG GGG GTG AAA GAA CTT CAC ATA GGA GTT GTC   1968
Glu Phe Asp Arg Thr Ala Gly Val Lys Glu Leu His Ile Gly Val Val
                645                 650                 655

GGT GAT CAT CTG AGG TAC GAT GGA CCG ATT TTC ATC GAT AAT GTG AGA   2016
Gly Asp His Leu Arg Tyr Asp Gly Pro Ile Phe Ile Asp Asn Val Arg
            660                 665                 670

CTT TAT AAA AGA ACA GGA GGT ATG TGA                               2043
Leu Tyr Lys Arg Thr Gly Gly Met
        675                 680
```

FIG. 11c

AEPII 1a β-MANNOSIDASE (63GB1)

```
ATG CTA CCA GAA GAG TTC CTA TGG GGC GTT GGG CAG TCA GGC TTT CAG       48
Met Leu Pro Glu Glu Phe Leu Trp Gly Val Gly Gln Ser Gly Phe Gln
  1               5                  10                  15

TTC GAA ATG GGC GAC AAG CTC AGG AGG CAC ATC GAT CCA AAT ACC GAC       96
Phe Glu Met Gly Asp Lys Leu Arg Arg His Ile Asp Pro Asn Thr Asp
             20                  25                  30

TGG TGG AAG TGG GTT CGC GAT CCT TTC AAC ATA AAA AAG GAG CTT GTG      144
Trp Trp Lys Trp Val Arg Asp Pro Phe Asn Ile Lys Lys Glu Leu Val
         35                  40                  45

AGT GGG GAC CTT CCC GAG GAC GGC ATC AAC AAC TAC GAA CTT TTT GAA      192
Ser Gly Asp Leu Pro Glu Asp Gly Ile Asn Asn Tyr Glu Leu Phe Glu
     50                  55                  60

AAC GAT CAC AAG CTC GCT AAA GGC CTT GGA CTC AAC GCA TAC AGG ATT      240
Asn Asp His Lys Leu Ala Lys Gly Leu Gly Leu Asn Ala Tyr Arg Ile
 65                  70                  75                  80

GGA ATA GAG TGG AGC AGA ATC TTT CCC TGG CCG ACG TGG ACG GTC GAT      288
Gly Ile Glu Trp Ser Arg Ile Phe Pro Trp Pro Thr Trp Thr Val Asp
                 85                  90                  95

ACC GAG GTC GAG TTC GAC ACT TAC GGT TTA GTA AAG GAC GTT AAG ATA      336
Thr Glu Val Glu Phe Asp Thr Tyr Gly Leu Val Lys Asp Val Lys Ile
            100                 105                 110

GAC AAG TCC ACC CTT GCT GAA CTC GAC AGG CTG GCC AAC AAG GAG GAG      384
Asp Lys Ser Thr Leu Ala Glu Leu Asp Arg Leu Ala Asn Lys Glu Glu
        115                 120                 125

GTA ATG TAC TAC AGG CGC GTT ATT CAG CAT TTG AGG GAG CTC GGC TTC      432
Val Met Tyr Tyr Arg Arg Val Ile Gln His Leu Arg Glu Leu Gly Phe
    130                 135                 140

AAG GTC TTC GTT AAC CTC AAC CAC TTC ACG CTT CCA ATA TGG CTC CAC      480
Lys Val Phe Val Asn Leu Asn His Phe Thr Leu Pro Ile Trp Leu His
145                 150                 155                 160

GAC CCG ATA GTG GCA AGG GAG AAG GCC CTC ACA AAC GAC AGA ATC GGC      528
Asp Pro Ile Val Ala Arg Glu Lys Ala Leu Thr Asn Asp Arg Ile Gly
                165                 170                 175

TGG GTC TCC CAG AGG ACA GTT GTT GAG TTT GCC AAG TAT GCT GCT TAC      576
Trp Val Ser Gln Arg Thr Val Val Glu Phe Ala Lys Tyr Ala Ala Tyr
            180                 185                 190

ATC GCC CAT GCG CTC GGA GAC CTC GTG GAC ACA TGG AGC ACC TTC AAC      624
Ile Ala His Ala Leu Gly Asp Leu Val Asp Thr Trp Ser Thr Phe Asn
        195                 200                 205

GAA CCT ATG GTA GTT GTG GAG CTC GGC TAC CTC GCC CCC TAC TCA GGA      672
Glu Pro Met Val Val Val Glu Leu Gly Tyr Leu Ala Pro Tyr Ser Gly
    210                 215                 220

TTT CCC CCG GGA GTC ATG AAC CCC GAG GCC GCG AAG CTG GCG ATC CTC      720
Phe Pro Pro Gly Val Met Asn Pro Glu Ala Ala Lys Leu Ala Ile Leu
225                 230                 235                 240

AAC ATG ATA AAC GCC CAC GCC TTG GCA TAT AAG ATG ATA AAG AGG TTC      768
Asn Met Ile Asn Ala His Ala Leu Ala Tyr Lys Met Ile Lys Arg Phe
                245                 250                 255
```

FIG. 12a

AEPII 1a β-MANNOSIDASE (63GB1)(CONTINUED)

```
GAC ACC AAG AAG GCC GAT GAG GAT AGC AAG TCC CCT GCG GAC GTT GGC     816
Asp Thr Lys Lys Ala Asp Glu Asp Ser Lys Ser Pro Ala Asp Val Gly
            260                 265                 270

ATA ATT TAC AAC AAC ATC GGT GTT GCC TAC CCT AAA GAC CCT AAC GAT     864
Ile Ile Tyr Asn Asn Ile Gly Val Ala Tyr Pro Lys Asp Pro Asn Asp
        275                 280                 285

CCC AAG GAC GTT AAA GCA GCC GAA AAC GAC AAC TAC TTC CAC AGC GGA     912
Pro Lys Asp Val Lys Ala Ala Glu Asn Asp Asn Tyr Phe His Ser Gly
    290                 295                 300

CTG TTC TTT GAT GCC ATC CAC AAG GGT AAG CTC AAC ATA GAG TTC GAC     960
Leu Phe Phe Asp Ala Ile His Lys Gly Lys Leu Asn Ile Glu Phe Asp
305                 310                 315                 320

GGC GAA AAC TTT GTA AAA GTT AGA CAC CTA AAA GGC AAT GAC TGG ATA    1008
Gly Glu Asn Phe Val Lys Val Arg His Leu Lys Gly Asn Asp Trp Ile
                325                 330                 335

GGC CTC AAC TAC TAC ACC CGC GAG GTT GTT AGA TAT TCG GAG CCC AAG    1056
Gly Leu Asn Tyr Tyr Thr Arg Glu Val Val Arg Tyr Ser Glu Pro Lys
            340                 345                 350

TTC CCA AGT ATA CCC CTC ATA TCC TTC AAG GGC GTT CCC AAC TAC GGC    1104
Phe Pro Ser Ile Pro Leu Ile Ser Phe Lys Gly Val Pro Asn Tyr Gly
        355                 360                 365

TAC TCC TGC AGG CCC GGC ACG ACC TCC GCC GAT GGC ATG CCC GTC AGC    1152
Tyr Ser Cys Arg Pro Gly Thr Thr Ser Ala Asp Gly Met Pro Val Ser
    370                 375                 380

GAT ATC GGC TGG GAA GTC TAT CCC CAG GGA ATC TAC GAC TCG ATA GTC    1200
Asp Ile Gly Trp Glu Val Tyr Pro Gln Gly Ile Tyr Asp Ser Ile Val
385                 390                 395                 400

GAG GCC ACC AAG TAC AGT GTT CCT GTT TAC GTC ACC GAG AAC GGT GTT    1248
Glu Ala Thr Lys Tyr Ser Val Pro Val Tyr Val Thr Glu Asn Gly Val
                405                 410                 415

GCG GAT TCC GCG GAC ACG CTG AGG CCA TAC TAC ATA GTC AGC CAC GTC    1296
Ala Asp Ser Ala Asp Thr Leu Arg Pro Tyr Tyr Ile Val Ser His Val
            420                 425                 430

TCA AAG ATA GAG GAA GCC ATT GAG AAT GGA TAC CCC GTA AAA GGC TAC    1344
Ser Lys Ile Glu Glu Ala Ile Glu Asn Gly Tyr Pro Val Lys Gly Tyr
        435                 440                 445

ATG TAC TGG GCG CTT ACG GAT AAC TAC GAG TGG GCC CTC GGC TTC AGC    1392
Met Tyr Trp Ala Leu Thr Asp Asn Tyr Glu Trp Ala Leu Gly Phe Ser
    450                 455                 460

ATG AGG TTT GGT CTC TAC AAG GTC GAC CTC ATC TCC AAG GAG AGG ATC    1440
Met Arg Phe Gly Leu Tyr Lys Val Asp Leu Ile Ser Lys Glu Arg Ile
465                 470                 475                 480

CCG AGG GAG AGA AGC GTT GAG ATA TAT CGC AGG ATA GTG CAG TCC AAC    1488
Pro Arg Glu Arg Ser Val Glu Ile Tyr Arg Arg Ile Val Gln Ser Asn
                485                 490                 495

GGT GTT CCT AAG GAT ATC AAA GAG GAG TTC CTG AAG GGT GAG GAG AAA    1536
Gly Val Pro Lys Asp Ile Lys Glu Glu Phe Leu Lys Gly Glu Glu Lys
            500                 505                 510

TGA                                                                1539
```

FIG. 12b

OC1/4V ENDOGLUCANASE (33GP1)

```
ATG GTA GAA AGA CAC TTC AGA TAT GTT CTT ATT TGC ACC CTG TTT CTT      48
Met Val Glu Arg His Phe Arg Tyr Val Leu Ile Cys Thr Leu Phe Leu
  1               5                  10                  15

GTT ATG CTC CTA ATC TCA TCC ACT CAG TGT GGA AAA AAT GAA CCA AAC      96
Val Met Leu Leu Ile Ser Ser Thr Gln Cys Gly Lys Asn Glu Pro Asn
             20                  25                  30

AAA AGA GTG AAT AGC ATG GAA CAG TCA GTT GCT GAA AGT GAT AGC AAC     144
Lys Arg Val Asn Ser Met Glu Gln Ser Val Ala Glu Ser Asp Ser Asn
         35                  40                  45

TCA GCA TTT GAA TAC AAC AAA ATG GTA GGT AAA GGA GTA AAT ATT GGA     192
Ser Ala Phe Glu Tyr Asn Lys Met Val Gly Lys Gly Val Asn Ile Gly
     50                  55                  60

AAT GCT TTA GAA GCT CCT TTC GAA GGA GCT TGG GGA GTA AGA ATT GAG     240
Asn Ala Leu Glu Ala Pro Phe Glu Gly Ala Trp Gly Val Arg Ile Glu
 65                  70                  75                  80

GAT GAA TAT TTT GAG ATA ATA AAG AAA AGG GGA TTT GAT TCT GTT AGG     288
Asp Glu Tyr Phe Glu Ile Ile Lys Lys Arg Gly Phe Asp Ser Val Arg
                 85                  90                  95

ATT CCC ATA AGA TGG TCA GCA CAT ATA TCC GAA AAG CCA CCA TAT GAT     336
Ile Pro Ile Arg Trp Ser Ala His Ile Ser Glu Lys Pro Pro Tyr Asp
            100                 105                 110

ATT GAC AGG AAT TTC CTC GAA AGA GTT AAC CAT GTT GTC GAT AGG GCT     384
Ile Asp Arg Asn Phe Leu Glu Arg Val Asn His Val Val Asp Arg Ala
        115                 120                 125

CTT GAG AAT AAT TTA ACA GTA ATC ATC AAT ACG CAC CAT TTT GAA GAA     432
Leu Glu Asn Asn Leu Thr Val Ile Ile Asn Thr His His Phe Glu Glu
    130                 135                 140

CTC TAT CAA GAA CCG GAT AAA TAC GGC GAT GTT TTG GTG GAA ATT TGG     480
Leu Tyr Gln Glu Pro Asp Lys Tyr Gly Asp Val Leu Val Glu Ile Trp
145                 150                 155                 160

AGA CAG ATT GCA AAA TTC TTT AAA GAT TAC CCG GAA AAT CTG TTC TTT     528
Arg Gln Ile Ala Lys Phe Phe Lys Asp Tyr Pro Glu Asn Leu Phe Phe
                165                 170                 175

GAA ATC TAC AAC GAG CCT GCT CAG AAC TTG ACA GCT GAA AAA TGG AAC     576
Glu Ile Tyr Asn Glu Pro Ala Gln Asn Leu Thr Ala Glu Lys Trp Asn
            180                 185                 190

GCA CTT TAT CCA AAA GTG CTC AAA GTT ATC AGG GAG AGC AAT CCA ACC     624
Ala Leu Tyr Pro Lys Val Leu Lys Val Ile Arg Glu Ser Asn Pro Thr
        195                 200                 205

CGG ATT GTC ATT ATC GAT GCT CCA AAC TGG GCA CAC TAT AGC GCA GTG     672
Arg Ile Val Ile Ile Asp Ala Pro Asn Trp Ala His Tyr Ser Ala Val
    210                 215                 220
```

FIG. 13a

OC1/4V ENDOGLUCANASE (33GP1)(CONTINUED)

```
AGA AGT CTA AAA TTA GTC AAC GAC AAA CGC ATC ATT GTT TCC TTC CAT      720
Arg Ser Leu Lys Leu Val Asn Asp Lys Arg Ile Ile Val Ser Phe His
225                 230                 235                 240

TAC TAC GAA CCT TTC AAA TTC ACA CAT CAG GGT GCC GAA TGG GTT AAT      768
Tyr Tyr Glu Pro Phe Lys Phe Thr His Gln Gly Ala Glu Trp Val Asn
                245                 250                 255

CCC ATC CCA CCT GTT AGG GTT AAG TGG AAT GGC GAG GAA TGG GAA ATT      816
Pro Ile Pro Pro Val Arg Val Lys Trp Asn Gly Glu Glu Trp Glu Ile
            260                 265                 270

AAC CAA ATC AGA AGT CAT TTC AAA TAC GTG AGT GAC TGG GCA AAG CAA      864
Asn Gln Ile Arg Ser His Phe Lys Tyr Val Ser Asp Trp Ala Lys Gln
        275                 280                 285

AAT AAC GTA CCA ATC TTT CTT GGT GAA TTC GGT GCT TAT TCA AAA GCA      912
Asn Asn Val Pro Ile Phe Leu Gly Glu Phe Gly Ala Tyr Ser Lys Ala
    290                 295                 300

GAC ATG GAC TCA AGG GTT AAG TGG ACC GAA AGT GTG AGA AAA ATG GCG      960
Asp Met Asp Ser Arg Val Lys Trp Thr Glu Ser Val Arg Lys Met Ala
305                 310                 315                 320

GAA GAA TTT GGA TTT TCA TAC GCG TAT TGG GAA TTT TGT GCA GGA TTT     1008
Glu Glu Phe Gly Phe Ser Tyr Ala Tyr Trp Glu Phe Cys Ala Gly Phe
                325                 330                 335

GGC ATA TAC GAT AGA TGG TCT CAA AAC TGG ATC GAA CCA TTG GCA ACA     1056
Gly Ile Tyr Asp Arg Trp Ser Gln Asn Trp Ile Glu Pro Leu Ala Thr
            340                 345                 350

GCT GTG GTT GGC ACA GGC AAA GAG TAA                                 1083
Ala Val Val Gly Thr Gly Lys Glu
        355                 360
```

FIG. 13b

THERMOTOGA MARITIMA PULLULANASE (6GP3)

```
ATG GAT CTT ACA AAG GTG GGG ATC ATA GTG AGG CTG AAC GAG TGG CAG       48
Met Asp Leu Thr Lys Val Gly Ile Ile Val Arg Leu Asn Glu Trp Gln
  1               5                  10                  15

GCA AAA GAC GTG GCA AAA GAC AGG TTC ATA GAG ATA AAA GAC GGA AAG       96
Ala Lys Asp Val Ala Lys Asp Arg Phe Ile Glu Ile Lys Asp Gly Lys
             20                  25                  30

GCT GAA GTG TGG ATA CTC CAG GGA GTG GAA GAG ATT TTC TAC GAA AAA      144
Ala Glu Val Trp Ile Leu Gln Gly Val Glu Glu Ile Phe Tyr Glu Lys
         35                  40                  45

CCA GAC ACA TCT CCC AGA ATC TTC TTC GCA CAG GCA AGG TCG AAC AAG      192
Pro Asp Thr Ser Pro Arg Ile Phe Phe Ala Gln Ala Arg Ser Asn Lys
     50                  55                  60

GTG ATC GAG GCT TTT CTG ACC AAT CCT GTG GAT ACG AAA AAG AAA GAA      240
Val Ile Glu Ala Phe Leu Thr Asn Pro Val Asp Thr Lys Lys Lys Glu
 65                  70                  75                  80

CTC TTC AAG GTT ACT GTT GAC GGA AAA GAG ATT CCC GTC TCA AGA GTG      288
Leu Phe Lys Val Thr Val Asp Gly Lys Glu Ile Pro Val Ser Arg Val
                 85                  90                  95

GAA AAG GCC GAT CCC ACG GAC ATA GAC GTG ACG AAC TAC GTG AGA ATC      336
Glu Lys Ala Asp Pro Thr Asp Ile Asp Val Thr Asn Tyr Val Arg Ile
            100                 105                 110

GTC CTT TCT GAA TCC CTG AAA GAA GAA GAC CTC AGA AAA GAC GTG GAA      384
Val Leu Ser Glu Ser Leu Lys Glu Glu Asp Leu Arg Lys Asp Val Glu
        115                 120                 125

CTG ATC ATA GAA GGT TAC AAA CCG GCA AGA GTC ATC ATG ATG GAG ATC      432
Leu Ile Ile Glu Gly Tyr Lys Pro Ala Arg Val Ile Met Met Glu Ile
    130                 135                 140

CTG GAC GAC TAC TAT TAC GAT GGA GAG CTC GGA GCC GTA TAT TCT CCA      480
Leu Asp Asp Tyr Tyr Tyr Asp Gly Glu Leu Gly Ala Val Tyr Ser Pro
145                 150                 155                 160

GAG AAG ACG ATA TTC AGA GTC TGG TCC CCC GTT TCT AAG TGG GTA AAG      528
Glu Lys Thr Ile Phe Arg Val Trp Ser Pro Val Ser Lys Trp Val Lys
                165                 170                 175

GTG CTT CTC TTC AAA AAC GGA GAA GAC ACA GAA CCG TAC CAG GTT GTG      576
Val Leu Leu Phe Lys Asn Gly Glu Asp Thr Glu Pro Tyr Gln Val Val
            180                 185                 190

AAC ATG GAA TAC AAG GGA AAC GGG GTC TGG GAA GCG GTT GTT GAA GGC      624
Asn Met Glu Tyr Lys Gly Asn Gly Val Trp Glu Ala Val Val Glu Gly
        195                 200                 205

GAT CTC GAC GGA GTG TTC TAC CTC TAT CAG CTG GAA AAC TAC GGA AAG      672
Asp Leu Asp Gly Val Phe Tyr Leu Tyr Gln Leu Glu Asn Tyr Gly Lys
    210                 215                 220
```

FIG. 14a

THERMOTOGA MARITIMA PULLULANASE (6GP3)(continued)

```
ATC AGA ACA ACC GTC GAT CCT TAT TCG AAA GCG GTT TAC GCA AAC AAC      720
Ile Arg Thr Thr Val Asp Pro Tyr Ser Lys Ala Val Tyr Ala Asn Asn
225                 230                 235                 240

CAA GAG AGC GCC GTT GTG AAT CTT GCC AGG ACA AAC CCA GAA GGA TGG      768
Gln Glu Ser Ala Val Val Asn Leu Ala Arg Thr Asn Pro Glu Gly Trp
                245                 250                 255

GAA AAC GAC AGG GGA CCG AAA ATC GAA GGA TAC GAA GAC GCG ATA ATC      816
Glu Asn Asp Arg Gly Pro Lys Ile Glu Gly Tyr Glu Asp Ala Ile Ile
            260                 265                 270

TAT GAA ATA CAC ATA GCG GAC ATC ACA GGA CTC GAA AAC TCC GGG GTA      864
Tyr Glu Ile His Ile Ala Asp Ile Thr Gly Leu Glu Asn Ser Gly Val
        275                 280                 285

AAA AAC AAA GGC CTC TAT CTC GGG CTC ACC GAA GAA AAC ACG AAA GGA      912
Lys Asn Lys Gly Leu Tyr Leu Gly Leu Thr Glu Glu Asn Thr Lys Gly
    290                 295                 300

CCG GGC GGT GTG ACA ACA GGC CTT TCG CAC CTT GTG GAA CTC GGT GTT      960
Pro Gly Gly Val Thr Thr Gly Leu Ser His Leu Val Glu Leu Gly Val
305                 310                 315                 320

ACA CAC GTT CAT ATA CTT CCT TTC TTT GAT TTC TAC ACA GGC GAC GAA     1008
Thr His Val His Ile Leu Pro Phe Phe Asp Phe Tyr Thr Gly Asp Glu
                325                 330                 335

CTC GAT AAA GAT TTC GAG AAG TAC TAC AAC TGG GGT TAC GAT CCT TAC     1056
Leu Asp Lys Asp Phe Glu Lys Tyr Tyr Asn Trp Gly Tyr Asp Pro Tyr
            340                 345                 350

CTG TTC ATG GTT CCG GAG GGC AGA TAC TCA ACC GAT CCC AAA AAC CCA     1104
Leu Phe Met Val Pro Glu Gly Arg Tyr Ser Thr Asp Pro Lys Asn Pro
        355                 360                 365

CAC ACG AGA ATC AGA GAA GTC AAA GAA ATG GTC AAA GCC CTT CAC AAA     1152
His Thr Arg Ile Arg Glu Val Lys Glu Met Val Lys Ala Leu His Lys
    370                 375                 380

CAC GGT ATA GGT GTG ATT ATG GAC ATG GTG TTC CCT CAC ACC TAC GGT     1200
His Gly Ile Gly Val Ile Met Asp Met Val Phe Pro His Thr Tyr Gly
385                 390                 395                 400

ATA GGC GAA CTC TCT GCG TTC GAT CAG ACG GTG CCG TAC TAC TTC TAC     1248
Ile Gly Glu Leu Ser Ala Phe Asp Gln Thr Val Pro Tyr Tyr Phe Tyr
                405                 410                 415

AGA ATC GAC AAG ACA GGT GCC TAT TTG AAC GAA AGC GGA TGT GGT AAC     1296
Arg Ile Asp Lys Thr Gly Ala Tyr Leu Asn Glu Ser Gly Cys Gly Asn
            420                 425                 430

GTC ATC GCA AGC GAA AGA CCC ATG ATG AGA AAA TTC ATA GTC GAT ACC     1344
Val Ile Ala Ser Glu Arg Pro Met Met Arg Lys Phe Ile Val Asp Thr
        435                 440                 445
```

FIG. 14b

THERMOTOGA MARITIMA PULLULANASE (6GP3)(continued)

```
GTC ACC TAC TGG GTA AAG GAG TAT CAC ATA GAC GGA TTC AGG TTC GAT    1392
Val Thr Tyr Trp Val Lys Glu Tyr His Ile Asp Gly Phe Arg Phe Asp
    450                 455                 460

CAG ATG GGT CTC ATC GAC AAA AAG ACA ATG CTC GAA GTC GAA AGA GCT    1440
Gln Met Gly Leu Ile Asp Lys Lys Thr Met Leu Glu Val Glu Arg Ala
465                 470                 475                 480

CTT CAT AAA ATC GAT CCA ACT ATC ATT CTC TAC GGC GAA CCG TGG GGT    1488
Leu His Lys Ile Asp Pro Thr Ile Ile Leu Tyr Gly Glu Pro Trp Gly
                485                 490                 495

GGA TGG GGA GCA CCG ATC AGG TTT GGA AAG AGC GAT GTC GCC GGC ACA    1536
Gly Trp Gly Ala Pro Ile Arg Phe Gly Lys Ser Asp Val Ala Gly Thr
            500                 505                 510

CAC GTG GCA GCT TTC AAC GAT GAG TTC AGA GAC GCA ATA AGG GGT TCC    1584
His Val Ala Ala Phe Asn Asp Glu Phe Arg Asp Ala Ile Arg Gly Ser
        515                 520                 525

GTG TTC AAC CCG AGC GTC AAG GGA TTC GTC ATG GGA GGA TAC GGA AAG    1632
Val Phe Asn Pro Ser Val Lys Gly Phe Val Met Gly Gly Tyr Gly Lys
    530                 535                 540

GAA ACC AAG ATC AAA AGG GGT GTT GTT GGA AGC ATA AAC TAC GAC GGA    1680
Glu Thr Lys Ile Lys Arg Gly Val Val Gly Ser Ile Asn Tyr Asp Gly545
550                 555                 560

AAA CTC ATC AAA AGT TTC GCC CTT GAT CCA GAA GAA ACT ATA AAC TAC    1728
Lys Leu Ile Lys Ser Phe Ala Leu Asp Pro Glu Glu Thr Ile Asn Tyr
                565                 570                 575

GCA GCG TGT CAC GAC AAC CAC ACA CTG TGG GAC AAG AAC TAC CTT GCC    1776
Ala Ala Cys His Asp Asn His Thr Leu Trp Asp Lys Asn Tyr Leu Ala
            580                 585                 590

GCC AAA GCT GAT AAG AAA AAG GAA TGG ACC GAA GAA GAA CTG AAA AAC    1824
Ala Lys Ala Asp Lys Lys Lys Glu Trp Thr Glu Glu Glu Leu Lys Asn
        595                 600                 605

GCC CAG AAA CTG GCT GGT GCG ATA CTT CTC ACT TCT CAA GGT GTT CCT    1872
Ala Gln Lys Leu Ala Gly Ala Ile Leu Leu Thr Ser Gln Gly Val Pro
    610                 615                 620

TTC CTC CAC GGA GGG CAG GAC TTC TGC AGG ACG ACG AAT TTC AAC GAC    1920
Phe Leu His Gly Gly Gln Asp Phe Cys Arg Thr Thr Asn Phe Asn Asp
625                 630                 635                 640

AAC TCC TAC AAC GCC CCT ATC TCG ATA AAC GGC TTC GAT TAC GAA AGA    1968
Asn Ser Tyr Asn Ala Pro Ile Ser Ile Asn Gly Phe Asp Tyr Glu Arg
                645                 650                 655

AAA CTT CAG TTC ATA GAC GTG TTC AAT TAC CAC AAG GGT CTC ATA AAA    2016
Lys Leu Gln Phe Ile Asp Val Phe Asn Tyr His Lys Gly Leu Ile Lys
            660                 665                 670
```

FIG. 14c

THERMOTOGA MARITIMA PULLULANASE (6GP3)(continued)

```
CTC AGA AAA GAA CAC CCT GCT TTC AGG CTG AAA AAC GCT GAA GAG ATC    2064
Leu Arg Lys Glu His Pro Ala Phe Arg Leu Lys Asn Ala Glu Glu Ile
        675                 680                 685

AAA AAA CAC CTG GAA TTT CTC CCG GGC GGG AGA AGA ATA GTT GCG TTC    2112
Lys Lys His Leu Glu Phe Leu Pro Gly Gly Arg Arg Ile Val Ala Phe
    690                 695                 700

ATG CTT AAA GAC CAC GCA GGT GGT GAT CCC TGG AAA GAC ATC GTG GTG    2160
Met Leu Lys Asp His Ala Gly Gly Asp Pro Trp Lys Asp Ile Val Val
705                 710                 715                 720

ATT TAC AAT GGA AAC TTA GAG AAG ACA ACA TAC AAA CTG CCA GAA GGA    2208
Ile Tyr Asn Gly Asn Leu Glu Lys Thr Thr Tyr Lys Leu Pro Glu Gly
                725                 730                 735

AAA TGG AAT GTG GTT GTG AAC AGC CAG AAA GCC GGA ACA GAA GTG ATA    2256
Lys Trp Asn Val Val Val Asn Ser Gln Lys Ala Gly Thr Glu Val Ile
            740                 745                 750

GAA ACC GTC GAA GGA ACA ATA GAA CTC GAT CCG CTT TCC GCG TAC GTT    2304
Glu Thr Val Glu Gly Thr Ile Glu Leu Asp Pro Leu Ser Ala Tyr Val
        755                 760                 765

CTG TAC AGA GAG TGA                                                2319
Leu Tyr Arg Glu
    770
```

FIG. 14d

THERMOTOGA MARITIMA MSB8 (CLONE #6GP2) GLYCOSIDASE

```
CTT TTA TTG ATC GTT GAG CTC TCT TTC GTT CTC TTT GCA AGT GAC GAG      48
Leu Leu Leu Ile Val Glu Leu Ser Phe Val Leu Phe Ala Ser Asp Glu
  1               5                  10                  15

TTC GTG AAA GTG GAA AAC GGA AAA TTC GCT CTG AAC GGA AAA GAA TTC      96
Phe Val Lys Val Glu Asn Gly Lys Phe Ala Leu Asn Gly Lys Glu Phe
              20                  25                  30

AGA TTC ATT GGA AGC AAC AAC TAC TAC ATG CAC TAC AAG AGC AAC GGA     144
Arg Phe Ile Gly Ser Asn Asn Tyr Tyr Met His Tyr Lys Ser Asn Gly
          35                  40                  45

ATG ATA GAC AGT GTT CTG GAG AGT GCC AGA GAC ATG GGT ATA AAG GTC     192
Met Ile Asp Ser Val Leu Glu Ser Ala Arg Asp Met Gly Ile Lys Val
     50                  55                  60

CTC AGA ATC TGG GGT TTC CTC GAC GGG GAG AGT TAC TGC AGA GAC AAG     240
Leu Arg Ile Trp Gly Phe Leu Asp Gly Glu Ser Tyr Cys Arg Asp Lys
 65                  70                  75                  80

AAC ACC TAC ATG CAT CCT GAG CCC GGT GTT TTC GGG GTG CCA GAA GGA     288
Asn Thr Tyr Met His Pro Glu Pro Gly Val Phe Gly Val Pro Glu Gly
                 85                  90                  95

ATA TCG AAC GCC CAG AGC GGT TTC GAA AGA CTC GAC TAC ACA GTT GCG     336
Ile Ser Asn Ala Gln Ser Gly Phe Glu Arg Leu Asp Tyr Thr Val Ala
            100                 105                 110

AAA GCG AAA GAA CTC GGT ATA AAA CTT GTC ATT GTT CTT GTG AAC AAC     384
Lys Ala Lys Glu Leu Gly Ile Lys Leu Val Ile Val Leu Val Asn Asn
        115                 120                 125

TGG GAC GAC TTC GGT GGA ATG AAC CAG TAC GTG AGG TGG TTT GGA GGA     432
Trp Asp Asp Phe Gly Gly Met Asn Gln Tyr Val Arg Trp Phe Gly Gly
    130                 135                 140

ACC CAT CAC GAC GAT TTC TAC AGA GAT GAG AAG ATC AAA GAA GAG TAC     480
Thr His His Asp Asp Phe Tyr Arg Asp Glu Lys Ile Lys Glu Glu Tyr
145                 150                 155                 160

AAA AAG TAC GTC TCC TTT CTC GTA AAC CAT GTC AAT ACC TAC ACG GGA     528
Lys Lys Tyr Val Ser Phe Leu Val Asn His Val Asn Thr Tyr Thr Gly
                165                 170                 175

GTT CCT TAC AGG GAA GAG CCC ACC ATC ATG GCC TGG GAG CTT GCA AAC     576
Val Pro Tyr Arg Glu Glu Pro Thr Ile Met Ala Trp Glu Leu Ala Asn
            180                 185                 190

GAA CCG CGC TGT GAG ACG GAC AAA TCG GGG AAC ACG CTC GTT GAG TGG     624
Glu Pro Arg Cys Glu Thr Asp Lys Ser Gly Asn Thr Leu Val Glu Trp
        195                 200                 205

GTG AAG GAG ATG AGC TCC TAC ATA AAG AGT CTG GAT CCC AAC CAC CTC     672
Val Lys Glu Met Ser Ser Tyr Ile Lys Ser Leu Asp Pro Asn His Leu
    210                 215                 220
```

FIG. 15a

```
GTG GCT GTG GGG GAC GAA GGA TTC TTC AGC AAC TAC GAA GGA TTC AAA      720
Val Ala Val Gly Asp Glu Gly Phe Phe Ser Asn Tyr Glu Gly Phe Lys
225                 230                 235                 240

CCT TAC GGT GGA GAA GCC GAG TGG GCC TAC AAC GGC TGG TCC GGT GTT      768
Pro Tyr Gly Gly Glu Ala Glu Trp Ala Tyr Asn Gly Trp Ser Gly Val
                245                 250                 255

GAC TGG AAG AAG CTC CTT TCG ATA GAG ACG GTG GAC TTC GGC ACG TTC      816
Asp Trp Lys Lys Leu Leu Ser Ile Glu Thr Val Asp Phe Gly Thr Phe
            260                 265                 270

CAC CTC TAT CCG TCC CAC TGG GGT GTC AGT CCA GAG AAC TAT GCC CAG      864
His Leu Tyr Pro Ser His Trp Gly Val Ser Pro Glu Asn Tyr Ala Gln
        275                 280                 285

TGG GGA GCG AAG TGG ATA GAA GAC CAC ATA AAG ATC GCA AAA GAG ATC      912
Trp Gly Ala Lys Trp Ile Glu Asp His Ile Lys Ile Ala Lys Glu Ile
    290                 295                 300

GGA AAA CCC GTT GTT CTG GAA GAA TAT GGA ATT CCA AAG AGT GCG CCA      960
Gly Lys Pro Val Val Leu Glu Glu Tyr Gly Ile Pro Lys Ser Ala Pro
305                 310                 315                 320

GTT AAC AGA ACG GCC ATC TAC AGA CTC TGG AAC GAT CTG GTC TAC GAT     1008
Val Asn Arg Thr Ala Ile Tyr Arg Leu Trp Asn Asp Leu Val Tyr Asp
                325                 330                 335

CTC GGT GGA GAT GGA GCG ATG TTC TGG ATG CTC GCG GGA ATC GGG GAA     1056
Leu Gly Gly Asp Gly Ala Met Phe Trp Met Leu Ala Gly Ile Gly Glu
            340                 345                 350

GGT TCG GAC AGA GAC GAG AGA GGG TAC TAT CCG GAC TAC GAC GGT TTC     1104
Gly Ser Asp Arg Asp Glu Arg Gly Tyr Tyr Pro Asp Tyr Asp Gly Phe
        355                 360                 365

AGA ATA GTG AAC GAC GAC AGT CCA GAA GCG GAA CTG ATA AGA GAA TAC     1152
Arg Ile Val Asn Asp Asp Ser Pro Glu Ala Glu Leu Ile Arg Glu Tyr
    370                 375                 380

GCG AAG CTG TTC AAC ACA GGT GAA GAC ATA AGA GAA GAC ACC TGC TCT     1200
Ala Lys Leu Phe Asn Thr Gly Glu Asp Ile Arg Glu Asp Thr Cys Ser
385                 390                 395                 400

TTC ATC CTT CCA AAA GAC GGC ATG GAG ATC AAA AAG ACC GTG GAA GTG     1248
Phe Ile Leu Pro Lys Asp Gly Met Glu Ile Lys Lys Thr Val Glu Val
                405                 410                 415

AGG GCT GGT GTT TTC GAC TAC AGC AAC ACG TTT GAA AAG TTG TCT GTC     1296
Arg Ala Gly Val Phe Asp Tyr Ser Asn Thr Phe Glu Lys Leu Ser Val
            420                 425                 430

AAA GTC GAA GAT CTG GTT TTT GAA AAT GAG ATA GAG CAT CTC GGA TAC     1344
Lys Val Glu Asp Leu Val Phe Glu Asn Glu Ile Glu His Leu Gly Tyr
        435                 440                 445

GGA ATT TAC GGC TTT GAT CTC GAC ACA ACC CGG ATC CCG GAT GGA GAA     1392
Gly Ile Tyr Gly Phe Asp Leu Asp Thr Thr Arg Ile Pro Asp Gly Glu
    450                 455                 460
```

FIG. 15b

```
CAT GAA ATG TTC CTT GAA GGC CAC TTT CAG GGA AAA ACG GTG AAA GAC     1440
His Glu Met Phe Leu Glu Gly His Phe Gln Gly Lys Thr Val Lys Asp
465                 470                 475                 480

TCT ATC AAA GCG AAA GTG GTG AAC GAA GCA CGG TAC GTG CTC GCA GAG     1488
Ser Ile Lys Ala Lys Val Val Asn Glu Ala Arg Tyr Val Leu Ala Glu
                485                 490                 495

GAA GTT GAT TTT TCC TCT CCA GAA GAG GTG AAA AAC TGG TGG AAC AGC     1536
Glu Val Asp Phe Ser Ser Pro Glu Glu Val Lys Asn Trp Trp Asn Ser
            500                 505                 510

GGA ACC TGG CAG GCA GAG TTC GGG TCA CCT GAC ATT GAA TGG AAC GGT     1584
Gly Thr Trp Gln Ala Glu Phe Gly Ser Pro Asp Ile Glu Trp Asn Gly
        515                 520                 525

GAG GTG GGA AAT GGA GCA CTG CAG CTG AAC GTG AAA CTG CCC GGA AAG     1632
Glu Val Gly Asn Gly Ala Leu Gln Leu Asn Val Lys Leu Pro Gly Lys
    530                 535                 540

AGC GAC TGG GAA GAA GTG AGA GTA GCA AGG AAG TTC GAA AGA CTC TCA     1680
Ser Asp Trp Glu Glu Val Arg Val Ala Arg Lys Phe Glu Arg Leu Ser
545                 550                 555                 560

GAA TGT GAG ATC CTC GAG TAC GAC ATC TAC ATT CCA AAC GTC GAG GGA     1728
Glu Cys Glu Ile Leu Glu Tyr Asp Ile Tyr Ile Pro Asn Val Glu Gly
                565                 570                 575

CTC AAG GGA AGG TTG AGG CCG TAC GCG GTT CTG AAC CCC GGC TGG GTG     1776
Leu Lys Gly Arg Leu Arg Pro Tyr Ala Val Leu Asn Pro Gly Trp Val
            580                 585                 590

AAG ATA GGC CTC GAC ATG AAC AAC GCG AAC GTG GAA AGT GCG GAG ATC     1824
Lys Ile Gly Leu Asp Met Asn Asn Ala Asn Val Glu Ser Ala Glu Ile
        595                 600                 605

ATC ACT TTC GGC GGA AAA GAG TAC AGA AGA TTC CAT GTA AGA ATT GAG     1872
Ile Thr Phe Gly Gly Lys Glu Tyr Arg Arg Phe His Val Arg Ile Glu
    610                 615                 620

TTC GAC AGA ACA GCG GGG GTG AAA GAA CTT CAC ATA GGA GTT GTC GGT     1920
Phe Asp Arg Thr Ala Gly Val Lys Glu Leu His Ile Gly Val Val Gly
625                 630                 635                 640

GAT CAT CTG AGG TAC GAT GGA CCG ATT TTC ATC GAT AAT GTG AGA CTT     1968
Asp His Leu Arg Tyr Asp Gly Pro Ile Phe Ile Asp Asn Val Arg Leu
                645                 650                 655

TAT AAA AGA ACA GGA GGT ATG TGA                                     1992
Tyr Lys Arg Thr Gly Gly Met
            660
```

FIG. 15c

THERMOTOGA MARITIMA MSB8 (6gb4)

```
ATG AAA AGA ATC GAC CTG AAT GGT TTC TGG AGC GTT AGG GAT AAC GAA      48
Met Lys Arg Ile Asp Leu Asn Gly Phe Trp Ser Val Arg Asp Asn Glu
 1               5                  10                  15

GGG AGA TTT TCG TTT GAA GGG ACT GTG CCA GGG GTT GTC CAG GCA GAT      96
Gly Arg Phe Ser Phe Glu Gly Thr Val Pro Gly Val Val Gln Ala Asp
            20                  25                  30
CTG GTC AGA AAA GGT CTT CTT CCA CAC CCG TAC GTT GGG ATG AAC GAA     144
Leu Val Arg Lys Gly Leu Leu Pro His Pro Tyr Val Gly Met Asn Glu
        35                  40                  45

GAT CTC TTC AAG GAA ATA GAA GAC AGA GAG TGG ATC TAC GAG AGG GAG     192
Asp Leu Phe Lys Glu Ile Glu Asp Arg Glu Trp Ile Tyr Glu Arg Glu
    50                  55                  60
TTC GAG TTC AAA GAA GAT GTG AAA GAG GGG GAA CGT GTC GAT CTC GTT     240
Phe Glu Phe Lys Glu Asp Val Lys Glu Gly Glu Arg Val Asp Leu Val
65                  70                  75                  80

TTT GAG GGC GTC GAC ACG CTG TCG GAT GTT TAT CTG AAC GGT GTT TAC     288
Phe Glu Gly Val Asp Thr Leu Ser Asp Val Tyr Leu Asn Gly Val Tyr
                85                  90                  95

CTT GGA AGC ACC GAA GAC ATG TTC ATC GAG TAT CGC TTC GAT GTC ACG     336
Leu Gly Ser Thr Glu Asp Met Phe Ile Glu Tyr Arg Phe Asp Val Thr
            100                 105                 110

AAC GTG TTG AAA GAA AAG AAT CAC CTG AAG GTG TAC ATA AAA TCT CCC     384
Asn Val Leu Lys Glu Lys Asn His Leu Lys Val Tyr Ile Lys Ser Pro
        115                 120                 125

ATC AGA GTT CCG AAA ACT CTC GAG CAG AAC TAC GGG GTC CTC GGC GGT     432
Ile Arg Val Pro Lys Thr Leu Glu Gln Asn Tyr Gly Val Leu Gly Gly
    130                 135                 140

CCT GAA GAT CCC ATC AGA GGA TAC ATA AGA AAA GCC CAG TAT TCG TAC     480
Pro Glu Asp Pro Ile Arg Gly Tyr Ile Arg Lys Ala Gln Tyr Ser Tyr
145                 150                 155                 160

GGA TGG GAC TGG GGT GCC AGA ATC GTT ACA AGC GGT ATT TGG AAA CCC     528
Gly Trp Asp Trp Gly Ala Arg Ile Val Thr Ser Gly Ile Trp Lys Pro
                165                 170                 175

GTC TAC CTC GAG GTG TAC AGG GCA CGT CTT CAG GAT TCA ACG GCT TAT     576
Val Tyr Leu Glu Val Tyr Arg Ala Arg Leu Gln Asp Ser Thr Ala Tyr
            180                 185                 190

CTG TTG GAA CTT GAG GGG AAA GAT GCC CTT GTG AGG GTG AAC GGT TTC     624
Leu Leu Glu Leu Glu Gly Lys Asp Ala Leu Val Arg Val Asn Gly Phe
        195                 200                 205

GTA CAC GGG GAA GGA AAT CTC ATT GTG GAA GTT TAT GTA AAC GGT GAA     672
Val His Gly Glu Gly Asn Leu Ile Val Glu Val Tyr Val Asn Gly Glu
    210                 215                 220

AAG ATA GGG GAG TTT CCT GTT CTT GAA AAG AAC GGA GAA AAG CTC TTC     720
Lys Ile Gly Glu Phe Pro Val Leu Glu Lys Asn Gly Glu Lys Leu Phe
225                 230                 235                 240
```

FIG. 16a

```
GAT GGA GTG TTC CAC CTG AAA GAT GTG AAA CTA TGG TAT CCG TGG AAC      768
Asp Gly Val Phe His Leu Lys Asp Val Lys Leu Trp Tyr Pro Trp Asn
                245                 250                 255

GTG GGG AAA CCG TAC CTG TAC GAT TTC GTT TTC GTG TTG AAA GAC TTA      816
Val Gly Lys Pro Tyr Leu Tyr Asp Phe Val Phe Val Leu Lys Asp Leu
            260                 265                 270

AAC GGA GAG ATC TAC AGA GAA GAA AAG AAA ATC GGT TTG AGA AGA GTC      864
Asn Gly Glu Ile Tyr Arg Glu Glu Lys Lys Ile Gly Leu Arg Arg Val
        275                 280                 285

AGA ATC GTT CAG GAG CCC GAT GAA GAA GGA AAA ACT TTC ATA TTC GAA      912
Arg Ile Val Gln Glu Pro Asp Glu Glu Gly Lys Thr Phe Ile Phe Glu
    290                 295                 300

ATC AAC GGT GAG AAA GTC TTC GCT AAG GGT GCT AAC TGG ATT CCC TCA      960
Ile Asn Gly Glu Lys Val Phe Ala Lys Gly Ala Asn Trp Ile Pro Ser
305                 310                 315                 320

GAA AAC ATC CTC ACG TGG TTG AAG GAG GAA GAT TAC GAA AAG CTC GTC     1008
Glu Asn Ile Leu Thr Trp Leu Lys Glu Glu Asp Tyr Glu Lys Leu Val
                325                 330                 335

AAA ATG GCA AGG AGT GCC AAT ATG AAC ATG CTC AGG GTC TGG GGA GGA     1056
Lys Met Ala Arg Ser Ala Asn Met Asn Met Leu Arg Val Trp Gly Gly
            340                 345                 350

GGA ATC TAC GAG AGA GAG ATC TTC TAC AGA CTC TGT GAT GAA CTC GGT     1104
Gly Ile Tyr Glu Arg Glu Ile Phe Tyr Arg Leu Cys Asp Glu Leu Gly
        355                 360                 365

ATC ATG GTG TGG CAG GAT TTC ATG TAC GCG TGT CTT GAA TAT CCG GAT     1152
Ile Met Val Trp Gln Asp Phe Met Tyr Ala Cys Leu Glu Tyr Pro Asp
    370                 375                 380

CAT CTT CCG TGG TTC AGA AAA CTC GCG AAC GAA GAG GCA AGA AAG ATT     1200
His Leu Pro Trp Phe Arg Lys Leu Ala Asn Glu Glu Ala Arg Lys Ile
385                 390                 395                 400

GTG AGA AAA CTC AGA TAC CAT CCC TCC ATT GTT CTC TGG TGC GGA AAC     1248
Val Arg Lys Leu Arg Tyr His Pro Ser Ile Val Leu Trp Cys Gly Asn
                405                 410                 415

AAC GAA AAC AAC TGG GGA TTC GAT GAA TGG GGA AAT ATG GCC AGA AAA     1296
Asn Glu Asn Asn Trp Gly Phe Asp Glu Trp Gly Asn Met Ala Arg Lys
            420                 425                 430

GTG GAT GGT ATC AAC CTC GGA AAC AGG CTC TAC CTC TTC GAT TTT CCT     1344
Val Asp Gly Ile Asn Leu Gly Asn Arg Leu Tyr Leu Phe Asp Phe Pro
        435                 440                 445

GAG ATT TGT GCC GAA GAA GAC CCG TCC ACT CCC TAT TGG CCA TCC AGT     1392
Glu Ile Cys Ala Glu Glu Asp Pro Ser Thr Pro Tyr Trp Pro Ser Ser
    450                 455                 460

CCA TAC GGC GGT GAA AAA GCG AAC AGC GAA AAG GAA GGA GAC AGG CAC     1440
Pro Tyr Gly Gly Glu Lys Ala Asn Ser Glu Lys Glu Gly Asp Arg His
465                 470                 475                 480
```

FIG. 16b

```
GTC TGG TAC GTG TGG AGT GGC TGG ATG AAC TAC GAA AAC TAC GAA AAA     1488
Val Trp Tyr Val Trp Ser Gly Trp Met Asn Tyr Glu Asn Tyr Glu Lys
                485                 490                 495

GAC ACC GGA AGG TTC ATC AGC GAG TTT GGA TTT CAG GGT GCT CCC CAT     1536
Asp Thr Gly Arg Phe Ile Ser Glu Phe Gly Phe Gln Gly Ala Pro His
            500                 505                 510

CCA GAG ACG ATA GAG TTC TTT TCA AAA CCC GAG GAA AGA GAG ATA TTC     1584
Pro Glu Thr Ile Glu Phe Phe Ser Lys Pro Glu Glu Arg Glu Ile Phe
        515                 520                 525

CAT CCC GTC ATG CTG AAG CAC AAC AAA CAG GTG GAA GGA CAG GAA AGA     1632
His Pro Val Met Leu Lys His Asn Lys Gln Val Glu Gly Gln Glu Arg
    530                 535                 540

TTG ATC AGG TTC ATA TTC GGA AAT TTT GGA AAG TGT AAA GAT TTC GAC     1680
Leu Ile Arg Phe Ile Phe Gly Asn Phe Gly Lys Cys Lys Asp Phe Asp
545                 550                 555                 560

AGT TTT GTG TAT CTG TCC CAG CTC AAC CAG GCG GAG GCG ATC AAG TTC     1728
Ser Phe Val Tyr Leu Ser Gln Leu Asn Gln Ala Glu Ala Ile Lys Phe
                565                 570                 575

GGT GTT GAA CAC TGG CGA AGC AGG AAG TAC AAA ACG GCC GGC GCT CTC     1776
Gly Val Glu His Trp Arg Ser Arg Lys Tyr Lys Thr Ala Gly Ala Leu
            580                 585                 590

TTC TGG CAG TTC AAC GAC AGC TGG CCG GTC TTC AGC TGG TCC GCA GTC     1824
Phe Trp Gln Phe Asn Asp Ser Trp Pro Val Phe Ser Trp Ser Ala Val
        595                 600                 605

GAT TAC TTC AAA AGG CCC AAA GCT CTC TAC TAC TAT GCG AGA AGA TTC     1872
Asp Tyr Phe Lys Arg Pro Lys Ala Leu Tyr Tyr Tyr Ala Arg Arg Phe
    610                 615                 620

TTC GCT GAA GTT CTA CCC GTT TTG AAG AAG AGA GAC AAC AAA ATA GAA     1920
Phe Ala Glu Val Leu Pro Val Leu Lys Lys Arg Asp Asn Lys Ile Glu
625                 630                 635                 640

CTG CTG GTG GGT GAG CGA TCT GAG GGA GAC AAA AGA AGT CTC TCT CAG     1968
Leu Leu Val Gly Glu Arg Ser Glu Gly Asp Lys Arg Ser Leu Ser Gln
                645                 650                 655

GCT TGC AGC CTA CGA GAA GAA GGG AGA AAA GGT ATT CGA AAA GAC TTA     2016
Ala Cys Ser Leu Arg Glu Glu Gly Arg Lys Gly Ile Arg Lys Asp Leu
            660                 665                 670

CAG AAC GGT ACT CCC AGC AGA CGG TGT GAG TTT GGT TGA                 2055
Gln Asn Gly Thr Pro Ser Arg Arg Cys Glu Phe Gly
        675                 680
```

FIG. 16c

BANKIA GOULDI (37gp4)

```
ATG AAA AAA AAT CTA CTA ATG TTT AAA AGG CTT ACG TAT CTA CCT TTG      48
Met Lys Lys Asn Leu Leu Met Phe Lys Arg Leu Thr Tyr Leu Pro Leu
  1               5                  10                  15

TTT TTA ATG CTG CTC TCA CTA AGT TCA GTA GCT CAA TCT CCT GTA GAA      96
Phe Leu Met Leu Leu Ser Leu Ser Ser Val Ala Gln Ser Pro Val Glu
             20                  25                  30

AAA CAT GGC CGT TTA CAA GTT GAC GGA AAC CGC ATT CTT AAT GCG TCT     144
Lys His Gly Arg Leu Gln Val Asp Gly Asn Arg Ile Leu Asn Ala Ser
         35                  40                  45

GGA GAA ATT ACG AGC TTA GCT GGT AAC AGC CTC TTT TGG AGT AAT GCT     192
Gly Glu Ile Thr Ser Leu Ala Gly Asn Ser Leu Phe Trp Ser Asn Ala
     50                  55                  60

GGA GAC ACC TCC GAT TTT TAT AAT GCA GAA ACT GTT GAT TTT TTA GCA     240
Gly Asp Thr Ser Asp Phe Tyr Asn Ala Glu Thr Val Asp Phe Leu Ala
 65                  70                  75                  80

GAA AAC TGG AAT AGC TCA CTT ATT AGA ATA GCT ATG GGC GTA AAA GAA     288
Glu Asn Trp Asn Ser Ser Leu Ile Arg Ile Ala Met Gly Val Lys Glu
                 85                  90                  95

AAT TGG GAT GGC GGA AAT GGC TAT ATT GAT AGT CCG CAG GAG CAA GAA     336
Asn Trp Asp Gly Gly Asn Gly Tyr Ile Asp Ser Pro Gln Glu Gln Glu
            100                 105                 110

GCT AAA ATT AGA AAA GTT ATT GAT GCA GCT ATT GCT AAC GGC ATA TAT     384
Ala Lys Ile Arg Lys Val Ile Asp Ala Ala Ile Ala Asn Gly Ile Tyr
        115                 120                 125

GTA ATA ATA GAC TGG CAC ACT CAC GAA GCA GAG TTA TAC ACA GAT GAG     432
Val Ile Ile Asp Trp His Thr His Glu Ala Glu Leu Tyr Thr Asp Glu
    130                 135                 140

GCT GTT GAC TTT TTT ACC AGA ATG GCA GAC CTA TAC GGA GAT ACT CCC     480
Ala Val Asp Phe Phe Thr Arg Met Ala Asp Leu Tyr Gly Asp Thr Pro
145                 150                 155                 160

AAT GTA ATG TAT GAA ATT TAT AAC GAG CCT ATA TAC CAA AGT TGG CCT     528
Asn Val Met Tyr Glu Ile Tyr Asn Glu Pro Ile Tyr Gln Ser Trp Pro
                165                 170                 175

GTT ATT AAG AAT TAT GCA GAG CAA GTA ATT GCT GGT ATA CGT TCT AAA     576
Val Ile Lys Asn Tyr Ala Glu Gln Val Ile Ala Gly Ile Arg Ser Lys
            180                 185                 190

GAC CCA GAT AAT TTA ATA ATT GTA GGT ACT AGC AAT TAT TCT CAG CAA     624
Asp Pro Asp Asn Leu Ile Ile Val Gly Thr Ser Asn Tyr Ser Gln Gln
        195                 200                 205

GTT GAT GTA GCA TCA GCA GAC CCA ATA TCT GAT ACT AAT GTG GCA TAT     672
Val Asp Val Ala Ser Ala Asp Pro Ile Ser Asp Thr Asn Val Ala Tyr
    210                 215                 220
```

FIG. 17a

```
ACT TTA CAT TTT TAT GCA GCA TTT AAC CCG CAT GAT AAC TTA AGA AAT      720
Thr Leu His Phe Tyr Ala Ala Phe Asn Pro His Asp Asn Leu Arg Asn
225                 230                 235                 240

GTA GCA CAG ACA GCA TTA GAT AAT AAT GTT GCT TTG TTT GTT ACA GAA      768
Val Ala Gln Thr Ala Leu Asp Asn Asn Val Ala Leu Phe Val Thr Glu
                245                 250                 255

TGG GGT ACA ATT TTA AAT ACC GGA CAA GGA GAA CCA GAC AAA GAA AGC      816
Trp Gly Thr Ile Leu Asn Thr Gly Gln Gly Glu Pro Asp Lys Glu Ser
            260                 265                 270

ACT AAT ACT TGG ATG GCC TTT TTG AAA GAA AAA GGT ATA AGT CAC GCT      864
Thr Asn Thr Trp Met Ala Phe Leu Lys Glu Lys Gly Ile Ser His Ala
        275                 280                 285

AAT TGG TCT TTG AGT GAC AAA GCT TTT CCT GAA ACA GGG TCT GTA GTT      912
Asn Trp Ser Leu Ser Asp Lys Ala Phe Pro Glu Thr Gly Ser Val Val
    290                 295                 300

CAA GCA GGA CAA GGT GTA TCT GGT TTA ATT AGC AAT AAA CTT ACA GCC      960
Gln Ala Gly Gln Gly Val Ser Gly Leu Ile Ser Asn Lys Leu Thr Ala
305                 310                 315                 320

TCT GGT GAA ATT GTA AAA AAC ATC ATC CAA AAC TGG GAT ACA GAG ACC     1008
Ser Gly Glu Ile Val Lys Asn Ile Ile Gln Asn Trp Asp Thr Glu Thr
                325                 330                 335

TCT ACA GGA CCT AAA ACA ACA CAA TGT AGT ACT ATA GAA TGT ATT AGA     1056
Ser Thr Gly Pro Lys Thr Thr Gln Cys Ser Thr Ile Glu Cys Ile Arg
            340                 345                 350

GCT GCA ATG GAA ACA GCA CAA GCA GGA GAT GAA ATT ATA ATT GCC CCT     1104
Ala Ala Met Glu Thr Ala Gln Ala Gly Asp Glu Ile Ile Ile Ala Pro
        355                 360                 365

GGA AAC TAC AAT TTT CAA GAC AAG ATA CAA GGT GCC TTT AAC CGT AGT     1152
Gly Asn Tyr Asn Phe Gln Asp Lys Ile Gln Gly Ala Phe Asn Arg Ser
    370                 375                 380

GTT TAC CTT TAT GGT AGT GCT AAC GGA AAC AGT ACA AAC CCT ATT ATA     1200
Val Tyr Leu Tyr Gly Ser Ala Asn Gly Asn Ser Thr Asn Pro Ile Ile
385                 390                 395                 400

TTA AGA GGC GAA AGC GCT ACA AAC CCT CCT GTT TTC TCA GGA TTA GAT     1248
Leu Arg Gly Glu Ser Ala Thr Asn Pro Pro Val Phe Ser Gly Leu Asp
                405                 410                 415

TAT AAC AAT GGC TAC CTA TTA AGT ATT GAA GGT GAT TAT TGG AAT ATT     1296
Tyr Asn Asn Gly Tyr Leu Leu Ser Ile Glu Gly Asp Tyr Trp Asn Ile
            420                 425                 430

AAA GAT ATA GAG TTT AAA ACT GGG TCT AAA GGT ATT GTT CTT GAC AAT     1344
Lys Asp Ile Glu Phe Lys Thr Gly Ser Lys Gly Ile Val Leu Asp Asn
        435                 440                 445

TCT AAT GGT AGT AAA TTA AAA AAC CTT GTT GTT CAT GAT ATT GGA GAA     1392
Ser Asn Gly Ser Lys Leu Lys Asn Leu Val Val His Asp Ile Gly Glu
    450                 455                 460
```

FIG. 17b

```
GAA GCT ATT CAC TTG CGT GAT GGA TCT AGC AAT AAT AGT ATA GAT GGT    1440
Glu Ala Ile His Leu Arg Asp Gly Ser Ser Asn Asn Ser Ile Asp Gly
465                 470                 475                 480

TGC ACT ATA TAC AAT ACA GGT AGA ACT AAA CCT GGT TTT GGT GAA GGT    1488
Cys Thr Ile Tyr Asn Thr Gly Arg Thr Lys Pro Gly Phe Gly Glu Gly
            485                 490                 495

TTA TAT GTA GGC TCA GAT AAA GGA CAA CAT GAC ACT TAT GAA AGA GCT    1536
Leu Tyr Val Gly Ser Asp Lys Gly Gln His Asp Thr Tyr Glu Arg Ala
        500                 505                 510

TGT AAC AAT AAC ACT ATT GAA AAC TGT ACC GTT GGA CCC AAT GTA ACA    1584
Cys Asn Asn Asn Thr Ile Glu Asn Cys Thr Val Gly Pro Asn Val Thr
    515                 520                 525

GCA GAA GGC GTA GAT GTT AAG GAA GGT ACA ATG AAC ACT ATT ATA AGA    1632
Ala Glu Gly Val Asp Val Lys Glu Gly Thr Met Asn Thr Ile Ile Arg
530                 535                 540

AAT TGC GTG TTT TCT GCA GAA GGA ATT TCA GGA GAA AAT AGC TCA GAT    1680
Asn Cys Val Phe Ser Ala Glu Gly Ile Ser Gly Glu Asn Ser Ser Asp
545                 550                 555                 560

GCT TTT ATT GAT TTA AAA GGA GCC TAT GGT TTT GTA TAC AGA AAC ACG    1728
Ala Phe Ile Asp Leu Lys Gly Ala Tyr Gly Phe Val Tyr Arg Asn Thr
            565                 570                 575

TTT AAT GTT GAT GGT TCT GAA GTA ATA AAT ACT GGA GTA GAC TTT TTA    1776
Phe Asn Val Asp Gly Ser Glu Val Ile Asn Thr Gly Val Asp Phe Leu
        580                 585                 590

GAT AGA GGT ACA GGA TTT AAT ACA GGT TTT AGA AAT GCA ATA TTT GAA    1824
Asp Arg Gly Thr Gly Phe Asn Thr Gly Phe Arg Asn Ala Ile Phe Glu
    595                 600                 605

AAT ACA TAT AAC CTT GGC AGT AGA GCT TCA GAA ATT TCA ACT GCT CGT    1872
Asn Thr Tyr Asn Leu Gly Ser Arg Ala Ser Glu Ile Ser Thr Ala Arg
610                 615                 620

AAA AAA CAA GGT TCT CCT GAA CAA ACT CAC GTT TGG GAT AAT ATT AGA    1920
Lys Lys Gln Gly Ser Pro Glu Gln Thr His Val Trp Asp Asn Ile Arg
625                 630                 635                 640

AAC CCT AAT TCT GTT GAT TTT CCA ATA AGT GAT GGT ACA GAA AAT CTA    1968
Asn Pro Asn Ser Val Asp Phe Pro Ile Ser Asp Gly Thr Glu Asn Leu
            645                 650                 655

GTA AAT AAA TTC TGC CCA GAT TGG AAT ATA GAA CCA TGT AAT CCT GTA    2016
Val Asn Lys Phe Cys Pro Asp Trp Asn Ile Glu Pro Cys Asn Pro Val
        660                 665                 670

GAC GAA ACC AAC CAA GCA CCT ACA ATA AGC TTC CTA TCT CCT GTT AAC    2064
Asp Glu Thr Asn Gln Ala Pro Thr Ile Ser Phe Leu Ser Pro Val Asn
    675                 680                 685

AAT ATT ACT TTA GTT GAA GGT TAT AAT TTA CAA GTT GAA GTT AAT GCT    2112
Asn Ile Thr Leu Val Glu Gly Tyr Asn Leu Gln Val Glu Val Asn Ala
690                 695                 700

ACT GAT GCA GAT GGA ACT ATT GAT AAT GTA AAA CTT TAT ATA GAT AAC    2160
Thr Asp Ala Asp Gly Thr Ile Asp Asn Val Lys Leu Tyr Ile Asp Asn
705                 710                 715                 720
```

FIG. 17c

```
AAT TTA GTT AGG CAA ATA AAT TCT ACT TCA TAT AAA TGG GGC CAT TCT     2208
Asn Leu Val Arg Gln Ile Asn Ser Thr Ser Tyr Lys Trp Gly His Ser
                725                 730                 735

GAT TCT CCA AAT ACA GAT GAA CTT AAT GGT CTT ACA GAA GGA ACT TAT     2256
Asp Ser Pro Asn Thr Asp Glu Leu Asn Gly Leu Thr Glu Gly Thr Tyr
            740                 745                 750

ACC TTA AAA GCA ATT GCA ACT GAT AAC GAC GGG GCT TCT ACA GAA ACG     2304
Thr Leu Lys Ala Ile Ala Thr Asp Asn Asp Gly Ala Ser Thr Glu Thr
        755                 760                 765

CAA TTT ACG TTA ACT GTA ATA ACA GAA CAA AGT CCG TCT GAG AAT TGT     2352
Gln Phe Thr Leu Thr Val Ile Thr Glu Gln Ser Pro Ser Glu Asn Cys
    770                 775                 780

GAC TTT AAT ACA CCT TCT TCA ACT GGT TTA GAA GAT TTT GAC ATT AAA     2400
Asp Phe Asn Thr Pro Ser Ser Thr Gly Leu Glu Asp Phe Asp Ile Lys
785                 790                 795                 800

AAG TTT TCT AAC GTT TTT GAG TTA GGA TCT GGC GGA CCA TCT TTA AGT     2448
Lys Phe Ser Asn Val Phe Glu Leu Gly Ser Gly Gly Pro Ser Leu Ser
                805                 810                 815

AAT TTA AAA ACA TTT ACT ATT AAT TGG AAT TCG CAA TAC AAT GGG TTA     2496
Asn Leu Lys Thr Phe Thr Ile Asn Trp Asn Ser Gln Tyr Asn Gly Leu
            820                 825                 830

TAT CAA TTT TCA ATA AAC ACA AAC AAC GGT GTA CCT GAT TAT TAT ATA     2544
Tyr Gln Phe Ser Ile Asn Thr Asn Asn Gly Val Pro Asp Tyr Tyr Ile
        835                 840                 845

AAT TTA AAA CCA AAA ATT ACC TTT CAG TTT AAA AAT GCA AAT CCA GAA     2592
Asn Leu Lys Pro Lys Ile Thr Phe Gln Phe Lys Asn Ala Asn Pro Glu
    850                 855                 860

ATA TCT ATT AGC AAT AGC TTA ATT CCT AAT TTT GAT GGT GAT TAC TGG     2640
Ile Ser Ile Ser Asn Ser Leu Ile Pro Asn Phe Asp Gly Asp Tyr Trp
865                 870                 875                 880

GTA ACA TCA GAT AAC GGT AAT TTT GTG ATG GTA TCT AAA ACT AAT AAT     2688
Val Thr Ser Asp Asn Gly Asn Phe Val Met Val Ser Lys Thr Asn Asn

                885                 890                 895
TTT ACG ATA TAC TTT AGT AAT GAC GCT ACT GCT CCT ATT TGT AAT GTT     2736
Phe Thr Ile Tyr Phe Ser Asn Asp Ala Thr Ala Pro Ile Cys Asn Val
            900                 905                 910

ACG CCT AGT AAC CAA ATA AGT AAA ATT ACT GAT GAT TCT AGT ATT AAT     2784
Thr Pro Ser Asn Gln Ile Ser Lys Ile Thr Asp Asp Ser Ser Ile Asn
        915                 920                 925

TTT AAG CTT TAC CCT AAT CCT GCT TTA GAC GAA ACT ATT TTT GTG AGC     2832
Phe Lys Leu Tyr Pro Asn Pro Ala Leu Asp Glu Thr Ile Phe Val Ser
    930                 935                 940

GCT GAA GAT GAA AAA CTA GCT TTG GTG CTT GTA CC AGT                  2870
Ala Glu Asp Glu Lys Leu Ala Leu Val Leu Val Pro
945                 950                 955
```

FIG. 17d

PYROCOCCUS FURIOSUS VC1 (7EG1)

```
ATG AGC AAG AAA AAG TTC GTC ATC GTA TCT ATC TTA ACA ATC CTT TTA      48
Met Ser Lys Lys Lys Phe Val Ile Val Ser Ile Leu Thr Ile Leu Leu
 1               5                  10                  15

GTA CAG GCA ATA TAT TTT GTA GAA AAG TAT CAT ACC TCT GAG GAC AAG      96
Val Gln Ala Ile Tyr Phe Val Glu Lys Tyr His Thr Ser Glu Asp Lys
            20                  25                  30

TCA ACT TCA AAT ACC TCA TCT ACA CCA CCC CAA ACA ACA CTT TCC ACT     144
Ser Thr Ser Asn Thr Ser Ser Thr Pro Pro Gln Thr Thr Leu Ser Thr
        35                  40                  45

ACC AAG GTT CTC AAG ATT AGA TAC CCT GAT GAC GGT GAG TGG CCA GGA     192
Thr Lys Val Leu Lys Ile Arg Tyr Pro Asp Asp Gly Glu Trp Pro Gly
    50                  55                  60

GCT CCT ATT GAT AAG GAT GGT GAT GGG AAC CCA GAA TTC TAC ATT GAA     240
Ala Pro Ile Asp Lys Asp Gly Asp Gly Asn Pro Glu Phe Tyr Ile Glu
65                  70                  75                  80

ATA AAC CTA TGG AAC ATT CTT AAT GCT ACT GGA TTT GCT GAG ATG ACG     288
Ile Asn Leu Trp Asn Ile Leu Asn Ala Thr Gly Phe Ala Glu Met Thr
                85                  90                  95

TAC AAT TTA ACC AGC GGC GTC CTT CAC TAC GTC CAA CAA CTT GAC AAC     336
Tyr Asn Leu Thr Ser Gly Val Leu His Tyr Val Gln Gln Leu Asp Asn
            100                 105                 110

ATT GTC TTG AGG GAT AGA AGT AAT TGG GTG CAT GGA TAC CCC GAA ATA     384
Ile Val Leu Arg Asp Arg Ser Asn Trp Val His Gly Tyr Pro Glu Ile
        115                 120                 125

TTC TAT GGA AAC AAG CCA TGG AAT GCA AAC TAC GCA ACT GAT GGC CCA     432
Phe Tyr Gly Asn Lys Pro Trp Asn Ala Asn Tyr Ala Thr Asp Gly Pro
    130                 135                 140

ATA CCA TTA CCC AGT AAA GTT TCA AAC CTA ACA GAC TTC TAT CTA ACA     480
Ile Pro Leu Pro Ser Lys Val Ser Asn Leu Thr Asp Phe Tyr Leu Thr
145                 150                 155                 160

ATC TCC TAT AAA CTT GAG CCC AAG AAC GGC CTG CCA ATT AAC TTC GCA     528
Ile Ser Tyr Lys Leu Glu Pro Lys Asn Gly Leu Pro Ile Asn Phe Ala
                165                 170                 175

ATA GAA TCC TGG TTA ACG AGA GAA GCT TGG AGA ACA ACA GGA ATT AAC     576
Ile Glu Ser Trp Leu Thr Arg Glu Ala Trp Arg Thr Thr Gly Ile Asn
            180                 185                 190

AGC GAT GAG CAA GAA GTA ATG ATA TGG ATT TAC TAT GAC GGA TTA CAA     624
Ser Asp Glu Gln Glu Val Met Ile Trp Ile Tyr Tyr Asp Gly Leu Gln
        195                 200                 205

CCG GCT GGC TCC AAA GTT AAG GAG ATT GTA GTC CCA ATA ATA GTT AAC     672
Pro Ala Gly Ser Lys Val Lys Glu Ile Val Val Pro Ile Ile Val Asn
    210                 215                 220
```

FIG. 18a

```
GGA ACA CCA GTA AAT GCT ACA TTT GAA GTA TGG AAG GCA AAC ATT GGT      720
Gly Thr Pro Val Asn Ala Thr Phe Glu Val Trp Lys Ala Asn Ile Gly
225                 230                 235                 240

TGG GAG TAT GTT GCA TTT AGA ATA AAG ACC CCA ATC AAA GAG GGA ACA      768
Trp Glu Tyr Val Ala Phe Arg Ile Lys Thr Pro Ile Lys Glu Gly Thr
                245                 250                 255

GTG ACA ATT CCA TAC GGA GCA TTT ATA AGT GTT GCA GCC AAC ATT TCA      816
Val Thr Ile Pro Tyr Gly Ala Phe Ile Ser Val Ala Ala Asn Ile Ser
            260                 265                 270

AGC TTA CCA AAT TAC ACA GAA CTT TAC TTA GAG GAC GTG GAG ATT GGA      864
Ser Leu Pro Asn Tyr Thr Glu Leu Tyr Leu Glu Asp Val Glu Ile Gly
        275                 280                 285

ACT GAG TTT GGA ACG CCA AGC ACT ACC TCC GCC CAC CTA GAG TGG TGG      912
Thr Glu Phe Gly Thr Pro Ser Thr Thr Ser Ala His Leu Glu Trp Trp
    290                 295                 300

ATC ACA AAC ATA ACA CTA ACT CCT CTA GAT AGA CCT CTT ATT TCC TAA      960
Ile Thr Asn Ile Thr Leu Thr Pro Leu Asp Arg Pro Leu Ile Ser
305                 310                 315
```

FIG. 18b

GLYCOSIDASE ENZYMES

CROSS REFERENCES TO RELATED APPLICATIONS

This application is a divisional application of U.S. patent application Ser. No. 09/134,078, filed Aug. 13, 1998, now U.S. Pat. No. 6,368,844, which is a continuation of U.S. patent application Ser. No. 08/949,026, filed Oct. 10, 1997, now abandoned, which claims priority under 35 USC §119 (e)(1) of prior U.S. provisional application No. 60/056,916, filed Dec. 6, 1996, which are all hereby incorporated by reference.

This application is properly filed under 35 USC §120 during the pendency of U.S. patent application Ser. No. 10/121,032, filed Apr. 9, 2002, which is a continuation of U.S. patent application Ser. No. 09/134,078, filed Aug. 13, 1998, now U.S. Pat. No. 6,368,844, which is a continuation of U.S. patent application Ser. No. 08/949,026, filed Oct. 10, 1997, now abandoned, which claims priority under 35 USC §119 (e)(1) of prior U.S. provisional application No. 60/056,916, filed Dec. 6, 1996, which are all hereby incorporated by reference.

REFERENCE TO SEQUENCE LISTING SUBMITTED VIA EFS-WEB

This application is being filed electronically via the USPTO EFS-WEB server, as authorized and set forth in the MPEP §1730 II.B.2(a)(A), and this electronic filing includes an electronically submitted sequence (SEQ ID) listing. The entire content of this sequence listing is herein incorporated by reference for all purposes. The sequence listing is identified on the electronically filed .txt file as follows:

| File Name | Date of Creation | Size (bytes) |
| --- | --- | --- |
| 20071002SequenceListingD13207D1 | Oct. 2, 2007 | 131,301 bytes |

BACKGROUND OF THE INVENTION

1. Field of the Inventions

This invention relates to newly identified polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been putatively identified as glucosidases, α-galactosidases, β-galactosidases, β-mannosidases, β-mannanases, endoglucanases, and pullulanases.

2. Description of Related Art

The glycosidic bond of β-galactosides can be cleaved by different classes of enzymes: (i) phospho-β-galactosidases (EC3.2.1.85) are specific for a phosphorylated substrate generated via phosphoenolpyruvate phosphotransferase system (PTS)-dependent uptake; (ii) typical β-galactosidases (EC 3.2.1.23), represented by the *Escherichia coli* LacZ enzyme, which are relatively specific for β-galactosides; and (iii) β-glucosidases (EC 3.2.1.21) such as the enzymes of *Agrobacterium faecalis, Clostridium thermocellum, Pyrococcus furiosus* or *Sulfolobus solfataricus* (Day, A. G. and Withers, S. G., (1986) Purification and characterization of a β-glucosidase from *Alcaligenes faecalis*. Can. J. Biochem. Cell. Biol. 64, 914-922; Kengen, S. W. M., et al. (1993) Eur. J. Biochem., 213, 305-312; Ait, N., Cruezet, N. and Cattaneo, J. (1982) Properties of β-glucosidase purified from *Clostridium thermocellum*. J. Gen. Microbiol. 128, 569-577; Grogan, D. W. (1991) Evidence that β-galactosidase of *Sulfolobus solfataricus* is only one of several activities of a thermostable β-D-glycosidase. Appl. Environ. Microbiol. 57, 1644-1649). Members of the latter group, although highly specific with respect to the β-anomeric configuration of the glycosidic linkage, often display a rather relaxed substrate specificity and hydrolyse β-glucosides as well as β-fucosides and β-galactosides.

Generally, α-galactosidases are enzymes that catalyze the hydrolysis of galactose groups on a polysaccaride backbone or hydrolyze the cleavage of di- or oligosaccharides comprising galactose.

Generally, β-mannanases are enzymes that catalyze the hydrolysis of mannose groups internally on a polysaccaride backbone or hydrolyze the cleavage of di- or oligosaccaharides comprising mannose groups. β-mannosidases hydrolyze non-reducing, terminal mannose residues on a mannose-containing polysaccharide and the cleavage of di- or oligosaccaharides comprising mannose groups.

Guar gum is a branched galactomannan polysaccharide composed of β-1,4 linked mannose backbone with α-1,6 linked galactose sidechains. The enzymes required for the degradation of guar are β-mannanase, β-mannosidase and α-galactosidase. β-mannanase hydrolyses the mannose backbone internally and β-mannosidase hydrolyses non-reducing, terminal mannose residues, α-galactosidase hydrolyses α-linked galactose groups.

Galactomannan polysaccharides and the enzymes that degrade them have a variety of applications. Guar is commonly used as a thickening agent in food and is utilized in hydraulic fracturing in oil and gas recovery. Consequently, galactomannanases are industrially relevant for the degradation and modification of guar. Furthermore, a need exists for thermostable galactomannases that are active in extreme conditions associated with drilling and well stimulation.

There are other applications for these enzymes in various industries, such as in the beet sugar industry. 20-30% of the domestic U.S. sucrose consumption is sucrose from sugar beets. Raw beet sugar can contain a small amount of raffinose when the sugar beets are stored before processing and rotting begins to set in. Raffinose inhibits the crystallization of sucrose and also constitutes a hidden quantity of sucrose. Thus, there is merit to eliminating raffinose from raw beet sugar. α-Galactosidase has also been used as a digestive aid to break down raffinose, stachyose, and verbascose in such foods as beans and other gassy foods.

β-Galactosidases which are active and stable at high temperatures appear to be superior enzymes for the production of lactose-free dietary milk products (Chaplin, M. F. and Bucke, C. (1990) In: Enzyme Technology, pp. 159-160, Cambridge University Press, Cambridge, UK). Also, several studies have demonstrated the applicability of β-galactosidases to the enzymatic synthesis of oligosaccharides via transglycosylation reactions (Nilsson, K. G. I. (1988) Enzymatic synthesis of oligosaccharides. Trends Biotechnol. 6, 156-264; Cote, G. L. and Tao, B. Y. (1990) Oligosaccharide synthesis by enzymatic transglycosylation. Glycoconjugate J. 7, 145-162). Despite the commercial potential, only a few β-galactosidases of thermophiles have been characterized so far. Two genes reported are β-galactoside-cleaving enzymes of the hyperthermophilic bacterium *Thermotoga maritima*, one of the most thermophilic organotrophic eubacteria described to date (Huber, R., Langworthy, T. A., König, H., Thomm, M., Woese, C. R., Sleytr, U. B. and Stetter, K. O. (1986) *T. mar-*

*tima* sp. nov. represents a new genus of unique extremely thermophilic eubacteria growing up to 90° C., Arch. Microbiol. 144, 324-333) one of the most thermophilic organotrophic eubacteria described to date. The gene products have been identified as a β-galactosidase and a β-glucosidase.

Pullulanase is well known as a debranching enzyme of pullulan and starch. The enzyme hydrolyzes α-1,6-glucosidic linkages on these polymers. Starch degradation for the production or sweeteners (glucose or maltose) is a very important industrial application of this enzyme. The degradation of starch is developed in two stages. The first stage involves the liquefaction of the substrate with α-amylase, and the second stage, or saccharification stage, is performed by β-amylase with pullulanase added as a debranching enzyme, to obtain better yields.

Endoglucanases can be used in a variety of industrial applications. For instance, the endoglucanases of the present invention can hydrolyze the internal β-1,4-glycosidic bonds in cellulose, which may be used for the conversion of plant biomass into fuels and chemicals. Endoglucanases also have applications in detergent formulations, the textile industry, in animal feed, in waste treatment, and in the fruit juice and brewing industry for the clarification and extraction of juices.

The polynucleotides and polypeptides of the present invention have been identified as glucosidases, α-galactosidases, β-galactosidases, β-mannosidases, β-mannanases, endoglucanases, and pullulanases as a result of their enzymatic activity.

In accordance with one aspect of the present invention, there are provided novel enzymes, as well as active fragments, analogs and derivatives thereof.

In accordance with another aspect of the present invention, there are provided isolated nucleic acid molecules encoding the enzymes of the present invention including mRNAs, cDNAs, genomic DNAs as well as active analogs and fragments of such enzymes.

In accordance with another aspect of the present invention there are provided isolated nucleic acid molecules encoding mature polypeptides expressed by the DNA contained in ATCC Deposit No. 97379.

In accordance with yet a further aspect of the present invention, there is provided a process for producing such polypeptides by recombinant techniques comprising culturing recombinant prokaryotic and/or eukaryotic host cells, containing a nucleic acid sequence of the present invention, under conditions promoting expression of said enzymes and subsequent recovery of said enzymes.

In accordance with yet a further aspect of the present invention, there is provided a process for utilizing such enzymes, or polynucleotides encoding such enzymes for hydrolyzing lactose to galactose and glucose for use in the food processing industry, the pharmaceutical industry, for example, to treat intolerance to lactose, as a diagnostic reporter molecule, in corn wet milling, in the fruit juice industry, in baking, in the textile industry and in the detergent industry.

In accordance with yet a further aspect of the present invention, there is provided a process for utilizing such enzymes for hydrolyzing guar gum (a galactomannan polysaccharide) to remove non-reducing terminal mannose residues. Further polysaccharides such as galactomannan and the enzymes according to the invention that degrade them have a variety of applications. Guar gum is commonly used as a thickening agent in food and also is utilized in hydraulic fracturing in oil and gas recovery. Consequently, mannanases are industrially relevant for the degradation and modification of guar gums. Furthermore, a need exists for thermostable mannases that are active in extreme conditions associated with drilling and well stimulation.

In accordance with yet a further aspect of the present invention, there are also provided nucleic acid probes comprising nucleic acid molecules of sufficient length to specifically hybridize to a nucleic acid sequence of the present invention.

In accordance with yet a further aspect of the present invention, there is provided a process for utilizing such enzymes, or polynucleotides encoding such enzymes, for in vitro purposes related to scientific research, for example, to generate probes for identifying similar sequences which might encode similar enzymes from other organisms by using certain regions, i.e., conserved sequence regions, of the nucleotide sequence.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 is an illustration of the full-length DNA (SEQ ID NO:1) and corresponding deduced amino acid sequence (SEQ ID NO:15) of M11TL-29G of the present invention. Sequencing was performed using a 378 automated DNA sequencer for all sequences of the present invention (Applied Biosystems, Inc.).

FIG. 2 is an illustration of the full-length DNA (SEQ ID NO:2) and corresponding deduced amino acid sequence (SEQ ID NO: 16) of OC1/4V-33B/G.

FIG. 3 is an illustration of the full-length DNA (SEQ ID NO:3) and corresponding deduced amino acid sequence (SEQ ID NO: 17) of F1-12G.

FIG. 4 are illustrations of the full-length DNA (SEQ ID NO:4) and corresponding deduced amino acid sequence (SEQ ID NO: 18) of 9N2-3 1B/G.

FIG. 5 are illustrations of the full-length DNA (SEQ ID NO:5) and corresponding deduced amino acid sequence (SEQ ID NO:19) of MSB8-6G.

FIG. 6 are illustrations of the full-length DNA (SEQ ID NO:6) and corresponding deduced amino acid sequence (SEQ ID NO:20) of AEDII12RA-18B/G.

FIG. 7 is an illustration of the full-length DNA (SEQ ID NO:7) and corresponding deduced amino acid sequence (SEQ ID NO:21) of GC74-22G.

FIG. 8 is an illustration of the full-length DNA (SEQ ID NO:8) and corresponding deduced amino acid sequence (SEQ ID NO:22) of VC1-7G1.

FIG. 9 is an illustration of the full-length DNA (SEQ ID NO:9) and corresponding deduced amino acid sequence (SEQ ID NO:23) of 37GP1.

FIG. 10 is an illustration of the full-length DNA (SEQ ID NO:10) and corresponding deduced amino acid sequence (SEQ ID NO:24) of 6GC2.

FIG. 11 is an illustration of the full-length DNA (SEQ ID NO:11) and corresponding deduced amino acid sequence (SEQ ID NO:25) of 6GP2.

FIG. 12 is an illustration of the full-length DNA (SEQ ID NO:12) and corresponding deduced amino acid sequence (SEQ ID NO:26) of 63 GB1.

FIG. 13 is an illustration of the full-length DNA (SEQ ID NO:13) and corresponding deduced amino acid sequence (SEQ ID NO:27) of OC1/4V 33GP1.

FIG. 14 is an illustration of the full-length DNA (SEQ ID NO:14) and corresponding deduced amino acid sequence (SEQ ID NO:28) of 6GP3.

FIG. 15 is an illustration of the full-length DNA (SEQ ID NO:57) and corresponding deduced amino acid sequence (SEQ ID NO:61) of *Thermotoga maritima* MSB8-6GP2.

FIG. 16 is an illustration of the full-length DNA (SEQ ID NO:58) and corresponding deduced amino acid sequence (SEQ ID NO:62) of *Thermotoga maritima* MSB8-6GP4.

FIG. 17 is an illustration of the full-length DNA (SEQ ID NO:59) and corresponding deduced amino acid sequence (SEQ ID NO:63) of *Banki gouldi* 37GP4.

FIG. 18 is an illustration of the full-length DNA (SEQ ID NO:60) and corresponding deduced amino acid sequence (SEQ ID NO:64) of *Pyrococcus furiosus* VC1-7EG1.

SUMMARY OF THE INVENTION

In accordance with an aspect of the present invention, there are provided isolated nucleic acids (polynucleotides) which encode for the mature enzymes having the deduced amino acid sequences of FIGS. 1-18 (SEQ ID NOS: 15-28 and 61-64).

In accordance with another aspect of the present invention, there are provided isolated polynucleotides encoding the enzymes of the present invention. The deposited material is a mixture of genomic clones comprising DNA encoding an enzyme of the present invention. Each genomic clone comprising the respective DNA has been inserted into a pBluescript vector (Stratagene, La Jolla, Calif.). The deposit has been deposited with the American Type Culture Collection, 12301 Parklawn Drive, Rockville, Md. 20852, USA, on Dec. 13, 1995 and assigned ATCC Deposit No. 97379.

The deposit(s) have been made under the terms of the Budapest Treaty on the International Recognition of the deposit of micro-organisms for purposes of patent procedure. The strains will be irrevocably and without restriction or condition released to the public upon the issuance of a patent. These deposits are provided merely as convenience to those of skill in the art and are not an admission that a deposit be required under 35 U.S.C. §112. The sequences of the polynucleotides contained in the deposited materials, as well as the amino acid sequences of the polypeptides encoded thereby, are controlling in the event of any conflict with any description of sequences herein. A license may be required to make, use or sell the deposited materials, and no such license is hereby granted.

The publications discussed herein are provided solely for their disclosure prior to the filing date of the present application. Nothing herein is to be construed as an admission that the invention is not entitled to antedate such disclosure by virtue of prior invention.

Definitions

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences.

DETAILED DESCRIPTION OF THE INVENTION

The polynucleotides of this invention were originally recovered from genomic gene libraries derived from the following organisms:

M11TL is a new species of *Desulfurococcus* isolated from Diamond Pool in Yellowstone National Park. The organism grows optimally at 85-88° C., pH 7.0 in a low salt medium containing yeast extract, peptone, and gelatin as substrates with a $N_2/CO_2$ gas phase.

OC1/4V is from the genus *Thermotoga*. The organism was isolated from Yellowstone National Park. It grows optimally at 75° C. in a low salt medium with cellulose as a substrate and $N_2$ in gas phase.

*Pyrococcus furiosus* VC1 is from the genus *Pyrococcus*. VC1 was isolated from Vulcano, Italy. It grows optimally at 100° C. in a high salt medium (marine) containing elemental sulfur, yeast extract, peptone and starch as substrates and $N_2$ in gas phase.

*Staphylothermus marinus* F1 is from the genus *Staphylothermus*. F1 was isolated from Vulcano, Italy. It grows optimally at 85° C., pH 6.5 in high salt medium (marine) containing elemental sulfur and yeast extract as substrates and $N_2$ in gas phase.

*Thermococcus* 9N-2 is from the genus *Thermococcus* 9N-2 was isolated from diffuse vent fluid in the East Pacific Rise. It is a strict anaerobe that grows optimally at 87° C.

*Thermotoga maritima* MSB8 is from the genus *Thermotoga*, and was isolated from Vulcano, Italy. MSB8 grows optimally at 85° C. pH 6.5 in a high salt medium (marine) containing starch and yeast extract as substrates and $N_2$ in gas phase.

*Thermococcus alcaliphilus* AEDII12RA is from the genus *Thermococcus*. AEDII12RA grows optimally at 85° C., pH 9.5 in a high salt medium (marine) containing polysulfides and yeast extract as substrates and $N_2$ in gas phase.

*Thermococcus chitonophagus* GC74 is from the genus *Thermococcus*. GC74 grows optimally at 85° C., pH 6.0 in a high salt medium (marine) containing chitin, meat extract, elemental sulfur and yeast extract as substrates and $N_2$ in gas phase. AEPII 1a grows optimally at 85° C. at pH 6.5 in marine medium under anaerobic conditions. It has many substrates. *Bankia gouldi* is from the genus *Bankia*.

Accordingly, the polynucleotides and enzymes encoded thereby are identified by the organism from which they were isolated, and are sometimes hereinafter referred to as "M11TL" (FIG. 1 and SEQ ID NOS:1 and 15), "OC1/4V-33B/G" (FIG. 2 and SEQ ID NOS:2 and 16), "F1-12G" (FIG. 3 and SEQ ID NOS:3 and 17), "9N2-31B/G" (FIG. 4 and SEQ ID NOS:4 and 18), "MSB8" (FIG. 5 and SEQ ID NOS:5 and 19), "AEDII12RA-18B/G" (FIG. 6 and SEQ ID NOS:6 and 20), "GC74-22G" (FIG. 7 and SEQ ID NOS:7 and 21), "VC1-7G1" (FIG. 8 and SEQ ID NOS:8 and 22), "37GP1" (FIG. 9 and SEQ ID NOS: 9 and 23), "6GC2" (FIG. 10 and SEQ ID NOS: 10 and 24), "6GP2" (FIG. 11 and SEQ ID NOS:11 and 25), "AEPII 1a" (FIG. 12 and SEQ ID NOS:12 and 26), "OC1/4V" (FIG. 13 and SEQ ID NOS:13 and 27), and "6GP3" (FIG. 14 and SEQ ID NOS:28), "MSB8-6GP2" (FIG. 15 and SEQ ID NOS:57 and 61), "MSB8-6GP4" (FIG. 16 and SEQ ID NOS:58 and 62), "VC1-7EG1" (FIG. 17 and SEQ ID NOS:59 and 63), and 37GP4 (FIG. 18 and SEQ ID NOS:60 and 64).

The polynucleotides and polypeptides of the present invention show identity at the nucleotide and protein level to known genes and proteins encoded thereby as shown in Table 1.

TABLE 1

| Clone | Gene/Protein with Closest Homology | Protein Identity | Nucleic Acid Identity |
|---|---|---|---|
| M11TL-29G (DNA SEQ ID NO: 1, Protein SEQ ID NO: 15) | *Sulfolobus sulfataricus* DSM 1616/P1, β-galactosidase | 51% | 55% |
| OC1/4V-33B/G (DNA SEQ ID NO: 2, Protein SEQ ID NO: 16) | *Caldocellum saccharolyticum*, β-glucosidase | 52% | 57% |
| *Staphylothermus marinus* F1-12G (DNA SEQ ID NO: 3, Protein SEQ ID NO: 17) | *Bacillus polymyxa*, β-galactosidase | 36% | 48% |
| *Thermococcus* 9N2-31B/G (DNA SEQ ID NO: 4, Protein SEQ ID NO: 18) | *Sulfolobus sulfataricus* ATCC 49255/MT4, β-galactosidase | 51% | 50% |
| *Thermotoga maritima* MSB8-6G (DNA SEQ ID NO: 5, Protein SEQ ID NO: 19) | *Clostridium thermocellum* bglB | 45% | 53% |
| *Thermococcus* AEDII12RA-18B/G (DNA SEQ ID NO: 6, Protein SEQ ID NO: 20) | *Bacillus polymyxa*, β-galactosidase | 34% | 48% |
| *Thermococcus chitonophagus* GC74-22G (DNA SEQ ID NO: 7, Protein SEQ ID NO: 21) | *Sulfolobus sulfataricus* ATCC 49255/MT4, β-galactosidase | 46% | 54% |
| *Pyrococcus furiosus* VC1-7G1 (DNA SEQ ID NO: 8, Protein SEQ ID NO: 22) | *Sulfolobus sulfataricus*/MT-4 β-galactosidase | 46.4% | 52.5% |
| *Thermotoga maritima* α-galactosidase (6GC2) (DNA SEQ ID NO: 10, Protein SEQ ID NO: 24) | *Pediococcus pentosaceaus* α-galactosidase | 49% | 29% |
| *Thermotoga maritima* β-mannanase (6GP2) (DNA SEQ ID NO: 11, Protein SEQ ID NO: 25) | *Aspergillus aculeatus* mannanase | 56% | 37% |
| AEPII 1a β-mannosidase (63GB1) (DNA SEQ ID NO: 12, Protein SEQ ID NO: 26) | *Sulfolobus solfactaricus* β-galactosidase | 78% | 56% |
| OC1/4V endoglucanase (33GP1) (DNA SEQ ID NO: 13, Protein SEQ ID NO: 27) | *Clostridium thermocellum* endo-1,4-β-endoglucanase | 65% | 43% |
| *Thermotoga maritima* pullulanase (6GP3) (DNA SEQ ID NO: 14, Protein SEQ ID NO: 28) | *Caldocellum saccharolyticum* α-destrom 6 glucanohydralase | 72% | 53% |
| *Bankia gouldi* mix Endoglucanase (37GP1) (DNA SEQ ID NO: 9, Protein SEQ ID NO: 23) | None available | | |

The polynucleotides and enzymes of the present invention show homology to each other as shown in Table 2.

TABLE 2

| Clone | Gene/Protein with Closest Homology | Protein Identity | Nucleic Acid Identity |
|---|---|---|---|
| *Staphylothermus marinus* F1-12G (DNA SEQ ID NO: 3, Protein SEQ ID NO: 17) | *Thermococcus* AEDII12RA-18B/G, β-galactosidase, glucosidase (DNA SEQ ID NO: 6, Protein SEQ ID NO: 20) | 55% | 57% |
| *Thermococcus* 9N2-31B/G (DNA SEQ ID NO: 4, Protein SEQ ID NO: 18) | *Thermococcus chitonophagus* GC74-22G-glucosidase (DNA SEQ ID NO: 7, Protein SEQ ID NO: 21) | 74% | 66% |

TABLE 2-continued

| Clone | Gene/Protein with Closest Homology | Protein Identity | Nucleic Acid Identity |
|---|---|---|---|
| *Pyrococcus furiosus* VC1 - 7G1 (DNA SEQ ID NO: 8, Protein SEQ ID NO: 22) | *Pyrococcus furiosus* VC1-7B/G β-galactosidase | 46.4% | 54% |

All the clones identified in Tables 1 and 2 encode polypeptides which have α-glycosidase or β-glycosidase activity.

This invention, in addition to the isolated nucleic acid molecules encoding the enzymes of the present invention, also provide substantially similar sequences. Isolated nucleic acid sequences are substantially similar if: (i) they are capable of hybridizing under conditions hereinafter described, to the polynucleotides of SEQ ID NOS: 1-14 and 57-60; (ii) or they encode DNA sequences which are degenerate to the polynucleotides of SEQ ID NOS: 1-14 and 57-60. Degenerate DNA sequences encode the amino acid sequences of SEQ ID NOS: 15-28 and 61-64, but have variations in the nucleotide coding sequences. As used herein, substantially similar refers to the sequences having similar identity to the sequences of the instant invention. The nucleotide sequences that are substantially the same can be identified by hybridization or by sequence comparison. Enzyme sequences that are substantially the same can be identified by one or more of the following: proteolytic digestion, gel electrophoresis and/or microsequencing.

One means for isolating the nucleic acid molecules encoding the enzymes of the present invention is to probe a gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated to one skilled in the art that the polynucleotides of SEQ ID NOS: 1-14 and 57-60 or fragments thereof (comprising at least 12 contiguous nucleotides), are particularly useful probes. Other particularly useful probes for this purpose are hybridizable fragments to the sequences of SEQ ID NOS: 1-14 and 57-60 (i.e., comprising at least 12 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10× Denhardt's, and 0.5 mg/mL polyriboadenylic acid. Approximately $2\times10^7$ cpm (specific activity 4-$9\times10^8$ cpm/ug) of $^{32}P$ end-labeled oligonucleotide probe are then added to the solution. After 12-16 hours of incubation, the membrane is washed for 30 minutes at room temperature in 1× SET (150 mM NaCl, 20 mM Tris hydrochloride, pH 7.8, 1 mM $Na_2EDTA$) containing 0.5% SDS, followed by a 30 minute wash in fresh 1× SET at Tm 10° C. for the oligonucleotide probe. The membrane is then exposed to autoradiographic film for detection of hybridization signals.

Stringent conditions means hybridization will occur only if there is at least 90% identity, preferably at least 95% identity and most preferably at least 97% identity between the sequences. Further, it is understood that a section of a 100 bps sequence that is 95 bps in length has 95% identity with the 1090 bps sequence from which it is obtained. See J. Sambrook et al., *Molecular Cloning, A Laboratory Manual,* 2d Ed., Cold Spring Harbor Laboratory (1989) which is hereby incorporated by reference in its entirety. Also, it is understood that a fragment of a 100 bps sequence that is 95 bps in length has 95% identity with the 100 bps sequence from which it is obtained.

As used herein, a first DNA (RNA) sequence is at least 70% and preferably at least 80% identical to another DNA (RNA) sequence if there is at least 70% and preferably at least a 80% or 90% identity, respectively, between the bases of the first sequence and the bases of the another sequence, when properly aligned with each other, for example when aligned by BLASTN.

"Identity" as the term is used herein, refers to a polynucleotide sequence which comprises a percentage of the same bases as a reference polynucleotide (SEQ ID NOS: 1-14 and 57-60). For example, a polynucleotide which is at least 90% identical to a reference polynucleotide, has polynucleotide bases which are identical in 90% of the bases which make up the reference polynucleotide and may have different bases in 10% of the bases which comprise that polynucleotide sequence.

The present invention relates polynucleotides which differ from the reference polynucleotide such that the changes are silent changes, for example the changes do not alter the amino acid sequence encoded by the polynucleotide. The present invention also relates to nucleotide changes which result in amino acid substitutions, additions, deletions, fusions and truncations in the polypeptide encoded by the reference polynucleotide. In a preferred aspect of the invention these polypeptides retain the same biological action as the polypeptide encoded by the reference polynucleotide.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other sources or to screen such sources for related sequences.

The polynucleotides of this invention were recovered from genomic gene libraries from the organisms listed in Table 1. For example, gene libraries can be generated in the Lambda ZAP II cloning vector (Stratagene Cloning Systems). Mass excisions can be performed on these libraries to generate libraries in the pBluescript phagemid. Libraries are thus generated and excisions performed according to the protocols/methods hereinafter described.

The excision libraries are introduced into the *E. coli* strain BW14893 F'kan1A. Expression clones are then identified using a high temperature filter assay. Expression clones encoding several glucanases and several other glycosidases are identified and repurified. The polynucleotides, and enzymes encoded thereby, of the present invention, yield the activities as described above.

The coding sequences for the enzymes of the present invention were identified by screening the genomic DNAs prepared for the clones having glucosidase or galactosidase activity.

An example of such an assay is a high temperature filter assay wherein expression clones were identified by use of high temperature filter assays using buffer Z (see recipe below) containing 1 mg/ml of the substrate 5-bromo-4-chloro-3-indolyl-β-D-glucopyranoside (XGLU) (Diagnostic Chemicals Limited or Sigma) after introducing an excision library into the *E. coli* strain BW14893 F'kan1A. Expression clones encoding XGLUases were identified and repurified from M11TL, OC 1/4V, *Pyrococcus furiosus* VC 1, *Staphylothemus marinus* F1, *Thermococcus* 9N-2, *Thermotoga maritima* MSB8, *Thermococcus alcaliphilus* AEDII12RA, and *Thermococcus chitonophagus* GC74.

Z-buffer: (referenced in Miller, J. H. (1992) A Short Course in Bacterial Genetics, p. 445.)

| per liter: | |
|---|---|
| $Na_2HPO_4$—$7H_2O$ | 16.1 g |
| $NaH_2PO_4$—$7H_2O$ | 5.5 g |
| KCl | 0.75 g |
| $MgSO_4$—$7H_2O$ | 0.246 g |
| β-mercaptoethanol | 2.7 ml |
| Adjust pH to 7.0 | |

High Temperature Filter Assay (1) The f factor f'kan (from *E. coli* strain CSH118)(1) was introduced into the pho-pnh-lac-strain BW14893(2). BW13893(2). The filamentous phage library was plated on the resulting strain, BW14893 F'kan. (Miller, J. H. (1992) A Short Course in Bacterial Genetics; Lee, K. S., Metcalf, et al., (1992) Evidence for two phosphonate degradative pathways in *Enterobacter Aerogenes*, J. Bacteriol., 174: 2501-2510.

(2) After growth on 100 mm LB plates containing 100 μg/ml ampicillin, 80 μg/ml nethicillin and 1 mM IPTG, colony lifts were performed using Millipore HATF membrane filters.

(3) The colonies transferred to the filters were lysed with chloroform vapor in 150 mm glass petri dishes.

(4) The filters were transferred to 100 mm glass petri dishes containing a piece of Whatman 3MM filter paper saturated with buffer.

(a) when testing for galactosidase activity (XGALase), 3MM paper was saturated with Z buffer containing 1 mg/ml XGAL (ChemBridge Corporation). After transferring filter bearing lysed colonies to the glass petri dish, placed dish in oven at 80-85° C.

(b) when testing for glucosidase (XGLUase), 3MM paper was saturated with Z buffer containing 1 mg/ml XGLU. After transferring filter bearing lysed colonies to the glass petri dish, placed dish in oven at 80-85° C.

(5) 'Positives' were observed as blue spots on the filter membranes. Used the following filter rescue technique to retrieve plasmid from lysed positive colony. Used pasteur pipette (or glass capillary tube) to core blue spots on the filter membrane. Placed the small filter disk in an Eppendorf tube containing 20 μl water. Incubated the Eppendorf tube at 75° C. for 5 minutes followed by vortexing to elute plasmid DNA off filter. This DNA was transformed into electrocompetent *E. coli* cells DH10B for *Thermotoga maritima* MSB8-6G (DNA SEQ ID NO:5, Protein SEQ ID NO:19), *Staphylothermus marinus* F1-12G (DNA SEQ ID NO:3, Protein SEQ ID NO:17), *Thermococcus* AEDII12RA-18B/G (DNA SEQ ID NO:6, Protein SEQ ID NO:20), *Thermococcus chitonophagus* GC74-22G (DNA SEQ ID NO:7, Protein SEQ ID NO:21), M11TL (DNA SEQ ID NO:1, Protein SEQ ID NO:15) and OC1/4V (DNA SEQ ID NO:2, Protein SEQ ID NO:16). Electrocompetent BW14893 F'kan1A *E. coli* were used for *Thermococcus* 9N2-31B/G (DNA SEQ ID NO:4, Protein SEQ ID NO:18), and *Pyrococcus furiosus* VC1-7G1 (DNA SEQ ID NO:8, Protein SEQ ID NO:22). Repeated filter-lift assay on transformation plates to identify 'positives'. Return transformation plates to 37° C. incubator after filter lift to regenerate colonies. Inoculate 3 ml LB liquid containing 100 μg/ml ampicillin with repurified positives and incubate at 37° C. overnight. Isolate plasmid DNA from these cultures and sequence plasmid insert. In some instances where the plates used for the initial colony lifts contained non-confluent colonies, a specific colony corresponding to a blue spot on the filter could be identified on a regenerated plate and repurified directly, instead of using the filter rescue technique.

Another example of such an assay is a variation of the high temperature filter assay wherein colony-laden filters are heat-killed at different temperatures (for example, 105° C. for 20 minutes) to monitor thermostability. The 3MM paper is saturated with different buffers (i.e., 100 mM NaCl, 5 mM MgCl2, 100 mM Tris-Cl (pH 9.5)) to determine enzyme lot activity under different buffer conditions.

A β-glucosidase assay may also be employed, wherein GlcpβNp is used as an artificial substrate (aryl-β-glucosidase). The increase in absorbance at 405 nm as a result of p-nitrophenol (pNp) liberation was followed on a Hitachi U-1100 spectrophotometer, equipped with a thermostatted cuvette holder. The assays may be performed at 80° C. or 90° C. in closed 1-ml quartz cuvette. A standard reaction mixture contains 150 mM trisodium substrate, pH 5.0 (at 80° C.), and 0.95 mM pNp derivative pNp=0.561 $mM^{-1}$ $cm^{-1}$). The reaction mixture is allowed to reach the desired temperature, after which the reaction is started by injecting an appropriate amount of enzyme (1.06 ml final volume).

1 U β-glucosidase activity is defined as that amount required to catalyze the formation of 1.0 μmol pNp/min. D-cellobiose may also be used as a substrate.

An ONPG assay for β-galactosidase activity is described by Miller, J. H. (1992) A Short Course in Bacterial Genetics and Mill, J. H. (1992) Experiments in Molecular Genetics, the contents of which are hereby incorporated by reference in their entirety.

A quantitative fluorometric assay for β-galactosidase specific activity is described by: Youngman P., (1987) Plasmid Vectors for Recovering and Exploiting Tn917 Transpositions in *Bacillus* and other Gram-Positive Bacteria. In Plasmids: A Practical approach (ed. K. Hardy) pp 79-103. IRL Press, Oxford. A description of the procedure can be found in Miller (1992) p. 75-77, the contents of which are incorporated by reference herein in their entirety.

The polynucleotides of the present invention may be in the form of DNA which DNA includes cDNA, genomic DNA, and synthetic DNA. The DNA may be double-stranded or single-stranded, and if single stranded may be the coding strand or non-coding (anti-sense) strand. The coding sequences which encodes the mature enzymes may be identical to the coding sequences shown in FIGS. 1-18 (SEQ ID NOS: 1-14 and 57-60) or may be a different coding sequence which coding sequence, as a result of the redundancy or degeneracy of the genetic code, encodes the same mature enzymes as the DNA of FIGS. 1-18 (SEQ ID NOS: 1-14 and 57-60).

The polynucleotide which encodes for the mature enzyme of FIGS. 1-18 (SEQ ID NOS: 15-28 and 61-64) may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence.

The present invention further relates to variants of the hereinabove described polynucleotides which encode for fragments, analogs and derivatives of the enzymes having the deduced amino acid sequences of FIGS. 1-18 (SEQ ID NOS: 15-28 and 61-64). The variant of the polynucleotide may be a naturally occurring allelic variant of the polynucleotide or a non-naturally occurring variant of the polynucleotide.

Thus, the present invention includes polynucleotides encoding the same mature enzymes as shown in FIGS. 1-18 (SEQ ID NOS: 15-28 and 61-64) as well as variants of such polynucleotides which variants encode for a fragment, derivative or analog of the enzymes of FIGS. 1-18 (SEQ ID NOS: 15-28 and 61-64). Such nucleotide variants include deletion variants, substitution variants and addition or insertion variants.

As hereinabove indicated, the polynucleotides may have a coding sequence which is a naturally occurring allelic variant of the coding sequences shown in FIGS. 1-18 (SEQ ID NOS: 1-14 and 57-60). As known in the art, an allelic variant is an alternate form of a polynucleotide sequence which may have a substitution, deletion or addition of one or more nucleotides, which does not substantially alter the function of the encoded enzyme.

Fragments of the full length gene of the present invention may be used as a hybridization probe for a cDNA or a genomic library to isolate the full length DNA and to isolate other DNAs which have a high sequence similarity to the gene or similar biological activity. Probes of this type preferably have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of genomic DNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode enzymes which either retain substantially the same biological function or activity as the mature enzyme encoded by the DNA of FIGS. 1-18 (SEQ ID NOS: 1-14 and 57-60).

Alternatively, the polynucleotide may have at least 15 bases, preferably at least 30 bases, and more preferably at least 50 bases which hybridize to any part of a polynucleotide of the present invention and which has an identity thereto, as hereinabove described, and which may or may not retain activity. For example, such polynucleotides may be employed as probes for the polynucleotides of SEQ ID NOS: 1-14 and 57-60, for example, for recovery of the polynucleotide or as a diagnostic probe or as a PCR primer.

Thus, the present invention is directed to polynucleotides having at least a 70% identity, preferably at least 90% identity and more preferably at least a 95% identity to a polynucleotide which encodes the enzymes of SEQ ID NOS: 15-28 and 61-64 as well as fragments thereof, which fragments have at least 15 bases, preferably at least 30 bases and most preferably at least 50 bases, which fragments are at least 90% identical, preferably at least 95% identical and most preferably at least 97% identical under stringent conditions to any portion of a polynucleotide of the present invention.

The present invention further relates to enzymes which have the deduced amino acid sequences of FIGS. 1-18 (SEQ ID NOS: 15-28 and 61-64) as well as fragments, analogs and derivatives of such enzyme.

The terms "fragment," "derivative" and "analog" when referring to the enzymes of FIGS. 1-18 (SEQ ID NOS: 15-28 and 61-64) means enzymes which retain essentially the same biological function or activity as such enzymes. Thus, an analog includes a proprotein which can be activated by cleavage of the proprotein portion to produce an active mature enzyme.

The enzymes of the present invention may be a recombinant enzyme, a natural enzyme or a synthetic enzyme, preferably a recombinant enzyme.

The fragment, derivative or analog of the enzymes of FIGS. 1-18 (SEQ ID NOS: 15-28 and 61-64) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzymes and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector anchor such polynucleotides or enzymes could be part of a composition, and still be isolated in that such vector or composition is not part of its natural environment.

The enzymes of the present invention include the enzymes of SEQ ID NOS: 15-28 and 61-64 (in particular the mature enzyme) as well as enzymes which have at least 70% similarity (preferably at least 70% identity) to the enzymes of SEQ ID NOS: 15-28 and 61-64 and more preferably at least 90% similarity (more preferably at least 90% identity) to the enzymes of SEQ ID NOS: 15-28 and 61-64 and still more preferably at least 95% similarity (still more preferably at least 95% identity) to the enzymes of SEQ ID NOS: 15-28 and 61-64 and also include portions of such enzymes with such portion of the enzyme generally containing at least 30 amino acids and more preferably at least 50 amino acids.

As known in the art "similarity" between two enzymes is determined by comparing the amino acid sequence and its conserved amino acid substitutes of one enzyme to the sequence of a second enzyme.

A variant, i.e. a "fragment", "analog" or "derivative" polypeptide, and reference polypeptide may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Bacillus subtilis*; fungal cells, such as yeast; insect cells such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pD10, psiX174, pBluescript II KS; pNH8A, pNH16a, pNH18A, pNH46A (Stratagene); ptrc99a, pKK223-3, pKK233-3, pDR540, pRIT5 (Pharmacia); Eukaryotic: pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vectorpBR322 (ATCC 37017). Such commercial vectors include, for example, pKK223-3 (Pharmacia Fine Chemicals, Uppsala, Sweden) and GEMI (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, *Cell,* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

β-galactosidase hydrolyzes lactose to galactose and glucose. Accordingly, the OC1/4V (DNA SEQ ID NO:2, Protein SEQ ID NO:16), 9N2-31B/G (DNA SEQ ID NO:4, Protein SEQ ID NO:18), AEDII12RA-18B/G (DNA SEQ ID NO:6, Protein SEQ ID NO:20) and F1-12G (DNA SEQ ID NO:3, Protein SEQ ID NO:17) enzymes may be employed in the food processing industry for the production of low lactose content milk and for the production of galactose or glucose from lactose contained in whey obtained in a large amount as a by-product in the production of cheese. Generally, it is desired that enzymes used in food processing, such as the aforementioned β-galactosidases, be stable at elevated temperatures to help prevent microbial contamination.

These enzymes may also be employed in the pharmaceutical industry. The enzymes are used to treat intolerance to lactose. In this case, a thermostable enzyme is desired, as well. Thermostable β-galactosidases also have uses in diagnostic applications, where they are employed as reporter molecules.

Glucosidases act on soluble cellooligosaccharides from the non-reducing end to give glucose as the sole product. Glucanases (endo- and exo-) act in the depolymerization of cellulose, generating more non-reducing ends (endo-glucanases, for instance, act on internal linkages yielding cellobiose, glucose and cellooligosaccharides as products). β-glucosidases are used in applications where glucose is the desired product. Accordingly, M11TL-29G (DNA SEQ ID NO:1, Protein SEQ ID NO:15), F1-12G (DNA SEQ ID NO:3, Protein SEQ ID NO:17), GC74-22G (DNA SEQ ID NO:7, Protein SEQ ID NO:21), MSB8-6G (DNA SEQ ID NO:5, Protein SEQ ID NO:19), OC1/4V 33G/B (DNA SEQ ID NO:2, Protein SEQ ID NO:16), OC1/4V 33GP1 (DNA SEQ ID NO:13, Protein SEQ ID NO:27), VC1-7G1 (DNA SEQ ID NO:8, Protein SEQ ID NO:22), 9N2-31B/G (DNA SEQ ID NO:4, Protein SEQ ID NO:18) and AEDII12RA18B/G (DNA SEQ ID NO:6, Protein SEQ ID NO:20) may be employed in a wide variety of industrial applications, including in corn wet milling for the separation of starch and gluten, in the fruit industry for clarification and equipment maintenance, in baking for viscosity reduction, in the textile industry for the processing of blue jeans, and in the detergent industry as an additive. For these and other applications, thermostable enzymes are desirable.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, 1975, Nature, 256:495-497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against the enzyme of the present invention may be used in screening for similar enzymes from other organisms and samples. Such screening techniques are known in the art, for example, one such screening assay is described in "Methods for Measuring Cellulase Activities", *Methods in enzymology*, Vol 160, pp. 87-116, which is hereby incorporated by reference in its entirety.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456-457 (1973).

EXAMPLE 1

Bacterial Expression and Purification of Glycosidase Enzymes

DNA encoding the enzymes of the present invention, SEQ ID NOS: 1-14 and 57-60 were initially amplified from a pBluescript vector containing the DNA by the PCR technique using the primers noted herein. The amplified sequences were then inserted into the respective PQE vector listed beneath the primer sequences, and the enzyme was expressed according to the protocols set forth herein. The 5' and 3' primer sequences for to the respective genes are as follows:

*Thermococcus* AEDII12RA-18B/G

```
                                              (SEQ ID NO: 29)
5'CCGAGAATTCATTAAAGAGGAGAAATTAACTATGGTGAATGCTATGA
TTGTC 3'

                                                SEQ ID NO: 30)
3'CGGAAGATCTTCATAGCTCCGGAAGCCCATA 5'
```

Vector: pQE12; and contains the following restriction enzyme sites 5' EcoRI and 3' Blg II.

OC1/4V-33B/G (SEQ ID NO: 31)
5'CCGAGAATTCATTAAAGAGGAGAAATTAACTATGATAAGAAGGTCCG ATTTTCC 3'

(SEQ ID NO: 32)
3'CGGAAGATCTTTAAGATTTTAGAAATTCCTT 5'

Vector: pQE12; and contains the following restriction enzyme sites 5' EcoRI and 3' Bgl II.

*Thermococcus* 9N2-31B/G (SEQ ID NO: 33)
5'CCGAGAATTCATTAAAGAGGAGAAATTAACTATGCTACCAGAAGGCT TTCTC 3'

(SEQ ID NO: 34)
3'CGGAGGTACCTCACCCAAGTCCGAACTTCTC 5'

Vector: pQE30; and contains the following restriction enzyme sites 5' EcoRI and 3' KpnI.

*Staphylothermus marinus* F1-12G (SEQ ID NO: 35)
5'CCGAGAATTCATTAAAGAGGAGAAATTAACTATGATAAGGTTTCCTG ATTAT 3'

(SEQ ID NO: 36)
3'CGGAAGATCTTTATTCGAGGTTCTTTAATCC 5'

Vector: pQE12; and contains the following restriction enzyme sites 5' EcoRI and 3' Bgl II.

*Thermococcus chitonophagus* GC74-22G (SEQ ID NO: 37)
5'CCGAGAATTCATTCATTAAAGAGGAGAAATTAACTATGCTTCCAGGA GAACTTTCTC 3'

(SEQ ID NO: 38)
3'CGGAGGATCCCTACCCCTCCTCTAAGATCTC 5'

Vector: pQE12; and contains the following restriction enzyme sites 5' EcoRI and 3' BamHI.

M11TL (SEQ ID NO: 39)
5'AATAATCTAGAGCATGCAATTCCCCAAAGACTTCATGATAG 3'

(SEQ ID NO: 40)
3'AATAAAAGCTTACTGGATCAGTGTAAGATGCT 5'

Vector: pQE70; and contains the following restriction enzyme sites 5' SphI and 3' Hind III.

*Thermotoga maritima* MSB8-6G (SEQ ID NO: 41)
5'CCGACAATTGATTAAAGAGGAGAAAATTAACTATGGAAAGGATCGAT GAAATT 3'

(SEQ ID NO: 42)
3'CGGAGGTACCTCATGGTTTGAATCTCTTCTC 5'

Vector: pQE12; and contains the following restriction enzyme sites 5' EcoRI and 3' KpnI.

*Pyrococcus furiosus* VC1-7G1

(SEQ ID NO: 43)
5'CCGACAATTGATTAAAGAGGAGAAATTAACTATGTTCCCTGAAAAGT TCCTT 3'

(SEQ ID NO: 44)
3'CGGAGGTACCTCATCCCCTCAGCAATTCCTC 5'

Vector: pQE12; and contains the following restriction enzyme sites 5' EcoRI and 3' Kpn I.

*Bankia gouldi* Endoglucanase (37GP1)

(SEQ ID NO: 45)
5'AATAAGGATCCGTTTAGCGACGCTCGC 3'

(SEQ ID NO: 46)
3'AATAAAAGCTTCCGGGTTGTACAGCGGTAATAGGC 5'

Vector: pQE52; and contains the following restriction enzyme sites 5' Bam HI and 3' Hind III.

*Thermotoga maritima* α:-galactosidase (6GC2)

(SEQ ID NO: 47)
5'TTTATTGAATTCATTAAAGAGGAGAAATTAACTATGATCTGTGTGGA AATATTCGGAAAG 3'

(SEQ ID NO: 48)
3'TCTATAAAGCTTTCATTCTCTCTCACCCTCTTCGTAGAAG 5'

Vector: pQET; and contains the following restriction enzyme sites 5' EcoRI and 3' Hind III.

*Thermotoga maritima* β-mannanase (6GP2)

(SEQ ID NO: 49)
5'TTTATTCAATTGATTAAAGAGGAGAAATTAACTATGGGGATTGGTGG CGACGAC 3'

(SEQ ID NO: 50)
3'TTTATTAAGCTTATCTTTTCATATTCACATACCTCC 5'

Vector: pQEt; and contains the following restriction enzyme sites 5' Hind III and 3' EcoRI.

AEPII 1α β-mannanase (63 GB1)

(SEQ ID NO: 51)
5'TTTATTGAATTCATTAAAGAGGAGAAATTAACTATGCTACCAGAAGA GTTCCTATGGGGC 3'

(SEQ ID NO: 52)
3'TTATTAAGCTTCTCATCAACGGCTATGGTCTTCATTTC 5'

Vector: pQEt; and contains the following restriction enzyme sites 5' Hind III and 3' EcoRL.

OC1/4V Endoglucanase (33GP1)

(SEQ ID NO: 53)
5'AAAAAACAATTGAATTCATTAAAGAGGAGAAATTAACTATGGTAGAA AGACACTTCAGATATGTT-CTT 3'

(SEQ ID NO: 54)
3'TTTTTCGGATCCAATTCTTCATTTACTCTTTGCCTG 5'

Vector: pQEt; and contains the following restriction enzyme sites 5' BamHI and 3' EcoRI.

*Thermotoga maritima* Pullulanase (6GP3)

```
                                        (SEQ ID NO: 55)
5'TTTTGGAATTCATTAAAGAGGAGAAATTAACTATGGAACTGATCATA
GAAGGTTAC 3'

                                        (SEQ ID NO: 56)
3'ATAAGAAGCTTTTCACTCTCTGTACAGAACGTACGC 5'
```

Vector: pQEt; and contains the following restriction enzyme sites 5' EcoRI and 3' Hind III.

*Thermotoga maritima* MSB8-6GP2

```
                                        (SEQ ID NO: 65)
5'CCGACAATTGATTAAAGAGGAGAAATTAACTATGGAAAGGATCGATG
AAATT 3'

                                        (SEQ ID NO: 66)
3'CGGAGGTACCTCATGGTTTGAATCTCTTCTC 5'
```

Vector: pQE12; and contains the following restriction enzyme sites 5' EcoRI and 3' KpnI.

*Pyrococcus furiosus* VC1-7EG 1

```
                                        (SEQ ID NO: 67)
5'CCGACAATTGATTAAAGAGGAGAAATTAACTATGTTCCCTGAAAAGT
TCCTT 3'

                                        (SEQ ID NO: 68)
3'CGGAGGTACCTCATCCCCTCAGCAATTCCTC 5'
```

Vector: pQE12; and contains the following restriction enzyme sites 5' EcoRI and 3' Kpn I.

*Bankia gouldi* Endoglucanase (37GP4)

```
                                        (SEQ ID NO: 69)
    5'AATAAGGATCCGTTTAGCGACGCTCGC 3'

                                        (SEQ ID NO: 70)
    3'AATAAAAGCTTCCGGGTTGTACAGCGGTAATAGGC 5'
```

Vector: pQE52; and contains the following restriction enzyme sites 5' Bam HI and 3' Hind III.

*Thermotoga maritima* MSB8-6GP4

(SEQ ID NO: 71)

(SEQ ID NO: 72)

Vector: and contains the following restriction enzyme sites 5' and 3'.

The restriction enzyme sites indicated correspond to the restriction enzyme sites on the bacterial expression vector indicated for the respective gene (Qiagen, Inc. Chatsworth, Calif.). The pQE vector encodes antibiotic resistance (Amp$^{\dagger}$), a bacterial origin of replication (ori), an IPTG-regulatable promoter operator (P/O), a ribosome binding site (RBS), a 6-His tag and restriction enzyme sites.

The pQE vector was digested with the restriction enzymes indicated. The amplified sequences were ligated into the respective pQE vector and inserted in frame with the sequence encoding for the RBS. The ligation mixture was then used to transform the *E. coli* strain M15/pREP4 (Qiagen, Inc.) by electroporation. M15/pREP4 contains multiple copies of the plasmid pREP4, which expresses the lacd repressor and also confers kanamycin resistance (Kan$^{\dagger}$). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$_{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation.

The primer sequences set out above may also be employed to isolate the target gene from the deposited material by hybridization techniques described above.

EXAMPLE 2

Isolation of a Selected Clone from the Deposited Genomic Clones

A clone is isolated directly by screening the deposited material using the oligonucleotide primers set forth in Example 1 for the particular gene desired to be isolated. The specific oligonucleotides are synthesized using an Applied Biosystems DNA synthesizer. The oligonucleotides are labeled with $^{32}$P-ATP using T4 polynucleotide kinase and purified according to a standard protocol (Maniatis et al., Molecular Cloning: A Laboratory Manual, Cold Spring Harbor Press, Cold Spring, N.Y., 1982). The deposited clones in the pBluescript vectors may be employed to transform bacterial hosts which are then plated on 1.5% agar plates to the density of 20,000-50,000 pfu/150 mm plate. These plates are screened using Nylon membranes according to the standard screening protocol (Stratagene, 1993). Specifically, the Nylon membrane with denatured and fixed DNA is prehybridized in 6×SSC, 20 mM $NaH_2PO_4$, 0.4% SDS, 5×Denhardt's 500 μg/ml denatured, sonicated salmon sperm DNA; and 6×SSC, 0.1% SDS. After one hour of prehybridization, the membrane is hybridized with hybridization buffer 6×SSC, 20 mM $NaH_2PO_4$, 0.4% SDS, 500 ug/ml denatured, sonicated salmon sperm DNA with $1\times10^6$ cpm/ml $^{32}$P-probe overnight at 42° C. The membrane is washed at 45-50° C. with washing buffer 6×SSC, 0.1% SDS for 20-30 minutes dried and exposed to Kodak X-ray film overnight. Positive clones are isolated and purified by secondary and tertiary screening. The purified clone is sequenced to verify its identity to the primer sequence.

Once the clone is isolated, the two oligonucleotide primers corresponding to the gene of interest are used to amplify the gene from the deposited material. A polymerase chain reaction is carried out in 25 μl of reaction mixture with 0.5 ug of the DNA of the gene of interest. The reaction mixture is 1.5-5 mM $MgCl_2$, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with the Perkin-Elmer Cetus automated thermal cycler. The amplified product is analyzed by agarose gel electrophoresis and the DNA band with expected molecular weight is excised and purified. The PCR product is verified to be the gene of interest by subcloning and sequencing the DNA product. The ends of the newly purified genes are nucleotide sequenced to identify full length sequences. Complete sequencing of full length genes is then performed by Exonuclease III digestion or primer walking.

EXAMPLE 3

Screening for Galactosidase Activity

Screening procedures for ca-galactosidase protein activity may be assayed for as follows:

Substrate plates were provided by a standard plating procedure. Dilute XL1-Blue MRF *E. coli* host of (Stratagene Cloning Systems, La Jolla, Calif.) to $O.D._{600}$=1.0 with NZY media. In 15 ml tubes, inoculate 200 μl diluted host cells with phage. Mix gently and incubate tubes at 37° C. for 15 min. Add approximately 3.5 ml LB top agarose (0.7%) containing 1 mM IPTG to each tube and pour onto all NYZ plate surface. Allow to cool and incubate at 37° C. overnight. The assay plates are obtained as substrate p-Nitrophenyl cc-galactosidase (Sigma) (200 mg/100 ml) (100 mM NaCl, 100 mM Potassium-Phosphate) 1% (w/v) agarose. The plaques are overlayed with nitrocellulose and incubated at 4° C. for 30 minutes whereupon the nitrocellulose is removed and overlayed onto the substrate plates. The substrate plates are then incubated at 70° C. for 20 minutes.

EXAMPLE 4

Screening of Clones for Mannanase Activity

A solid phase screening assay was utilized as a primary screening method to test clones for β-mannanase activity.

A culture solution of the Y1090-*E. coli* host strain (Stratagene Cloning Systems, La Jolla, Calif.) was diluted to $O.D._{600}$=1.0 with NZY media. The amplified library from *Thermotoga maritima* lambda gt11 library was diluted in SM (phage dilution buffer): $5\times10^7$ pfu/μl diluted 1:1000 then 1:100 to $5\times10^2$ pfu/μl. Then 8 μl of phage dilution ($5\times10^2$ pfu/μl) was plated in 200 μl host cells. They were then incubated in 15 ml tubes at 37° C. for 15 minutes.

Approximately 4 ml of molten, LB top agarose (0.7%) at approximately 52° C. was added to each tube and the mixture was poured onto the surface of LB agar plates. The agar plates were then incubated at 37° C. for five hours. The plates were replicated and induced with 10 mM IPTG-soaked Duralon-UV™ nylon membranes (Stratagene Cloning Systems, La Jolla, Calif.) overnight. The nylon membranes and plates were marked with a needle to keep their orientation and the nylon membranes were then removed and stored at 4° C.

An Azo-galactomannan overlay was applied to the LB plates containing the lambda plaques. The overlay contains 1% agarose, 50 mM potassium-phosphate buffer pH 7, 0.4% Azocarob-galactomannan. (Megazyme, Australia). The plates were incubated at 72° C. The Azocarob-galactomannan treated plates were observed after 4 hours then returned to incubation overnight. Putative positives were identified by clearing zones on the Azocarob-galactomannan plates. Two positive clones were observed.

The nylon membranes referred to above, which correspond to the positive clones were retrieved, oriented over the plate and the portions matching the locations of the clearing zones for positive clones were cut out. Phage was eluted from the membrane cut-out portions by soaking the individual portions in 500 μl SM (phage dilution buffer) and 25 μl $CHCl_3$.

EXAMPLE 5

Screening of Clones for Mannosidase Activity

A solid phase screening assay was utilized as a primary screening method to test clones for β-mannosidase activity.

A culture solution of the Y1090-*E. coli* host strain (Stratagene Cloning Systems, La Jolla, Calif.) was diluted to $O.D._{600}$=1.0 with NZY media. The amplified library from AEPII 1a lambda gt11 library was diluted in SM (phage dilution buffer): $5\times10^7$ pfu/μl diluted 1:1000 then 1:100 to $5\times10^2$ pfu/μl. Then 8 μl of phage dilution ($5\times10^2$ pfu/μl) was plated in 200 μl host cells. They were then incubated in 15 ml tubes at 37° C. for 15 minutes.

Approximately 4 ml of molten, LB top agarose (0.7%) at approximately 52° C. was added to each tube and the mixture was poured onto the surface of LB agar plates.

The agar plates were then incubated at 37° C. for five hours. The plates were replicated and induced with 10 mM IPTG-soaked Duralon-UV™ nylon membranes (Stratagene Cloning Systems, La Jolla, Calif.) overnight. The nylon membranes and plates were marked with a needle to keep their orientation and the nylon membranes were then removed and stored at 4° C.

A p-nitrophenyl-β-D-manno-pyranoside overlay was applied to the LB plates containing the lambda plaques. The overlay contains 1% agarose, 50 mM potassium-phosphate buffer pH 7, 0.4% p-nitrophenyl-β-D-manno-pyranoside. (Megazyme, Australia). The plates were incubated at 72° C. The p-nitrophenyl-β-D-manno-p-yranoside treated plates were observed after 4 hours then returned to incubation overnight. Putative positives were identified by clearing zones on the p-nitrophenyl-β-D-manno-pyranoside plates. Two positive clones were observed.

The nylon membranes referred to above, which correspond to the positive clones were retrieved, oriented over the plate and the portions matching the locations of the clearing zones for positive clones were cut out. Phage was eluted from the membrane cut-out portions by soaking the individual portions in 500 μl SM (phage dilution buffer) and 25 μl $CHCl_3$.

EXAMPLE 6

Screening for Pullulanase Activity

Screening procedures for pullulanase protein activity may be assayed for as follows:

Substrate plates were provided by a standard plating procedure. Host cells are diluted to $O.D._{600}$=1.0 with NZY or appropriate media. In 15 ml tubes, inoculate 200 μl diluted host cells with phage. Mix gently and incubate tubes at 37° C. for 15 min. Add approximately 3.5 ml LB top agarose (0.7%) is added to each tube and the mixture is plated, allowed to cool, and incubated at 37° C. for about 28 hours. Overlays of 4.5 mls of the following substrate are poured:

| 100 ml total volume | |
|---|---|
| 0.5 g | Red Pullulan Red (Megazyme, Australia) |
| 1.0 g | Agarose |
| 5 ml | Buffer (Tris-HCL pH 7.2 @ 75° C.) |
| 2 ml | 5M NaCl |
| 5 ml | $CaCl_2$ (100 mM) |
| 85 ml | $dH_2O$ |

Plates are cooled at room temperature, and then incubated at 75° C. for 2 hours. Positives are observed as showing substrate degradation.

EXAMPLE 7

Screening for Endoglucanase Activity

Screening procedures for endoglucanase protein activity may be assayed for as follows:

1. The gene library is plated onto 6 LB/GelRite/0.1% CMC/NZY agar plates (~4,800 plaque forming units/plate) in *E. coli* host with LB agarose as top agarose. The plates are incubated at 37° C. overnight.

2. Plates are chilled at 4° C. for one hour.

3. The plates are overlayed with Duralon membranes (Stratagene) at room temperature for one hour and the membranes are oriented and lifted off the plates and stored at 4° C.

4. The top agarose layer is removed and plates are incubated at 37° C. for ~3 hours.

5. The plate surface is rinsed with NaCl.

6. The plate is stained with 0.1% Congo Red for 15 minutes.

7. The plate is destained with 1M NaCl.

What is claimed is:

1. An isolated, synthetic, or recombinant nucleic acid comprising:

(a) a nucleic acid sequence having at least 90%, 95%, 97%, 99% or complete sequence identity to SEQ ID NO: 13, wherein the nucleic acid encodes a polypeptide having a glycosidase activity or a fragment thereof having glycosidase activity;

(b) a nucleic acid encoding a polypeptide having a glycosidase activity, wherein the polypeptide comprises the sequence of SEQ ID NO: 27 or a fragment thereof having glycosidase activity;

(c) the nucleic acid of (a) or (b) encoding a polypeptide having a glycosidase activity but lacking a native leader sequence; or (d) sequences fully complementary to the nucleic acids of (a) through (c).

2. The isolated, synthetic or recombinant nucleic acid of claim 1, wherein the sequence identity is determined by a sequence comparison algorithm comprising FASTA version 3.0t78 with the default parameters.

3. A method of producing a polypeptide having a glycosidase activity comprising:

(a) introducing the nucleic acid of claim 1 into an isolated host cell, (b) culturing the host cell, (c) expressing from the host cell a polypeptide encoded by said nucleic acid, wherein the polypeptide has glycosidase activity, and (d) isolating the polypeptide.

4. A vector comprising the nucleic acid of claim 1.

5. An isolated host cell comprising the vector of claim 4.

6. A composition comprising the nucleic acid of claim 1.

7. An isolated, synthetic, or recombinant nucleic acid comprising the sequence of SEQ ID NO: 13, wherein the nucleic acid encodes a polypeptide having a glycosidase activity or a fragment thereof having glycosidase activity.

8. An isolated, synthetic, or recombinant nucleic acid comprising a nucleic acid encoding a polypeptide having a glycosidase activity, wherein the polypeptide comprises the sequence of SEQ ID NO: 27 or a fragment thereof having glycosidase activity.

9. The isolated, synthetic or recombinant nucleic acid of claim 1, claim 7 or claim 8, wherein the glycosidase activity comprises:

(a) a glucanase activity, (b) an endoglucanase activity, (c) an exoglucanase activity, (d) a mannanase activity, (e) an activity comprising hydrolysis of a beta-1,4-glycosidic bond, (f) an activity comprising hydrolysis of a cellulose, or (g) generating a glucose, a cellobiose or a cellooligosaccharide.

* * * * *

SEQUENCE LISTING

```
<160> NUMBER OF SEQ ID NOS: 72

<210> SEQ ID NO 1
<211> LENGTH: 1446
<212> TYPE: DNA
<213> ORGANISM: Desulfurococcus sp.

<400> SEQUENCE: 1

ttgaaattcc ccaaagactt catgataggc tactcatctt caccgtttca atttgaagct     60

ggtattcccg ggtccgagga tccgaatagt gattggtggg tatgggtgca tgatccggag    120

aacacagcag ctggactagt cagcggcgat ttcccgaga acggcccagg ttactggaat    180

ttaaaccaaa atgaccacga cctggctgag aagctggggg ttaacactat tagagtaggc    240

gttgagtgga gtaggatttt tccaaagcca actttcaatg ttaaagtccc tgtagagaga    300

gatgagaacg gcagcattgt tcacgtagat gtcgatgata aagcggttga aagacttgat    360

gaattagcca acaaggaggc cgtaaaccat tacgtagaaa tgtataaaga ctgggttgaa    420

agaggtagaa aacttatact caatttatac cattggcccc tgcctctctg gcttcacaac    480

ccaatcatgg tgagaagaat gggcccggac agagcgccct caggctggct taacgaggag    540

tccgtggtgg agtttgccaa atacgccgca tacattgctt ggaaaatggg cgagctacct    600

gttatgtgga gcaccatgaa cgaacccaac gtcgtttatg agcaaggata catgttcgtt    660

aaagggggtt tcccacccgg ctacttgagt ttggaagctg ctgataaggc caggagaaat    720

atgatccagg ctcatgcacg ggcctatgac aatattaaac gcttcagtaa gaaacctgtt    780

ggactaatat acgctttcca atggttcgaa ctattagagg gtccagcaga agtatttgat    840

aagtttaaga gctctaagtt atactatttc acagacatag tatcgaaggg tagttcaatc    900

atcaatgttg aatacaggag agatcttgcc aataggctag actggttggg cgttaactac    960

tatagccgtt tagtctacaa aatcgtcgat gacaaaccta taatcctgca cgggtatgga   1020

ttcctttgta cacctggggg gatcagcccg gctgaaaatc cttgtagcga ttttgggtgg   1080

gaggtgtatc ctgaaggact ctacctactt ctaaaagaac tttacaaccg atacggggta   1140

gacttgatcg tgaccgagaa cggtgtttca gacagcaggg atgcgttgag accggcatac   1200

ctggtctcgc atgtttacag cgtatggaaa gccgctaacg agggcattcc cgtcaaaggc   1260

tacctccact ggagcttgac agacaattac gagtgggccc agggcttcag gcagaaattc   1320

ggtttagtca tggttgactt caaaactaag aaaaggtatc tccgcccaag cgccctagtg   1380

ttccgggaga tcgcaacgca taacggaata ccggatgagc tacagcatct tacactgatc   1440

cagtaa                                                              1446


<210> SEQ ID NO 2
<211> LENGTH: 1317
<212> TYPE: DNA
<213> ORGANISM: Thermotoga sp.

<400> SEQUENCE: 2

atgataagaa ggtccgattt tccaaaagat tttatcttcg gaacggctac ggcagcatac     60
```

-continued

```
cagattgaag gtgcagcaaa cgaagatggc agagggccat caatttggga tgtcttttca    120

cacacgcctg gcaaaaccct gaacggtgac acaggagacg ttgcgtgtga ccattatcac    180

cgatacaagg aagatatcca gctgatgaaa gaaatagggt tagacgctta caggttctct    240

atctcctggc ccagaattat gccagatggg aagaacatca accaaaaggg tgtggatttc    300

tacaacagac tcgttgatga gcttttgaag aatgatatca taccattcgt aacactctat    360

cactgggact taccctacgc actttatgaa aaaggtggat ggcttaaccc agatatagcg    420

ctctatttca gagcatacgc aacgtttatg ttcaacgaac tcggtgatcg tgtgaaacat    480

tggattacac tgaacgaacc atggtgttct tctttctcgg gttattacac gggagagcat    540

gccccgggtc atcaaaattt acaagaagcg ataatcgcgg cgcacaacct gttgagggaa    600

catggacatg ccgtccaggc gtccagagaa gaagtaaaag atggggaagt tggcttaacc    660

aacgttgtga tgaaaataga accgggcgat gcaaaacccg aaagtttctt ggtcgcaagt    720

cttgttgata agttcgttaa tgcatggtcc catgaccctg ttgttttcgg aaaatatccc    780

gaagaagcag ttgcacttta tacggaaaaa gggttgcaag ttctcgatag cgatatgaat    840

attatttcga ctcctataga cttctttggt gtgaattatt acacaagaac acttgttgtt    900

tttgatatga acaatcctct tggattttcg tatgttcagg gagaccttcc caaaacggag    960

atgggatggg aaatctaccc gcagggatta tttgatatgc tggtctatct gaaggaaaga   1020

tataaactac cactttatat cacagagaac gggatggctg gacctgataa attggaaaac   1080

ggaagagttc atgataatta ccgaattgaa tatttggaaa agcactttga aaaagcactt   1140

gaagcaatca atgcagatgt tgatttgaaa ggttacttca tttggtcttt gatggataac   1200

ttcgaatggg cgtgcggata ctccaaacgt ttcggtataa tctacgtaga ttacaatacc   1260

ccaaaaagga tattgaaaga ttcagcgatg tggttgaagg aatttctaaa atcttaa      1317
```

```
<210> SEQ ID NO 3
<211> LENGTH: 1266
<212> TYPE: DNA
<213> ORGANISM: Staphylothermus marinus

<400> SEQUENCE: 3

ttgataaggt ttcctgatta tttcttgttt ggaacagcta catcatcgca ccagatcgag     60

ggtaataaca tatttaatga ttggtgggag tgggagacta aaggcaggat taaggtgaga    120

tcgggtaagg catgtaatca ttgggaactc tataaagaag acatagagct tatggctgag    180

ctgggatata atgcttatag gttctccata gagtggagta gaatatttcc cagaaaagat    240

catatagatt atgagtcgct taataagtat aaggaaatag ttaatctact tagaaaatac    300

gggatagaac ctgtaatcac tcttcaccac ttcacaaacc cgcaatggtt tatgaaaatt    360

ggtggatgga ctagggaaga gaacataaaa tattttataa aatatgtaga acttatagct    420

tccgagataa aagacgtgaa aatatggatc actattaatg aaccaataat atatgtttta    480

caaggatata tttccggcga atggccacct ggaattaaaa atttaaaaat agctgatcaa    540

gtaactaaga atcttttaaa agcacataat gaagcctata atatacttca taaacacggt    600

attgtaggca tagctaaaaa catgatagca tttaaaccag gatctaatag aggaaaagac    660

attaatattt atcataaagt cgataaagca ttcaactggg gatttctcaa cggaatatta    720

aggggagaac tagaaactct ccgtggaaaa taccgagttg agcccggaaa tattgatttc    780

ataggcataa actattattc atcatatatt gtaaaatata cttggaatcc ttttaaacta    840

catattaaag tcgaaccatt agatacaggt ctatggacaa ctatgggtta ctgcatatat    900
```

-continued

```
cctagaggaa tatatgaagt tgtaatgaaa actcatgaga aatacggcaa agaaataatc    960
attacagaga acggtgttgc agtagaaaat gatgaattaa ggattttatc cattatcagg   1020
cacttacaat acttatataa agccatgaat gaaggagcaa aggtgaaagg atatttctac   1080
tggagcttca tggataattt tgagtgggat aaaggattta accaaaggtt cggactagta   1140
gaagttgatt ataagacttt tgagagaaaa cctagaaaaa gcgcatatgt atatagtcaa   1200
atagcacgta ccaagactat aagtgatgaa tacctagaaa aatatggatt aaagaacctc   1260
gaataa                                                              1266
```

<210> SEQ ID NO 4
<211> LENGTH: 1530
<212> TYPE: DNA
<213> ORGANISM: Thermococcus sp.

<400> SEQUENCE: 4

```
atgctaccag aaggctttct ctggggcgtg tcccagtccg gctttcagtt cgagatgggc     60
gacaagctca ggaggaacat tgatccgaac acagactggt ggaagtgggt cagggatccc    120
ttcaacataa agagggaact cgtcagcggc gacctgcccg aggaggggat aaacaactac    180
gaactttacg agaaggatca ccgcctcgcc agagacctcg gtctgaacgt ttacaggatt    240
ggaatagagt ggagcaggat ctttccctgg ccaacgtggt ttgtggaggt tgacgttgag    300
cgggacagct acggactcgt gaaggacgtc aaaatcgata aagacacgct cgaagagctc    360
gacgagatag cgaatcatca ggagatagcc tactaccgcc gcgttataga gcacctcagg    420
gagctgggct tcaaggtcat cgtgaacctc aaccacttca cgctcccccct ctggcttcac    480
gatccgataa tcgcgaggga gaaggccctc accaacggta ggattggctg ggtcgggcag    540
gagagcgtgg tggagttcgc caagtacgcg gcgtacatcg cgaacgcact cggggacctc    600
gttgatatgt ggagcacctt caacgagccg atggtcgttg tggagctcgg ttacctcgcg    660
ccctactccg gctttccgcc gggggttatg aaccccgagg cggcaaagct ggcaatcctc    720
aacatgataa acgcccacgc actggcctac aagatgataa agaagttcga cagggtaaag    780
gccgataagg attcccgctc cgaggccgag gtcgggataa tctacaacaa cataggcgtt    840
gcctatccat acgactccaa cgacccaaag gacgtgaaag ctgcagaaaa cgacaactac    900
ttccacagcg ggctcttctt cgacgcaatc cacaagggca agctcaacat cgagttcgac    960
ggtgagacct tcgtcaaagt tcggcatctc aggggggaacg actggatagg cgttaactac   1020
tacacgagag aagtcgtcag gtattcggag cccaagttcc cgagcatacc cctgatatcc   1080
ttccggggag ttcacaacta cggctacgcc tgcaggcccg ggagttcttc cgccgacgga   1140
aggcccgtaa gcgacatcgg ctgggagatc tatccggagg ggatctacga ctcgataaga   1200
gaggccaaca aatacggggt cccggtttac gtcaccgaaa acggaatagc cgattcaact   1260
gacaccctgc ggccgtacta cctcgcgagc catgtagcga agattgagga ggcgtacgag   1320
gcgggttacg acgtcagggg ctacctctac tgggcgctga ccgacaacta cgagtgggcc   1380
ctcggtttca ggatgaggtt cggcctctat aaagtggatc tcataaccaa ggagagaaca   1440
ccgcgggagg aaagcgtaaa ggtttatagg ggcatcgtgg agaacaacgg agtgagcaag   1500
gaaatccggg agaagttcgg acttgggtga                                    1530
```

<210> SEQ ID NO 5
<211> LENGTH: 2166
<212> TYPE: DNA

-continued

<213> ORGANISM: Thermotoga maritima

<400> SEQUENCE: 5

```
atggaaagga tcgatgaaat tctctctcag ttaactacag aggaaaaggt gaagctcgtt      60
gtgggggttg gtcttccagg actttttggg aacccacatt ccagagtggc gggtgcggct     120
ggagaaacac atcccgttcc aagacttgga attcctgcgt ttgtcctggc agatggtccc     180
gcaggactca gaataaatcc cacaagggaa aacgatgaaa acacttacta cacgacggca     240
tttcccgttg aaatcatgct cgcttctacc tggaacagag accttctgga agaagtggga     300
aaagccatgg gagaagaagt tagggaatac ggtgtcgatg tgcttcttgc acctgcgatg     360
aacattcaca gaaaccctct ttgtggaagg aatttcgagt actactcaga agatcctgtc     420
ctttccggtg aaatggcttc agcctttgtc aagggagttc aatctcaagg ggtgggagcc     480
tgcataaaac actttgtcgc gaacaaccag gaaacgaaca ggatggtagt ggacacgatc     540
gtgtccgagc gagccctcag agaaatatat ctgaaaggtt ttgaaattgc tgtcaagaaa     600
gcaagaccct ggaccgtgat gagcgcttac aacaaactga atggaaaata ctgttcacag     660
aacgaatggc ttttgaagaa ggttctcagg gaagaatggg gatttggcgg tttcgtgatg     720
agcgactggt acgcgggaga caaccctgta gaacagctca aggccggaaa cgatatgatc     780
atgcctggga aagcgtatca ggtgaacaca gaaagaagag atgaaataga agaaatcatg     840
gaggcgttga aggagggaaa attgagtgag gaggttctcg atgagtgtgt gagaaacatt     900
ctcaaagttc ttgtgaacgc gccttccttc aaagggtaca ggtactcaaa caagccggat     960
ctcgaatctc acgcggaagt cgcctacgaa gcaggtgcgg agggtgttgt ccttcttgag    1020
aacaacggtg ttcttccgtt cgatgaaaat acccatgtcg ccgtctttgg caccggtcaa    1080
atcgaaacaa taaagggagg aacgggaagt ggagacaccc atccgagata cacgatctct    1140
atccttgaag gcataaaaga aagaaacatg aagttcgacg aagaactcgc ttccacttat    1200
gaggagtaca taaaaaagat gagagaaaca gaggaatata aacccagaac cgactcttgg    1260
ggaacggtca taaaaccgaa actcccagag aatttcctct cagaaaaaga gataaagaaa    1320
cctccaaaga aaaacgatgt tgcagttgtt gtgatcagta ggatctccgg tgagggatac    1380
gacagaaagc cggtgaaagg tgacttctac ctctccgatg acgagctgga actcataaaa    1440
accgtctcga aagaattcca cgatcagggt aagaaagttg tggttcttct gaacatcgga    1500
agtcccatcg aagtcgcaag ctggagagac cttgtggatg gaattcttct cgtctggcag    1560
gcgggacagg agatgggaag aatagtggcc gatgttcttg tgggaaagat taatccctcc    1620
ggaaaacttc caacgacctt cccgaaggat tactcggacg ttccatcctg gacgttccca    1680
ggagagccaa aggacaatcc gcaaagagtg gtgtacgagg aagacatcta cgtgggatac    1740
aggtactacg acaccttcgg tgtggaacct gcctacgaat tcggctacgg cctctcttac    1800
acaaagtttg aatacaaaga tttaaaaatc gctatcgacg gtgagacgct cagagtgtcg    1860
tacacgatca caaacactgg ggacagagct ggaaaggaag tctcacaggt ctacatcaaa    1920
gctccaaaag gaaaaataga caaacccttc caggagctga aagcgtttca caaaacaaaa    1980
cttttgaacc cgggtgaatc agaagaaatc tccttggaaa ttcctctcag agatcttgcg    2040
agtttcgatg ggaaagaatg ggttgtcgag tcaggagaat acgaggtcag ggtcggtgca    2100
tcttcgaggg atataaggtt gagagatatt tttctggttg agggagagaa gagattcaaa    2160
ccatga                                                               2166
```

-continued

<210> SEQ ID NO 6
<211> LENGTH: 1365
<212> TYPE: DNA
<213> ORGANISM: Thermococcus alcaliphilus

<400> SEQUENCE: 6
atgatccact gcccggttaa agggattata tctgaggctc gcggcataac catcacaata 60
gatttaagtt ttcaaggcca aataaataat ttggtgaatg ctatgattgt ctttccggag 120
ttcttcctct ttggaaccgc cacatcttct catcagatcg agggagataa taaatggaac 180
gactggtggt attatgagga gataggtaag ctcccctaca aatccggtaa agcctgcaat 240
cactgggagc tttacaggga agatatagag ctaatggcac agctcggcta caatgcctac 300
cgcttttcga tagagtggag ccgtctcttc ccggaagagg gcaaattcaa tgaagaagcc 360
ttcaaccgct accgtgaaat aattgaaatc ctccttgaga aggggattac tccaaacgtt 420
acactgcacc acttcacatc accgctgtgg ttcatgcgga agggaggctt tttgaaggaa 480
gaaaacctca agtactggga gcagtacgtt gataaagccg cggagctcct caagggagtc 540
aagcttgtag ctacattcaa cgagccgatg gtctatgtta tgatgggcta cctcacagcc 600
tactggccgc ccttcatcaa gagtcccttt aaagccttta aagttgccgc aaacctcctt 660
aaggcccatg caatggcata tgatatcctc catggtaact ttgatgtggg gatagttaaa 720
aacatcccca taatgctccc tgcaagcaac agagagaaag acgtagaagc tgcccaaaag 780
gcggataacc tctttaactg gaacttcctt gatgcaatat ggagcggaaa atataaagga 840
gcttttggaa cttacaaaac tccagaaagc gatgcagact tcatagggat aaactactac 900
acagccagcg aggtaaggca tagctggaat ccgctaaagt tttcttcga tgccaagctt 960
gcagacttaa gcgagagaaa aacagatatg ggttggagtg tctatccaaa gggcatatac 1020
gaagctatag caaaggtttc acactacgga aagccaatgt acatcacgga aaacgggata 1080
gctaccttag acgatgagtg gaggatagag tttatcatcc agcacctcca gtacgttcac 1140
aaagccttaa acgatggctt tgacttgaga ggctacttct attggtcttt tatggataac 1200
ttcgagtggg ctgagggttt tagaccacgc tttgggctgg tcgaggtgga ctacacgacc 1260
ttcaagagga gaccgagaaa gagtgcttac atatatggag aaattgcaag ggaaaagaaa 1320
ataaaagacg aactgctggc aaagtatggg cttccggagc tatga 1365

<210> SEQ ID NO 7
<211> LENGTH: 1536
<212> TYPE: DNA
<213> ORGANISM: Thermococcus chitonophagus

<400> SEQUENCE: 7
ttgcttccag agaactttct ctggggagtt tcacagtccg gattccagtt tgaaatgggg 60
gacagactga ggaggcacat tgatccaaac acagattggt ggtactgggt aagagatgaa 120
tataatatca aaaaaggact agtaagtggg gatcttcccg aagacggtat aaattcatat 180
gaattatatg agagagacca agaaattgca aaggatttag ggctcaacac atataggatc 240
ggaattgaat ggagcagagt atttccatgg ccaacgactt ttgtcgacgt ggagtatgaa 300
attgatgagt cttacgggtt ggtaaaggat gtgaagattt ctaaagacgc attagaaaaa 360
cttgatgaaa tcgctaacca aagggaaata atatattata ggaacctaat aaattcccta 420
agaaagaggg gttttaaggt aatactaaac ctaaatcatt ttaccctccc aatatggctt 480
catgatccta tcgaatctag agaaaaagcc ctgaccaata agagaaacgg atgggtaagc 540

-continued

```
gaaaggagtg ttatagagtt tgcaaaattt gccgcgtatt tagcatataa attcggagac    600

atagtagaca tgtggagcac atttaatgaa cctatggtgg tcgccgagtt ggggtattta    660

gccccatact caggattccc cccgggagtc atgaatccag aagcagcaaa gttagttatg    720

ctacatatga taaacgccca tgctttagca tataggatga taaagaaatt tgacagaaaa    780

aaagctgatc cagaatcaaa agaaccagct gaaataggaa ttatatacaa taacatcggc    840

gtcacatatc cgtttaatcc gaaagactca aaggatctac aagcatccga taatgccaat    900

ttcttccaca gtgggctatt cttaacggct atccacaggg gaaaattaaa tatcgaattt    960

gacggagaga catttgttta ccttccatat ttaaagggca atgattggct gggagtgaat   1020

tattatacaa gagaagtcgt taaataccaa gatcccatgt ttccaagtat ccctctcata   1080

agcttcaagg gcgttccaga ttatggatac ggatgtagac caggaacgac gtcaaaggac   1140

ggtaatcctg ttagtgacat tggatgggag gtatatccca aaggcatgta cgactctata   1200

gtagctgcca atgaatatgg agttcctgta tacgtaacag aaaacggaat agcagattca   1260

aaagatgtat taaggcccta ttacatcgca tctcacattg aagccatgga agaggcttac   1320

gaaaatggtt atgacgtgag aggatactta cactgggcat taaccgataa ttacgaatgg   1380

gccttagggt tcagaatgag gtttggcttg tacgaagtaa acttgataac caaagagaga   1440

aaacccagga aaaagagtgt aagagtattc agagagatag ttattaataa tgggctaaca   1500

agcaacatca ggaaagagat cttagaggag ggtag                              1536


<210> SEQ ID NO 8
<211> LENGTH: 1533
<212> TYPE: DNA
<213> ORGANISM: Pyrococcus furiosus

<400> SEQUENCE: 8

atgttccctg aaaagttcct ttggggtgtg gcacaatcgg gttttcagtt tgaaatgggg     60

gataaactca ggaggaatat tgacactaac actgattggt ggcactgggt aagggataag    120

acaaatatag agaaaggcct cgttagtgga gatcttcccg aggaggggat taacaattac    180

gagctttatg agaaggacca tgagattgca agaaagctgg gtcttaatgc ttacagaata    240

ggcatagagt ggagcagaat attcccatgg ccaacgacat ttattgatgt tgattatagc    300

tataatgaat catataacct tatagaagat gtaaagatca ccaaggacac tttggaggag    360

ttagatgaga tcgccaacaa gagggaggtg gcctactata ggtcagtcat aaacagcctg    420

aggagcaagg ggtttaaggt tatagttaat ctaaatcact tcacccttcc atattggttg    480

catgatccca ttgaggctag ggagagggcg ttaactaata agaggaacgg ctgggttaac    540

ccaagaacag ttatagagtt tgcaaagtat gccgcttaca tagcctataa gtttggagat    600

atagtggata tgtggagcac gtttaatgag cctatggtgg ttgttgagct tggctaccta    660

gcccccctact ctggcttccc tccaggggtt ctaaatccag aggccgcaaa gctggcgata    720

cttcacatga taaatgcaca tgctttagct tataggcaga taaagaagtt tgacactgag    780

aaagctgata aggattctaa agagcctgca gaagttggta taatttacaa caacattgga    840

gttgcttatc ccaaggatcc gaacgattcc aaggatgtta aggcagcaga aaacgacaac    900

ttcttccact cagggctgtt cttcgaggcc atacacaaag gaaaacttaa tatagagttt    960

gacggtgaaa cgtttataga tgccccctat ctaaagggca atgactggat aggggttaat   1020

tactacacaa gggaagtagt tacgtatcag gaaccaatgt ttccttcaat cccgctgatc   1080

acctttaagg gagttcaagg atatggctat gcctgcagac ctggaactct gtcaaaggat   1140
```

-continued

```
gacagacccg tcagcgacat aggatgggaa ctctatccag aggggatgta cgattcaata   1200

gttgaagctc acaagtacgg cgttccagtt tacgtgacgg agaacggaat agcggattca   1260

aaggacatcc taagacctta ctacatagcg agccacataa agatgataga gaaggccttt   1320

gaggatgggt atgaagttaa gggctacttc cactgggcat taactgacaa cttcgagtgg   1380

gctctcgggt ttagaatgcg ctttggcctc tacgaagtca acctaattac aaaggagaga   1440

attcccaggg agaagagcgt gtcgatattc agagagatag tagccaataa tggtgttacg   1500

aaaaagattg aagaggaatt gctgagggga tga                                1533
```

<210> SEQ ID NO 9
<211> LENGTH: 1614
<212> TYPE: DNA
<213> ORGANISM: Bankia gouldi

<400> SEQUENCE: 9

```
atgagaatac gtttagcgac gctcgcgctc tgcgcagcgc tgagcccagt cacctttgca     60

gataatgtaa ccgtacaaat cgacgccgac ggcggtaaaa aactcatcag ccgagccctt    120

tacggcatga ataactccaa cgcagaaagc cttaccgata ctgactggca gcgttttcgc    180

gatgcaggtg tgcgcatgct gcgggaaaat ggcggcaaca acagcaccaa atataactgg    240

caactgcacc tgagcagtca tccggattgg tacaacaatg tctacgccgg caacaacaac    300

tgggacaacc gggtagccct gattcaggaa aacctgcccg gcgccgacac catgtgggca    360

ttccagctca tcggtaaggt cgcggcgact tctgcctaca actttaacga ttgggaattc    420

aaccagtcgc aatggtggac cggcgtcgct cagaatctcg ctggcggcgg tgaacccaat    480

ctggacggcg gcggcgaagc gctggttgaa ggagacccca atctctacct catggattgg    540

tcgccagccg acactgtggg tattctcgac cactggtttg gcgtaaacgg gctgggcgtg    600

cggcgtggca aagccaaata ctggagtatg gataacgagc ccggcatctg ggttggcacc    660

cacgacgatg tagtgaaaga acaaacgccg gtagaagatt tcctgcacac ctatttcgaa    720

accgccaaaa aagcccgcgc caaatttccc ggtattaaaa tcaccggtcc ggtgcccgct    780

aatgagtggc agtggtatgc ctggggcggt ttctcggtac cccaggaaca agggtttatg    840

agctggatgg agtatttcat caagcgggtg tctgaagagc aacgcgcaag tggtgttcgc    900

ctcctcgatg tactcgatct gcactactac cccggcgctt acaatgcgga agatatcgtg    960

caattacatc gcacgttctt cgaccgcgac tttgtttcac tggatgccaa cggggtgaaa   1020

atggtagaag gtggctggga tgacagcatc aacaaggaat atattttcgg gcgagtgaac   1080

gattggctcg aggaatatat ggggccagac catggtgtaa ccctgggctt aaccgaaatg   1140

tgcgtgcgca atgtgaatcc gatgactacc gccatctggt atgcctccat gctcggcacc   1200

ttcgcggata acggcgtcga aatattcacc ccatggtgct ggaacaccgg aatgtgggaa   1260

acactccacc tcttcagccg ctacaacaaa ccttatcggg tcgcctccag ctccagtctt   1320

gaagagtttg tcagcgccta cagctccatt aacgaagcag aagacgccat gacggtactt   1380

ctggtgaatc gttccactag cgagacccac accgccactg tcgctatcga cgatttccca   1440

ctggatggcc cctaccgcac cctgcgctta cacaacctgc cgggggagga aaccttcgta   1500

tctcaccgag acaacgccct ggaaaaaggt acagtgcgcg ccagcgacaa tacggtaaca   1560

ctggagttgc cccctctgtc cgttactgca atattgctca aggcccggcc ctaa         1614
```

<210> SEQ ID NO 10

-continued

<211> LENGTH: 1668
<212> TYPE: DNA
<213> ORGANISM: Thermotoga maritima

<400> SEQUENCE: 10

```
gtgatctgtg tggaaatatt cggaaagacc ttcagagagg gaagattcgt tctcaaagag     60
aaaaacttca cagttgagtt cgcggtggag aagatacacc ttggctggaa gatctccggc    120
agggtgaagg gaagtccggg aaggcttgag gttcttcgaa cgaaagcacc ggaaaaggta    180
cttgtgaaca actggcagtc ctggggaccg tgcagggtgg tcgatgcctt ttctttcaaa    240
ccacctgaaa tagatccgaa ctggagatac accgcttcgg tggtgcccga tgtacttgaa    300
aggaacctcc agagcgacta tttcgtggct gaagaaggaa aagtgtacgg ttttctgagt    360
tcgaaaatcg cacatccttt cttcgctgtg gaagatgggg aacttgtggc atacctcgaa    420
tatttcgatg tcgagttcga cgactttgtt cctcttgaac ctctcgttgt actcgaggat    480
cccaacacac cccttcttct ggagaaatac gcggaactcg tcggaatgga aaacaacgcg    540
agagttccaa aacacacacc cactggatgg tgcagctggt accattactt ccttgatctc    600
acctgggaag agaccctcaa gaacctgaag ctcgcgaaga atttcccgtt cgaggtcttc    660
cagatagacg acgcctacga aaaggacata ggtgactggc tcgtgacaag aggagacttt    720
ccatcggtgg aagagatggc aaaagttata gcggaaaacg gtttcatccc gggcatatgg    780
accgccccgt tcagtgtttc tgaaacctcg gatgtattca acgaacatcc ggactgggta    840
gtgaaggaaa acggagagcc gaagatggct tacagaaact ggaacaaaaa gatatacgcc    900
ctcgatcttt cgaaagatga ggttctgaac tggctttttcg atctcttctc atctctgaga    960
aagatgggct acaggtactt caagatcgac tttctcttcg cgggtgccgt tccaggagaa   1020
agaaaaaaga acataacacc aattcaggcg ttcagaaaag ggattgagac gatcagaaaa   1080
gcggtgggag aagattcttt catcctcgga tgcggctctc cccttcttcc cgcagtggga   1140
tgcgtcgacg ggatgaggat aggacctgac actgcgccgt tctgggggag acatatagaa   1200
gacaacggag ctcccgctgc aagatgggcg ctgagaaacg ccataacgag gtacttcatg   1260
cacgacaggt tctggctgaa cgaccccgac tgtctgatac tgagagagga gaaaacggat   1320
ctcacacaga aggaaaagga gctctactcg tacacgtgtg gagtgctcga caacatgatc   1380
atagaaagcg atgatctctc gctcgtcaga gatcatggaa aaaaggttct gaaagaaacg   1440
ctcgaactcc tcggtggaag accacgggtt caaaacatca tgtcggagga tctgagatac   1500
gagatcgtct cgtctggcac tctctcagga aacgtcaaga tcgtggtcga tctgaacagc   1560
agagagtacc acctggaaaa agaaggaaag tcctccctga aaaaaagagt cgtcaaaaga   1620
gaagacggaa gaaacttcta cttctacgaa gagggtgaga gagaatga                1668
```

<210> SEQ ID NO 11
<211> LENGTH: 2043
<212> TYPE: DNA
<213> ORGANISM: Thermotoga maritima

<400> SEQUENCE: 11

```
atggggattg gtggcgacga ctcctggagc ccgtcagtat cggcggaatt ccttttattg     60
atcgttgagc tctctttcgt tctctttgca agtgacgagt tcgtgaaagt ggaaaacgga    120
aaattcgctc tgaacggaaa agaattcaga ttcattggaa gcaacaacta ctacatgcac    180
tacaagagca acggaatgat agacagtgtt ctggagagtg ccagagacat gggtataaag    240
gtcctcagaa tctggggttt cctcgacggg gagagttact gcagagacaa gaacacctac    300
```

-continued

```
atgcatcctg agcccggtgt tttcggggtg ccagaaggaa tatcgaacgc ccagagcggt    360

ttcgaaagac tcgactacac agttgcgaaa gcgaaagaac tcggtataaa acttgtcatt    420

gttcttgtga acaactggga cgacttcggt ggaatgaacc agtacgtgag gtggtttgga    480

ggaacccatc acgacgattt ctacagagat gagaagatca aagaagagta caaaaagtac    540

gtctcctttc tcgtaaacca tgtcaatacc tacacgggag ttccttacag ggaagagccc    600

accatcatgg cctgggagct tgcaaacgaa ccgcgctgtg agacggacaa atcggggaac    660

acgctcgttg agtgggtgaa ggagatgagc tcctacataa agagtctgga tcccaaccac    720

ctcgtggctg tgggggacga aggattcttc agcaactacg aaggattcaa accttacggt    780

ggagaagccg agtgggccta caacggctgg tccggtgttg actggaagaa gctcctttcg    840

atagagacgg tggacttcgg cacgttccac ctctatccgt cccactgggg tgtcagtcca    900

gagaactatg cccagtgggg agcgaagtgg atagaagacc acataaagat cgcaaaagag    960

atcggaaaac ccgttgttct ggaagaatat ggaattccaa agagtgcgcc agttaacaga   1020

acggccatct acagactctg gaacgatctg gtctacgatc tcggtggaga tggagcgatg   1080

ttctggatgc tcgcgggaat cggggaaggt tcggacagag acgagagagg gtactatccg   1140

gactacgacg gtttcagaat agtgaacgac gacagtccag aagcggaact gataagagaa   1200

tacgcgaagc tgttcaacac aggtgaagac ataagagaag acacctgctc tttcatcctt   1260

ccaaaagacg gcatggagat caaaaagacc gtggaagtga gggctggtgt tttcgactac   1320

agcaacacgt ttgaaaagtt gtctgtcaaa gtcgaagatc tggtttttga aaatgagata   1380

gagcatctcg gatacggaat ttacggcttt gatctcgaca caacccggat cccggatgga   1440

gaacatgaaa tgttccttga aggccacttt cagggaaaaa cggtgaaaga ctctatcaaa   1500

gcgaaagtgg tgaacgaagc acggtacgtg ctcgcagagg aagttgattt ttcctctcca   1560

gaagaggtga aaaactggtg gaacagcgga acctggcagg cagagttcgg gtcacctgac   1620

attgaatgga acggtgaggt gggaaatgga gcactgcagc tgaacgtgaa actgcccgga   1680

aagagcgact gggaagaagt gagagtagca aggaagttcg aaagactctc agaatgtgag   1740

atcctcgagt acgacatcta cattccaaac gtcgagggac tcaagggaag gttgaggccg   1800

tacgcggttc tgaaccccgg ctgggtgaag ataggcctcg acatgaacaa cgcgaacgtg   1860

gaaagtgcgg agatcatcac tttcggcgga aaagagtaca gaagattcca tgtaagaatt   1920

gagttcgaca gaacagcggg ggtgaaagaa cttcacatag gagttgtcgg tgatcatctg   1980

aggtacgatg gaccgatttt catcgataat gtgagacttt ataaaagaac aggaggtatg   2040

tga                                                                2043
```

<210> SEQ ID NO 12
<211> LENGTH: 1539
<212> TYPE: DNA
<213> ORGANISM: Thermococcus chitonophagus

<400> SEQUENCE: 12

```
atgctaccag aagagttcct atggggcgtt gggcagtcag gctttcagtt cgaaatgggc     60

gacaagctca ggaggcacat cgatccaaat accgactggt ggaagtgggt tcgcgatcct    120

ttcaacataa aaaaggagct tgtgagtggg gaccttcccg aggacggcat caacaactac    180

gaactttttg aaaacgatca caagctcgct aaaggccttg gactcaacgc atacaggatt    240

ggaatagagt ggagcagaat ctttccctgg ccgacgtgga cggtcgatac cgaggtcgag    300
```

-continued

```
ttcgacactt acggtttagt aaaggacgtt aagatagaca agtccaccct tgctgaactc    360

gacaggctgg ccaacaagga ggaggtaatg tactacaggc gcgttattca gcatttgagg    420

gagctcggct tcaaggtctt cgttaacctc aaccacttca cgcttccaat atggctccac    480

gacccgatag tggcaaggga gaaggccctc acaaacgaca gaatcggctg ggtctcccag    540

aggacagttg ttgagtttgc caagtatgct gcttacatcg cccatgcgct cggagacctc    600

gtggacacat ggagcacctt caacgaacct atggtagttg tggagctcgg ctacctcgcc    660

ccctactcag gatttccccc gggagtcatg aaccccgagg ccgcgaagct ggcgatcctc    720

aacatgataa acgcccacgc cttggcatat aagatgataa agaggttcga caccaagaag    780

gccgatgagg atagcaagtc ccctgcggac gttggcataa tttacaacaa catcggtgtt    840

gcctacccta aagaccctaa cgatcccaag gacgttaaag cagccgaaaa cgacaactac    900

ttccacagcg gactgttctt tgatgccatc cacaagggta agctcaacat agagttcgac    960

ggcgaaaact ttgtaaaagt tagacaccta aaaggcaatg actggatagg cctcaactac   1020

tacacccgcg aggttgttag atattcggag cccaagttcc caagtatacc cctcatatcc   1080

ttcaagggcg ttcccaacta cggctactcc tgcaggcccg gcacgacctc cgccgatggc   1140

atgcccgtca gcgatatcgg ctgggaagtc tatccccagg gaatctacga ctcgatagtc   1200

gaggccacca agtacagtgt tcctgtttac gtcaccgaga acggtgttgc ggattccgcg   1260

gacacgctga ggccatacta catagtcagc cacgtctcaa agatagagga agccattgag   1320

aatggatacc ccgtaaaagg ctacatgtac tgggcgctta cggataacta cgagtgggcc   1380

ctcggcttca gcatgaggtt tggtctctac aaggtcgacc tcatctccaa ggagaggatc   1440

ccgagggaga gaagcgttga gatatatcgc aggatagtgc agtccaacgg tgttcctaag   1500

gatatcaaag aggagttcct gaagggtgag gagaaatga                          1539
```

```
<210> SEQ ID NO 13
<211> LENGTH: 1083
<212> TYPE: DNA
<213> ORGANISM: Thermotoga sp.

<400> SEQUENCE: 13

atggtagaaa gacacttcag atatgttctt atttgcaccc tgtttcttgt tatgctccta     60

atctcatcca ctcagtgtgg aaaaaatgaa ccaaacaaaa gagtgaatag catggaacag    120

tcagttgctg aaagtgatag caactcagca tttgaataca acaaaatggt aggtaaagga    180

gtaaatattg gaaatgcttt agaagctcct ttcgaaggag cttggggagt aagaattgag    240

gatgaatatt ttgagataat aaagaaaagg ggatttgatt ctgttaggat tcccataaga    300

tggtcagcac atatatccga aaagccacca tatgatattg acaggaattt cctcgaaaga    360

gttaaccatg ttgtcgatag ggctcttgag aataatttaa cagtaatcat caatacgcac    420

cattttgaag aactctatca agaaccggat aaatacggcg atgttttggt ggaaatttgg    480

agacagattg caaaattctt taaagattac ccggaaaatc tgttctttga aatctacaac    540

gagcctgctc agaacttgac agctgaaaaa tggaacgcac tttatccaaa agtgctcaaa    600

gttatcaggg agagcaatcc aacccggatt gtcattatcg atgctccaaa ctgggcacac    660

tatagcgcag tgagaagtct aaaattagtc aacgacaaac gcatcattgt ttccttccat    720

tactacgaac ctttcaaatt cacacatcag ggtgccgaat gggttaatcc catcccacct    780

gttagggtta agtggaatgg cgaggaatgg gaaattaacc aaatcagaag tcatttcaaa    840

tacgtgagtg actgggcaaa gcaaaataac gtaccaatct ttcttggtga attcggtgct    900
```

-continued

```
tattcaaaag cagacatgga ctcaagggtt aagtggaccg aaagtgtgag aaaaatggcg    960

gaagaatttg gattttcata cgcgtattgg gaattttgtg caggatttgg catatacgat   1020

agatggtctc aaaactggat cgaaccattg gcaacagctg tggttggcac aggcaaagag   1080

taa                                                                 1083
```

<210> SEQ ID NO 14
<211> LENGTH: 2319
<212> TYPE: DNA
<213> ORGANISM: Thermotoga maritima

<400> SEQUENCE: 14

```
atggatctta caaaggtggg gatcatagtg aggctgaacg agtggcaggc aaaagacgtg     60

gcaaaagaca ggttcataga gataaaagac ggaaaggctg aagtgtggat actccaggga    120

gtggaagaga ttttctacga aaaaccagac acatctccca gaatcttctt cgcacaggca    180

aggtcgaaca aggtgatcga ggcttttctg accaatcctg tggatacgaa aaagaaagaa    240

ctcttcaagg ttactgttga cggaaaaagag attcccgtct caagagtgga aaaggccgat    300

cccacggaca tagacgtgac gaactacgtg agaatcgtcc tttctgaatc cctgaaagaa    360

gaagacctca gaaaagacgt ggaactgatc atagaaggtt acaaaccggc aagagtcatc    420

atgatggaga tcctggacga ctactattac gatggagagc tcggagccgt atattctcca    480

gagaagacga tattcagagt ctggtccccc gtttctaagt gggtaaaggt gcttctcttc    540

aaaaacggag aagacacaga accgtaccag gttgtgaaca tggaatacaa gggaaacggg    600

gtctgggaag cggttgttga aggcgatctc gacggagtgt tctacctcta tcagctggaa    660

aactacggaa agatcagaac aaccgtcgat ccttattcga aagcggttta cgcaaacagc    720

aaaaagagcg ccgttgtgaa tcttgccagg acaaacccag aaggatggga aaacgacagg    780

ggaccgaaaa tcgaaggata cgaagacgcg ataatctatg aaatacacat agcggacatc    840

acaggactcg aaaactccgg ggtaaaaaac aaaggcctct atctcgggct caccgaagaa    900

aacacgaaag gaccgggcgg tgtgacaaca ggcctttcgc accttgtgga actcggtgtt    960

acacacgttc atatacttcc tttctttgat ttctacacag gcgacgaact cgataaagat   1020

ttcgagaagt actacaactg gggttacgat ccttacctgt tcatggttcc ggagggcaga   1080

tactcaaccg atcccaaaaa cccacacacg agaatcagag aagtcaaaga aatggtcaaa   1140

gcccttcaca aacacggtat aggtgtgatt atggacatgg tgttccctca cacctacggt   1200

ataggcgaac tctctgcgtt cgatcagacg gtgccgtact acttctacag aatcgacaag   1260

acaggtgcct atttgaacga aagcggatgt ggtaacgtca tcgcaagcga aagacccatg   1320

atgagaaaat tcatagtcga taccgtcacc tactgggtaa aggagtatca catagacgga   1380

ttcaggttcg atcagatggg tctcatcgac aaaaagacaa tgctcgaagt cgaaagagct   1440

cttcataaaa tcgatccaac tatcattctc tacggcgaac cgtggggtgg atggggagca   1500

ccgatcaggt ttggaaagag cgatgtcgcc ggcacacacg tggcagcttt caacgatgag   1560

ttcagagacg caataagggg ttccgtgttc aacccgagcg tcaagggatt cgtcatggga   1620

ggatacggaa aggaaaccaa gatcaaaagg ggtgttgttg gaagcataaa ctacgacgga   1680

aaactcatca aaagtctcgc ccttgatcca gaagaaacta taaactacgc agcgtgtcac   1740

gacaaccaca cactgtggga caagaactac cttgccgcca aagctgataa gaaaaaggaa   1800

tggaccgaag aagaactgaa aaacgcccag aaactggctg gtgcgatact tctcacttct   1860
```

-continued

```
caaggtgttc ctttcctcca cggagggcag gacttctgca ggacgaagaa tttcaacgac   1920

aactcctaca acgcccctat ctcgataaac ggcttcgatt acgaaagaaa acttcagttc   1980

atagacgtgt tcaattacca caagggtctc ataaaactca gaaaagaaca ccctgctttc   2040

aggctgaaaa acgctgaaga gatcaaaaaa cacctggaat ttctcccggg cgggagaaga   2100

atagttgcgt tcatgcttaa agaccacgca ggtggtgatc cctggaaaga catcgtggtg   2160

atttacaatg gaaacttaga gaagacaaca tacaaactgc cagaaggaaa atggaatgtg   2220

gttgtgaaca gccagaaagc cggaacagaa gtgatagaaa ccgtcgaagg aacaatagaa   2280

ctcgatccgc tttccgcgta cgttctgtac agagagtga                          2319


<210> SEQ ID NO 15
<211> LENGTH: 481
<212> TYPE: PRT
<213> ORGANISM: Desulfurococcus sp.

<400> SEQUENCE: 15

Leu Lys Phe Pro Lys Asp Phe Met Ile Gly Tyr Ser Ser Ser Pro Phe
 1               5                   10                  15

Gln Phe Glu Ala Gly Ile Pro Gly Ser Glu Asp Pro Asn Ser Asp Trp
            20                  25                  30

Trp Val Trp Val His Asp Pro Glu Asn Thr Ala Ala Gly Leu Val Ser
        35                  40                  45

Gly Asp Phe Pro Glu Asn Gly Pro Gly Tyr Trp Asn Leu Asn Gln Asn
    50                  55                  60

Asp His Asp Leu Ala Glu Lys Leu Gly Val Asn Thr Ile Arg Val Gly
65                  70                  75                  80

Val Glu Trp Ser Arg Ile Phe Pro Lys Pro Thr Phe Asn Val Lys Val
                85                  90                  95

Pro Val Glu Arg Asp Glu Asn Gly Ser Ile Val His Val Asp Val Asp
            100                 105                 110

Asp Lys Ala Val Glu Arg Leu Asp Glu Leu Ala Asn Lys Glu Ala Val
        115                 120                 125

Asn His Tyr Val Glu Met Tyr Lys Asp Trp Val Glu Arg Gly Arg Lys
    130                 135                 140

Leu Ile Leu Asn Leu Tyr His Trp Pro Leu Pro Leu Trp Leu His Asn
145                 150                 155                 160

Pro Ile Met Val Arg Arg Met Gly Pro Asp Arg Ala Pro Ser Gly Trp
                165                 170                 175

Leu Asn Glu Glu Ser Val Val Glu Phe Ala Lys Tyr Ala Ala Tyr Ile
            180                 185                 190

Ala Trp Lys Met Gly Glu Leu Pro Val Met Trp Ser Thr Met Asn Glu
        195                 200                 205

Pro Asn Val Val Tyr Glu Gln Gly Tyr Met Phe Val Lys Gly Gly Phe
    210                 215                 220

Pro Pro Gly Tyr Leu Ser Leu Glu Ala Ala Asp Lys Ala Arg Arg Asn
225                 230                 235                 240

Met Ile Gln Ala His Ala Arg Ala Tyr Asp Asn Ile Lys Arg Phe Ser
                245                 250                 255

Lys Lys Pro Val Gly Leu Ile Tyr Ala Phe Gln Trp Phe Glu Leu Leu
            260                 265                 270

Glu Gly Pro Ala Glu Val Phe Asp Lys Phe Lys Ser Ser Lys Leu Tyr
        275                 280                 285

Tyr Phe Thr Asp Ile Val Ser Lys Gly Ser Ser Ile Ile Asn Val Glu
```

```
    290                 295                 300

Tyr Arg Arg Asp Leu Ala Asn Arg Leu Asp Trp Leu Gly Val Asn Tyr
305                 310                 315                 320

Tyr Ser Arg Leu Val Tyr Lys Ile Val Asp Asp Lys Pro Ile Ile Leu
                325                 330                 335

His Gly Tyr Gly Phe Leu Cys Thr Pro Gly Gly Ile Ser Pro Ala Glu
            340                 345                 350

Asn Pro Cys Ser Asp Phe Gly Trp Glu Val Tyr Pro Glu Gly Leu Tyr
        355                 360                 365

Leu Leu Leu Lys Glu Leu Tyr Asn Arg Tyr Gly Val Asp Leu Ile Val
    370                 375                 380

Thr Glu Asn Gly Val Ser Asp Ser Arg Asp Ala Leu Arg Pro Ala Tyr
385                 390                 395                 400

Leu Val Ser His Val Tyr Ser Val Trp Lys Ala Ala Asn Glu Gly Ile
                405                 410                 415

Pro Val Lys Gly Tyr Leu His Trp Ser Leu Thr Asp Asn Tyr Glu Trp
            420                 425                 430

Ala Gln Gly Phe Arg Gln Lys Phe Gly Leu Val Met Val Asp Phe Lys
        435                 440                 445

Thr Lys Lys Arg Tyr Leu Arg Pro Ser Ala Leu Val Phe Arg Glu Ile
    450                 455                 460

Ala Thr His Asn Gly Ile Pro Asp Glu Leu Gln His Leu Thr Leu Ile
465                 470                 475                 480

Gln


<210> SEQ ID NO 16
<211> LENGTH: 438
<212> TYPE: PRT
<213> ORGANISM: Thermotoga sp.

<400> SEQUENCE: 16

Met Ile Arg Arg Ser Asp Phe Pro Lys Asp Phe Ile Phe Gly Thr Ala
 1               5                  10                  15

Thr Ala Ala Tyr Gln Ile Glu Gly Ala Ala Asn Glu Asp Gly Arg Gly
            20                  25                  30

Pro Ser Ile Trp Asp Val Phe Ser His Thr Pro Gly Lys Thr Leu Asn
        35                  40                  45

Gly Asp Thr Gly Asp Val Ala Cys Asp His Tyr His Arg Tyr Lys Glu
    50                  55                  60

Asp Ile Gln Leu Met Lys Glu Ile Gly Leu Asp Ala Tyr Arg Phe Ser
65                  70                  75                  80

Ile Ser Trp Pro Arg Ile Met Pro Asp Gly Lys Asn Ile Asn Gln Lys
                85                  90                  95

Gly Val Asp Phe Tyr Asn Arg Leu Val Asp Glu Leu Leu Lys Asn Asp
            100                 105                 110

Ile Ile Pro Phe Val Thr Leu Tyr His Trp Asp Leu Pro Tyr Ala Leu
        115                 120                 125

Tyr Glu Lys Gly Gly Trp Leu Asn Pro Asp Ile Ala Leu Tyr Phe Arg
    130                 135                 140

Ala Tyr Ala Thr Phe Met Phe Asn Glu Leu Gly Asp Arg Val Lys His
145                 150                 155                 160

Trp Ile Thr Leu Asn Glu Pro Trp Cys Ser Ser Phe Ser Gly Tyr Tyr
                165                 170                 175

Thr Gly Glu His Ala Pro Gly His Gln Asn Leu Gln Glu Ala Ile Ile
```

-continued

```
            180                 185                 190

Ala Ala His Asn Leu Leu Arg Glu His Gly His Ala Val Gln Ala Ser
        195                 200                 205

Arg Glu Glu Val Lys Asp Gly Glu Val Gly Leu Thr Asn Val Val Met
    210                 215                 220

Lys Ile Glu Pro Gly Asp Ala Lys Pro Glu Ser Phe Leu Val Ala Ser
225                 230                 235                 240

Leu Val Asp Lys Phe Val Asn Ala Trp Ser His Asp Pro Val Val Phe
                245                 250                 255

Gly Lys Tyr Pro Glu Glu Ala Val Ala Leu Tyr Thr Glu Lys Gly Leu
            260                 265                 270

Gln Val Leu Asp Ser Asp Met Asn Ile Ile Ser Thr Pro Ile Asp Phe
        275                 280                 285

Phe Gly Val Asn Tyr Tyr Thr Arg Thr Leu Val Val Phe Asp Met Asn
    290                 295                 300

Asn Pro Leu Gly Phe Ser Tyr Val Gln Gly Asp Leu Pro Lys Thr Glu
305                 310                 315                 320

Met Gly Trp Glu Ile Tyr Pro Gln Gly Leu Phe Asp Met Leu Val Tyr
                325                 330                 335

Leu Lys Glu Arg Tyr Lys Leu Pro Leu Tyr Ile Thr Glu Asn Gly Met
            340                 345                 350

Ala Gly Pro Asp Lys Leu Glu Asn Gly Arg Val His Asp Asn Tyr Arg
        355                 360                 365

Ile Glu Tyr Leu Glu Lys His Phe Glu Lys Ala Leu Glu Ala Ile Asn
    370                 375                 380

Ala Asp Val Asp Leu Lys Gly Tyr Phe Ile Trp Ser Leu Met Asp Asn
385                 390                 395                 400

Phe Glu Trp Ala Cys Gly Tyr Ser Lys Arg Phe Gly Ile Ile Tyr Val
                405                 410                 415

Asp Tyr Asn Thr Pro Lys Arg Ile Leu Lys Asp Ser Ala Met Trp Leu
            420                 425                 430

Lys Glu Phe Leu Lys Ser
        435


<210> SEQ ID NO 17
<211> LENGTH: 421
<212> TYPE: PRT
<213> ORGANISM: Staphylothermus marinus

<400> SEQUENCE: 17

Leu Ile Arg Phe Pro Asp Tyr Phe Leu Phe Gly Thr Ala Thr Ser Ser
 1               5                  10                  15

His Gln Ile Glu Gly Asn Asn Ile Phe Asn Asp Trp Trp Glu Trp Glu
            20                  25                  30

Thr Lys Gly Arg Ile Lys Val Arg Ser Gly Lys Ala Cys Asn His Trp
        35                  40                  45

Glu Leu Tyr Lys Glu Asp Ile Glu Leu Met Ala Glu Leu Gly Tyr Asn
    50                  55                  60

Ala Tyr Arg Phe Ser Ile Glu Trp Ser Arg Ile Phe Pro Arg Lys Asp
65                  70                  75                  80

His Ile Asp Tyr Glu Ser Leu Asn Lys Tyr Lys Glu Ile Val Asn Leu
                85                  90                  95

Leu Arg Lys Tyr Gly Ile Glu Pro Val Ile Thr Leu His His Phe Thr
            100                 105                 110
```

-continued

```
Asn Pro Gln Trp Phe Met Lys Ile Gly Gly Trp Thr Arg Glu Glu Asn
        115                 120                 125

Ile Lys Tyr Phe Ile Lys Tyr Val Glu Leu Ile Ala Ser Glu Ile Lys
    130                 135                 140

Asp Val Lys Ile Trp Ile Thr Ile Asn Glu Pro Ile Ile Tyr Val Leu
145                 150                 155                 160

Gln Gly Tyr Ile Ser Gly Glu Trp Pro Pro Gly Ile Lys Asn Leu Lys
                165                 170                 175

Ile Ala Asp Gln Val Thr Lys Asn Leu Leu Lys Ala His Asn Glu Ala
            180                 185                 190

Tyr Asn Ile Leu His Lys His Gly Ile Val Gly Ile Ala Lys Asn Met
        195                 200                 205

Ile Ala Phe Lys Pro Gly Ser Asn Arg Gly Lys Asp Ile Asn Ile Tyr
    210                 215                 220

His Lys Val Asp Lys Ala Phe Asn Trp Gly Phe Leu Asn Gly Ile Leu
225                 230                 235                 240

Arg Gly Glu Leu Glu Thr Leu Arg Gly Lys Tyr Arg Val Glu Pro Gly
                245                 250                 255

Asn Ile Asp Phe Ile Gly Ile Asn Tyr Tyr Ser Ser Tyr Ile Val Lys
            260                 265                 270

Tyr Thr Trp Asn Pro Phe Lys Leu His Ile Lys Val Glu Pro Leu Asp
        275                 280                 285

Thr Gly Leu Trp Thr Thr Met Gly Tyr Cys Ile Tyr Pro Arg Gly Ile
    290                 295                 300

Tyr Glu Val Val Met Lys Thr His Glu Lys Tyr Gly Lys Glu Ile Ile
305                 310                 315                 320

Ile Thr Glu Asn Gly Val Ala Val Glu Asn Asp Glu Leu Arg Ile Leu
                325                 330                 335

Ser Ile Ile Arg His Leu Gln Tyr Leu Tyr Lys Ala Met Asn Glu Gly
            340                 345                 350

Ala Lys Val Lys Gly Tyr Phe Tyr Trp Ser Phe Met Asp Asn Phe Glu
        355                 360                 365

Trp Asp Lys Gly Phe Asn Gln Arg Phe Gly Leu Val Glu Val Asp Tyr
    370                 375                 380

Lys Thr Phe Glu Arg Lys Pro Arg Lys Ser Ala Tyr Val Tyr Ser Gln
385                 390                 395                 400

Ile Ala Arg Thr Lys Thr Ile Ser Asp Glu Tyr Leu Glu Lys Tyr Gly
                405                 410                 415

Leu Lys Asn Leu Glu
            420


<210> SEQ ID NO 18
<211> LENGTH: 509
<212> TYPE: PRT
<213> ORGANISM: Thermococcus sp.

<400> SEQUENCE: 18

Met Leu Pro Glu Gly Phe Leu Trp Gly Val Ser Gln Ser Gly Phe Gln
 1               5                  10                  15

Phe Glu Met Gly Asp Lys Leu Arg Arg Asn Ile Asp Pro Asn Thr Asp
            20                  25                  30

Trp Trp Lys Trp Val Arg Asp Pro Phe Asn Ile Lys Arg Glu Leu Val
        35                  40                  45

Ser Gly Asp Leu Pro Glu Glu Gly Ile Asn Asn Tyr Glu Leu Tyr Glu
    50                  55                  60
```

-continued

```
Lys Asp His Arg Leu Ala Arg Asp Leu Gly Leu Asn Val Tyr Arg Ile
65                  70                  75                  80

Gly Ile Glu Trp Ser Arg Ile Phe Pro Trp Pro Thr Trp Phe Val Glu
                85                  90                  95

Val Asp Val Glu Arg Asp Ser Tyr Gly Leu Val Lys Asp Val Lys Ile
            100                 105                 110

Asp Lys Asp Thr Leu Glu Glu Leu Asp Glu Ile Ala Asn His Gln Glu
        115                 120                 125

Ile Ala Tyr Tyr Arg Arg Val Ile Glu His Leu Arg Glu Leu Gly Phe
    130                 135                 140

Lys Val Ile Val Asn Leu Asn His Phe Thr Leu Pro Leu Trp Leu His
145                 150                 155                 160

Asp Pro Ile Ile Ala Arg Glu Lys Ala Leu Thr Asn Gly Arg Ile Gly
                165                 170                 175

Trp Val Gly Gln Glu Ser Val Val Glu Phe Ala Lys Tyr Ala Ala Tyr
            180                 185                 190

Ile Ala Asn Ala Leu Gly Asp Leu Val Asp Met Trp Ser Thr Phe Asn
        195                 200                 205

Glu Pro Met Val Val Val Glu Leu Gly Tyr Leu Ala Pro Tyr Ser Gly
    210                 215                 220

Phe Pro Pro Gly Val Met Asn Pro Glu Ala Ala Lys Leu Ala Ile Leu
225                 230                 235                 240

Asn Met Ile Asn Ala His Ala Leu Ala Tyr Lys Met Ile Lys Lys Phe
                245                 250                 255

Asp Arg Val Lys Ala Asp Lys Asp Ser Arg Ser Glu Ala Glu Val Gly
            260                 265                 270

Ile Ile Tyr Asn Asn Ile Gly Val Ala Tyr Pro Tyr Asp Ser Asn Asp
        275                 280                 285

Pro Lys Asp Val Lys Ala Ala Glu Asn Asp Asn Tyr Phe His Ser Gly
    290                 295                 300

Leu Phe Phe Asp Ala Ile His Lys Gly Lys Leu Asn Ile Glu Phe Asp
305                 310                 315                 320

Gly Glu Thr Phe Val Lys Val Arg His Leu Arg Gly Asn Asp Trp Ile
                325                 330                 335

Gly Val Asn Tyr Tyr Thr Arg Glu Val Val Arg Tyr Ser Glu Pro Lys
            340                 345                 350

Phe Pro Ser Ile Pro Leu Ile Ser Phe Arg Gly Val His Asn Tyr Gly
        355                 360                 365

Tyr Ala Cys Arg Pro Gly Ser Ser Ser Ala Asp Gly Arg Pro Val Ser
    370                 375                 380

Asp Ile Gly Trp Glu Ile Tyr Pro Glu Gly Ile Tyr Asp Ser Ile Arg
385                 390                 395                 400

Glu Ala Asn Lys Tyr Gly Val Pro Val Tyr Val Thr Glu Asn Gly Ile
                405                 410                 415

Ala Asp Ser Thr Asp Thr Leu Arg Pro Tyr Tyr Leu Ala Ser His Val
            420                 425                 430

Ala Lys Ile Glu Glu Ala Tyr Glu Ala Gly Tyr Asp Val Arg Gly Tyr
        435                 440                 445

Leu Tyr Trp Ala Leu Thr Asp Asn Tyr Glu Trp Ala Leu Gly Phe Arg
    450                 455                 460

Met Arg Phe Gly Leu Tyr Lys Val Asp Leu Ile Thr Lys Glu Arg Thr
465                 470                 475                 480
```

-continued

```
Pro Arg Glu Glu Ser Val Lys Val Tyr Arg Gly Ile Val Glu Asn Asn
                485                 490                 495

Gly Val Ser Lys Glu Ile Arg Glu Lys Phe Gly Leu Gly
            500                 505


<210> SEQ ID NO 19
<211> LENGTH: 721
<212> TYPE: PRT
<213> ORGANISM: Thermotoga maritima

<400> SEQUENCE: 19

Met Glu Arg Ile Asp Glu Ile Leu Ser Gln Leu Thr Thr Glu Glu Lys
 1               5                  10                  15

Val Lys Leu Val Val Gly Val Gly Leu Pro Gly Leu Phe Gly Asn Pro
            20                  25                  30

His Ser Arg Val Ala Gly Ala Ala Gly Glu Thr His Pro Val Pro Arg
        35                  40                  45

Leu Gly Ile Pro Ala Phe Val Leu Ala Asp Gly Pro Ala Gly Leu Arg
    50                  55                  60

Ile Asn Pro Thr Arg Glu Asn Asp Glu Asn Thr Tyr Tyr Thr Thr Ala
65                  70                  75                  80

Phe Pro Val Glu Ile Met Leu Ala Ser Thr Trp Asn Arg Asp Leu Leu
                85                  90                  95

Glu Glu Val Gly Lys Ala Met Gly Glu Glu Val Arg Glu Tyr Gly Val
            100                 105                 110

Asp Val Leu Leu Ala Pro Ala Met Asn Ile His Arg Asn Pro Leu Cys
        115                 120                 125

Gly Arg Asn Phe Glu Tyr Tyr Ser Glu Asp Pro Val Leu Ser Gly Glu
    130                 135                 140

Met Ala Ser Ala Phe Val Lys Gly Val Gln Ser Gln Gly Val Gly Ala
145                 150                 155                 160

Cys Ile Lys His Phe Val Ala Asn Asn Gln Glu Thr Asn Arg Met Val
                165                 170                 175

Val Asp Thr Ile Val Ser Glu Arg Ala Leu Arg Glu Ile Tyr Leu Lys
            180                 185                 190

Gly Phe Glu Ile Ala Val Lys Lys Ala Arg Pro Trp Thr Val Met Ser
        195                 200                 205

Ala Tyr Asn Lys Leu Asn Gly Lys Tyr Cys Ser Gln Asn Glu Trp Leu
    210                 215                 220

Leu Lys Lys Val Leu Arg Glu Glu Trp Gly Phe Gly Gly Phe Val Met
225                 230                 235                 240

Ser Asp Trp Tyr Ala Gly Asp Asn Pro Val Glu Gln Leu Lys Ala Gly
                245                 250                 255

Asn Asp Met Ile Met Pro Gly Lys Ala Tyr Gln Val Asn Thr Glu Arg
            260                 265                 270

Arg Asp Glu Ile Glu Glu Ile Met Glu Ala Leu Lys Glu Gly Lys Leu
        275                 280                 285

Ser Glu Glu Val Leu Asp Glu Cys Val Arg Asn Ile Leu Lys Val Leu
    290                 295                 300

Val Asn Ala Pro Ser Phe Lys Gly Tyr Arg Tyr Ser Asn Lys Pro Asp
305                 310                 315                 320

Leu Glu Ser His Ala Glu Val Ala Tyr Glu Ala Gly Ala Glu Gly Val
                325                 330                 335

Val Leu Leu Glu Asn Asn Gly Val Leu Pro Phe Asp Glu Asn Thr His
            340                 345                 350
```

-continued

```
Val Ala Val Phe Gly Thr Gly Gln Ile Glu Thr Ile Lys Gly Gly Thr
        355                 360                 365

Gly Ser Gly Asp Thr His Pro Arg Tyr Thr Ile Ser Ile Leu Glu Gly
    370                 375                 380

Ile Lys Glu Arg Asn Met Lys Phe Asp Glu Glu Leu Ala Ser Thr Tyr
385                 390                 395                 400

Glu Glu Tyr Ile Lys Lys Met Arg Glu Thr Glu Glu Tyr Lys Pro Arg
                405                 410                 415

Thr Asp Ser Trp Gly Thr Val Ile Lys Pro Lys Leu Pro Glu Asn Phe
            420                 425                 430

Leu Ser Glu Lys Glu Ile Lys Lys Pro Pro Lys Lys Asn Asp Val Ala
        435                 440                 445

Val Val Val Ile Ser Arg Ile Ser Gly Glu Gly Tyr Asp Arg Lys Pro
    450                 455                 460

Val Lys Gly Asp Phe Tyr Leu Ser Asp Asp Glu Leu Glu Leu Ile Lys
465                 470                 475                 480

Thr Val Ser Lys Glu Phe His Asp Gln Gly Lys Lys Val Val Val Leu
                485                 490                 495

Leu Asn Ile Gly Ser Pro Ile Glu Val Ala Ser Trp Arg Asp Leu Val
            500                 505                 510

Asp Gly Ile Leu Leu Val Trp Gln Ala Gly Gln Glu Met Gly Arg Ile
        515                 520                 525

Val Ala Asp Val Leu Val Gly Lys Ile Asn Pro Ser Gly Lys Leu Pro
    530                 535                 540

Thr Thr Phe Pro Lys Asp Tyr Ser Asp Val Pro Ser Trp Thr Phe Pro
545                 550                 555                 560

Gly Glu Pro Lys Asp Asn Pro Gln Arg Val Val Tyr Glu Glu Asp Ile
                565                 570                 575

Tyr Val Gly Tyr Arg Tyr Tyr Asp Thr Phe Gly Val Glu Pro Ala Tyr
            580                 585                 590

Glu Phe Gly Tyr Gly Leu Ser Tyr Thr Lys Phe Glu Tyr Lys Asp Leu
        595                 600                 605

Lys Ile Ala Ile Asp Gly Glu Thr Leu Arg Val Ser Tyr Thr Ile Thr
    610                 615                 620

Asn Thr Gly Asp Arg Ala Gly Lys Glu Val Ser Gln Val Tyr Ile Lys
625                 630                 635                 640

Ala Pro Lys Gly Lys Ile Asp Lys Pro Phe Gln Glu Leu Lys Ala Phe
                645                 650                 655

His Lys Thr Lys Leu Leu Asn Pro Gly Glu Ser Glu Glu Ile Ser Leu
            660                 665                 670

Glu Ile Pro Leu Arg Asp Leu Ala Ser Phe Asp Gly Lys Glu Trp Val
        675                 680                 685

Val Glu Ser Gly Glu Tyr Glu Val Arg Val Gly Ala Ser Ser Arg Asp
    690                 695                 700

Ile Arg Leu Arg Asp Ile Phe Leu Val Glu Gly Glu Lys Arg Phe Lys
705                 710                 715                 720

Pro
```

<210> SEQ ID NO 20
<211> LENGTH: 454
<212> TYPE: PRT
<213> ORGANISM: Thermococcus alcaliphilus

<400> SEQUENCE: 20

-continued

```
Met Ile His Cys Pro Val Lys Gly Ile Ile Ser Glu Ala Arg Gly Ile
 1               5                  10                  15

Thr Ile Thr Ile Asp Leu Ser Phe Gln Gly Gln Ile Asn Asn Leu Val
            20                  25                  30

Asn Ala Met Ile Val Phe Pro Glu Phe Phe Leu Phe Gly Thr Ala Thr
        35                  40                  45

Ser Ser His Gln Ile Glu Gly Asp Asn Lys Trp Asn Asp Trp Trp Tyr
    50                  55                  60

Tyr Glu Glu Ile Gly Lys Leu Pro Tyr Lys Ser Gly Lys Ala Cys Asn
65                  70                  75                  80

His Trp Glu Leu Tyr Arg Glu Asp Ile Glu Leu Met Ala Gln Leu Gly
                85                  90                  95

Tyr Asn Ala Tyr Arg Phe Ser Ile Glu Trp Ser Arg Leu Phe Pro Glu
            100                 105                 110

Glu Gly Lys Phe Asn Glu Glu Ala Phe Asn Arg Tyr Arg Glu Ile Ile
        115                 120                 125

Glu Ile Leu Leu Glu Lys Gly Ile Thr Pro Asn Val Thr Leu His His
    130                 135                 140

Phe Thr Ser Pro Leu Trp Phe Met Arg Lys Gly Gly Phe Leu Lys Glu
145                 150                 155                 160

Glu Asn Leu Lys Tyr Trp Glu Gln Tyr Val Asp Lys Ala Ala Glu Leu
                165                 170                 175

Leu Lys Gly Val Lys Leu Val Ala Thr Phe Asn Glu Pro Met Val Tyr
            180                 185                 190

Val Met Met Gly Tyr Leu Thr Ala Tyr Trp Pro Pro Phe Ile Lys Ser
        195                 200                 205

Pro Phe Lys Ala Phe Lys Val Ala Ala Asn Leu Leu Lys Ala His Ala
    210                 215                 220

Met Ala Tyr Asp Ile Leu His Gly Asn Phe Asp Val Gly Ile Val Lys
225                 230                 235                 240

Asn Ile Pro Ile Met Leu Pro Ala Ser Asn Arg Glu Lys Asp Val Glu
                245                 250                 255

Ala Ala Gln Lys Ala Asp Asn Leu Phe Asn Trp Asn Phe Leu Asp Ala
            260                 265                 270

Ile Trp Ser Gly Lys Tyr Lys Gly Ala Phe Gly Thr Tyr Lys Thr Pro
        275                 280                 285

Glu Ser Asp Ala Asp Phe Ile Gly Ile Asn Tyr Tyr Thr Ala Ser Glu
    290                 295                 300

Val Arg His Ser Trp Asn Pro Leu Lys Phe Phe Phe Asp Ala Lys Leu
305                 310                 315                 320

Ala Asp Leu Ser Glu Arg Lys Thr Asp Met Gly Trp Ser Val Tyr Pro
                325                 330                 335

Lys Gly Ile Tyr Glu Ala Ile Ala Lys Val Ser His Tyr Gly Lys Pro
            340                 345                 350

Met Tyr Ile Thr Glu Asn Gly Ile Ala Thr Leu Asp Asp Glu Trp Arg
        355                 360                 365

Ile Glu Phe Ile Ile Gln His Leu Gln Tyr Val His Lys Ala Leu Asn
    370                 375                 380

Asp Gly Phe Asp Leu Arg Gly Tyr Phe Tyr Trp Ser Phe Met Asp Asn
385                 390                 395                 400

Phe Glu Trp Ala Glu Gly Phe Arg Pro Arg Phe Gly Leu Val Glu Val
                405                 410                 415
```

```
Asp Tyr Thr Thr Phe Lys Arg Arg Pro Arg Lys Ser Ala Tyr Ile Tyr
            420                 425                 430

Gly Glu Ile Ala Arg Glu Lys Lys Ile Lys Asp Glu Leu Leu Ala Lys
        435                 440                 445

Tyr Gly Leu Pro Glu Leu
    450


<210> SEQ ID NO 21
<211> LENGTH: 511
<212> TYPE: PRT
<213> ORGANISM: Thermococcus chitonophagus

<400> SEQUENCE: 21

Leu Leu Pro Glu Asn Phe Leu Trp Gly Val Ser Gln Ser Gly Phe Gln
 1               5                  10                  15

Phe Glu Met Gly Asp Arg Leu Arg Arg His Ile Asp Pro Asn Thr Asp
            20                  25                  30

Trp Trp Tyr Trp Val Arg Asp Glu Tyr Asn Ile Lys Lys Gly Leu Val
        35                  40                  45

Ser Gly Asp Leu Pro Glu Asp Gly Ile Asn Ser Tyr Glu Leu Tyr Glu
    50                  55                  60

Arg Asp Gln Glu Ile Ala Lys Asp Leu Gly Leu Asn Thr Tyr Arg Ile
65                  70                  75                  80

Gly Ile Glu Trp Ser Arg Val Phe Pro Trp Pro Thr Thr Phe Val Asp
                85                  90                  95

Val Glu Tyr Glu Ile Asp Glu Ser Tyr Gly Leu Val Lys Asp Val Lys
            100                 105                 110

Ile Ser Lys Asp Ala Leu Glu Lys Leu Asp Glu Ile Ala Asn Gln Arg
        115                 120                 125

Glu Ile Ile Tyr Tyr Arg Asn Leu Ile Asn Ser Leu Arg Lys Arg Gly
    130                 135                 140

Phe Lys Val Ile Leu Asn Leu Asn His Phe Thr Leu Pro Ile Trp Leu
145                 150                 155                 160

His Asp Pro Ile Glu Ser Arg Glu Lys Ala Leu Thr Asn Lys Arg Asn
                165                 170                 175

Gly Trp Val Ser Glu Arg Ser Val Ile Glu Phe Ala Lys Phe Ala Ala
            180                 185                 190

Tyr Leu Ala Tyr Lys Phe Gly Asp Ile Val Asp Met Trp Ser Thr Phe
        195                 200                 205

Asn Glu Pro Met Val Val Ala Glu Leu Gly Tyr Leu Ala Pro Tyr Ser
    210                 215                 220

Gly Phe Pro Pro Gly Val Met Asn Pro Glu Ala Ala Lys Leu Val Met
225                 230                 235                 240

Leu His Met Ile Asn Ala His Ala Leu Ala Tyr Arg Met Ile Lys Lys
                245                 250                 255

Phe Asp Arg Lys Lys Ala Asp Pro Glu Ser Lys Glu Pro Ala Glu Ile
            260                 265                 270

Gly Ile Ile Tyr Asn Asn Ile Gly Val Thr Tyr Pro Phe Asn Pro Lys
        275                 280                 285

Asp Ser Lys Asp Leu Gln Ala Ser Asp Asn Ala Asn Phe Phe His Ser
    290                 295                 300

Gly Leu Phe Leu Thr Ala Ile His Arg Gly Lys Leu Asn Ile Glu Phe
305                 310                 315                 320

Asp Gly Glu Thr Phe Val Tyr Leu Pro Tyr Leu Lys Gly Asn Asp Trp
                325                 330                 335
```

```
Leu Gly Val Asn Tyr Tyr Thr Arg Glu Val Val Lys Tyr Gln Asp Pro
            340                 345                 350

Met Phe Pro Ser Ile Pro Leu Ile Ser Phe Lys Gly Val Pro Asp Tyr
        355                 360                 365

Gly Tyr Gly Cys Arg Pro Gly Thr Thr Ser Lys Asp Gly Asn Pro Val
    370                 375                 380

Ser Asp Ile Gly Trp Glu Val Tyr Pro Lys Gly Met Tyr Asp Ser Ile
385                 390                 395                 400

Val Ala Ala Asn Glu Tyr Gly Val Pro Val Tyr Val Thr Glu Asn Gly
                405                 410                 415

Ile Ala Asp Ser Lys Asp Val Leu Arg Pro Tyr Tyr Ile Ala Ser His
            420                 425                 430

Ile Glu Ala Met Glu Glu Ala Tyr Glu Asn Gly Tyr Asp Val Arg Gly
        435                 440                 445

Tyr Leu His Trp Ala Leu Thr Asp Asn Tyr Glu Trp Ala Leu Gly Phe
    450                 455                 460

Arg Met Arg Phe Gly Leu Tyr Glu Val Asn Leu Ile Thr Lys Glu Arg
465                 470                 475                 480

Lys Pro Arg Lys Lys Ser Val Arg Val Phe Arg Glu Ile Val Ile Asn
                485                 490                 495

Asn Gly Leu Thr Ser Asn Ile Arg Lys Glu Ile Leu Glu Glu Gly
            500                 505                 510


<210> SEQ ID NO 22
<211> LENGTH: 510
<212> TYPE: PRT
<213> ORGANISM: Pyrococcus furiosus

<400> SEQUENCE: 22

Met Phe Pro Glu Lys Phe Leu Trp Gly Val Ala Gln Ser Gly Phe Gln
 1               5                  10                  15

Phe Glu Met Gly Asp Lys Leu Arg Arg Asn Ile Asp Thr Asn Thr Asp
            20                  25                  30

Trp Trp His Trp Val Arg Asp Lys Thr Asn Ile Glu Lys Gly Leu Val
        35                  40                  45

Ser Gly Asp Leu Pro Glu Glu Gly Ile Asn Asn Tyr Glu Leu Tyr Glu
    50                  55                  60

Lys Asp His Glu Ile Ala Arg Lys Leu Gly Leu Asn Ala Tyr Arg Ile
65                  70                  75                  80

Gly Ile Glu Trp Ser Arg Ile Phe Pro Trp Pro Thr Thr Phe Ile Asp
                85                  90                  95

Val Asp Tyr Ser Tyr Asn Glu Ser Tyr Asn Leu Ile Glu Asp Val Lys
            100                 105                 110

Ile Thr Lys Asp Thr Leu Glu Glu Leu Asp Glu Ile Ala Asn Lys Arg
        115                 120                 125

Glu Val Ala Tyr Tyr Arg Ser Val Ile Asn Ser Leu Arg Ser Lys Gly
    130                 135                 140

Phe Lys Val Ile Val Asn Leu Asn His Phe Thr Leu Pro Tyr Trp Leu
145                 150                 155                 160

His Asp Pro Ile Glu Ala Arg Glu Arg Ala Leu Thr Asn Lys Arg Asn
                165                 170                 175

Gly Trp Val Asn Pro Arg Thr Val Ile Glu Phe Ala Lys Tyr Ala Ala
            180                 185                 190

Tyr Ile Ala Tyr Lys Phe Gly Asp Ile Val Asp Met Trp Ser Thr Phe
```

```
        195                 200                 205

Asn Glu Pro Met Val Val Val Glu Leu Gly Tyr Leu Ala Pro Tyr Ser
    210                 215                 220

Gly Phe Pro Pro Gly Val Leu Asn Pro Glu Ala Ala Lys Leu Ala Ile
225                 230                 235                 240

Leu His Met Ile Asn Ala His Ala Leu Ala Tyr Arg Gln Ile Lys Lys
                245                 250                 255

Phe Asp Thr Glu Lys Ala Asp Lys Asp Ser Lys Glu Pro Ala Glu Val
            260                 265                 270

Gly Ile Ile Tyr Asn Asn Ile Gly Val Ala Tyr Pro Lys Asp Pro Asn
        275                 280                 285

Asp Ser Lys Asp Val Lys Ala Ala Glu Asn Asp Asn Phe Phe His Ser
    290                 295                 300

Gly Leu Phe Phe Glu Ala Ile His Lys Gly Lys Leu Asn Ile Glu Phe
305                 310                 315                 320

Asp Gly Glu Thr Phe Ile Asp Ala Pro Tyr Leu Lys Gly Asn Asp Trp
                325                 330                 335

Ile Gly Val Asn Tyr Tyr Thr Arg Glu Val Val Thr Tyr Gln Glu Pro
            340                 345                 350

Met Phe Pro Ser Ile Pro Leu Ile Thr Phe Lys Gly Val Gln Gly Tyr
        355                 360                 365

Gly Tyr Ala Cys Arg Pro Gly Thr Leu Ser Lys Asp Asp Arg Pro Val
    370                 375                 380

Ser Asp Ile Gly Trp Glu Leu Tyr Pro Glu Gly Met Tyr Asp Ser Ile
385                 390                 395                 400

Val Glu Ala His Lys Tyr Gly Val Pro Val Tyr Val Thr Glu Asn Gly
                405                 410                 415

Ile Ala Asp Ser Lys Asp Ile Leu Arg Pro Tyr Tyr Ile Ala Ser His
            420                 425                 430

Ile Lys Met Ile Glu Lys Ala Phe Glu Asp Gly Tyr Glu Val Lys Gly
        435                 440                 445

Tyr Phe His Trp Ala Leu Thr Asp Asn Phe Glu Trp Ala Leu Gly Phe
    450                 455                 460

Arg Met Arg Phe Gly Leu Tyr Glu Val Asn Leu Ile Thr Lys Glu Arg
465                 470                 475                 480

Ile Pro Arg Glu Lys Ser Val Ser Ile Phe Arg Glu Ile Val Ala Asn
                485                 490                 495

Asn Gly Val Thr Lys Lys Ile Glu Glu Glu Leu Leu Arg Gly
            500                 505                 510


<210> SEQ ID NO 23
<211> LENGTH: 537
<212> TYPE: PRT
<213> ORGANISM: Bankia gouldi

<400> SEQUENCE: 23

Met Arg Ile Arg Leu Ala Thr Leu Ala Leu Cys Ala Ala Leu Ser Pro
 1               5                  10                  15

Val Thr Phe Ala Asp Asn Val Thr Val Gln Ile Asp Ala Asp Gly Gly
            20                  25                  30

Lys Lys Leu Ile Ser Arg Ala Leu Tyr Gly Met Asn Asn Ser Asn Ala
        35                  40                  45

Glu Ser Leu Thr Asp Thr Asp Trp Gln Arg Phe Arg Asp Ala Gly Val
    50                  55                  60
```

-continued

```
Arg Met Leu Arg Glu Asn Gly Gly Asn Asn Ser Thr Lys Tyr Asn Trp
65                  70                  75                  80

Gln Leu His Leu Ser Ser His Pro Asp Trp Tyr Asn Asn Val Tyr Ala
                85                  90                  95

Gly Asn Asn Asn Trp Asp Asn Arg Val Ala Leu Ile Gln Glu Asn Leu
            100                 105                 110

Pro Gly Ala Asp Thr Met Trp Ala Phe Gln Leu Ile Gly Lys Val Ala
        115                 120                 125

Ala Thr Ser Ala Tyr Asn Phe Asn Asp Trp Glu Phe Asn Gln Ser Gln
    130                 135                 140

Trp Trp Thr Gly Val Ala Gln Asn Leu Ala Gly Gly Gly Glu Pro Asn
145                 150                 155                 160

Leu Asp Gly Gly Gly Glu Ala Leu Val Glu Gly Asp Pro Asn Leu Tyr
                165                 170                 175

Leu Met Asp Trp Ser Pro Ala Asp Thr Val Gly Ile Leu Asp His Trp
            180                 185                 190

Phe Gly Val Asn Gly Leu Gly Val Arg Arg Gly Lys Ala Lys Tyr Trp
        195                 200                 205

Ser Met Asp Asn Glu Pro Gly Ile Trp Val Gly Thr His Asp Asp Val
    210                 215                 220

Val Lys Glu Gln Thr Pro Val Glu Asp Phe Leu His Thr Tyr Phe Glu
225                 230                 235                 240

Thr Ala Lys Lys Ala Arg Ala Lys Phe Pro Gly Ile Lys Ile Thr Gly
                245                 250                 255

Pro Val Pro Ala Asn Glu Trp Gln Trp Tyr Ala Trp Gly Gly Phe Ser
            260                 265                 270

Val Pro Gln Glu Gln Gly Phe Met Ser Trp Met Glu Tyr Phe Ile Lys
        275                 280                 285

Arg Val Ser Glu Glu Gln Arg Ala Ser Gly Val Arg Leu Leu Asp Val
    290                 295                 300

Leu Asp Leu His Tyr Tyr Pro Gly Ala Tyr Asn Ala Glu Asp Ile Val
305                 310                 315                 320

Gln Leu His Arg Thr Phe Phe Asp Arg Asp Phe Val Ser Leu Asp Ala
                325                 330                 335

Asn Gly Val Lys Met Val Glu Gly Gly Trp Asp Asp Ser Ile Asn Lys
            340                 345                 350

Glu Tyr Ile Phe Gly Arg Val Asn Asp Trp Leu Glu Glu Tyr Met Gly
        355                 360                 365

Pro Asp His Gly Val Thr Leu Gly Leu Thr Glu Met Cys Val Arg Asn
    370                 375                 380

Val Asn Pro Met Thr Thr Ala Ile Trp Tyr Ala Ser Met Leu Gly Thr
385                 390                 395                 400

Phe Ala Asp Asn Gly Val Glu Ile Phe Thr Pro Trp Cys Trp Asn Thr
                405                 410                 415

Gly Met Trp Glu Thr Leu His Leu Phe Ser Arg Tyr Asn Lys Pro Tyr
            420                 425                 430

Arg Val Ala Ser Ser Ser Ser Leu Glu Glu Phe Val Ser Ala Tyr Ser
        435                 440                 445

Ser Ile Asn Glu Ala Glu Asp Ala Met Thr Val Leu Leu Val Asn Arg
    450                 455                 460

Ser Thr Ser Glu Thr His Thr Ala Thr Val Ala Ile Asp Asp Phe Pro
465                 470                 475                 480

Leu Asp Gly Pro Tyr Arg Thr Leu Arg Leu His Asn Leu Pro Gly Glu
```

```
                485                 490                 495

Glu Thr Phe Val Ser His Arg Asp Asn Ala Leu Glu Lys Gly Thr Val
            500                 505                 510

Arg Ala Ser Asp Asn Thr Val Thr Leu Glu Leu Pro Pro Leu Ser Val
        515                 520                 525

Thr Ala Ile Leu Leu Lys Ala Arg Pro
    530                 535


<210> SEQ ID NO 24
<211> LENGTH: 555
<212> TYPE: PRT
<213> ORGANISM: Thermotoga maritima

<400> SEQUENCE: 24

Val Ile Cys Val Glu Ile Phe Gly Lys Thr Phe Arg Glu Gly Arg Phe
 1               5                  10                  15

Val Leu Lys Glu Lys Asn Phe Thr Val Glu Phe Ala Val Glu Lys Ile
            20                  25                  30

His Leu Gly Trp Lys Ile Ser Gly Arg Val Lys Gly Ser Pro Gly Arg
        35                  40                  45

Leu Glu Val Leu Arg Thr Lys Ala Pro Glu Lys Val Leu Val Asn Asn
    50                  55                  60

Trp Gln Ser Trp Gly Pro Cys Arg Val Val Asp Ala Phe Ser Phe Lys
65                  70                  75                  80

Pro Pro Glu Ile Asp Pro Asn Trp Arg Tyr Thr Ala Ser Val Val Pro
                85                  90                  95

Asp Val Leu Glu Arg Asn Leu Gln Ser Asp Tyr Phe Val Ala Glu Glu
            100                 105                 110

Gly Lys Val Tyr Gly Phe Leu Ser Ser Lys Ile Ala His Pro Phe Phe
        115                 120                 125

Ala Val Glu Asp Gly Glu Leu Val Ala Tyr Leu Glu Tyr Phe Asp Val
    130                 135                 140

Glu Phe Asp Asp Phe Val Pro Leu Glu Pro Leu Val Val Leu Glu Asp
145                 150                 155                 160

Pro Asn Thr Pro Leu Leu Leu Glu Lys Tyr Ala Glu Leu Val Gly Met
                165                 170                 175

Glu Asn Asn Ala Arg Val Pro Lys His Thr Pro Thr Gly Trp Cys Ser
            180                 185                 190

Trp Tyr His Tyr Phe Leu Asp Leu Thr Trp Glu Glu Thr Leu Lys Asn
        195                 200                 205

Leu Lys Leu Ala Lys Asn Phe Pro Phe Glu Val Phe Gln Ile Asp Asp
    210                 215                 220

Ala Tyr Glu Lys Asp Ile Gly Asp Trp Leu Val Thr Arg Gly Asp Phe
225                 230                 235                 240

Pro Ser Val Glu Glu Met Ala Lys Val Ile Ala Glu Asn Gly Phe Ile
                245                 250                 255

Pro Gly Ile Trp Thr Ala Pro Phe Ser Val Ser Glu Thr Ser Asp Val
            260                 265                 270

Phe Asn Glu His Pro Asp Trp Val Val Lys Glu Asn Gly Glu Pro Lys
        275                 280                 285

Met Ala Tyr Arg Asn Trp Asn Lys Lys Ile Tyr Ala Leu Asp Leu Ser
    290                 295                 300

Lys Asp Glu Val Leu Asn Trp Leu Phe Asp Leu Phe Ser Ser Leu Arg
305                 310                 315                 320
```

-continued

```
Lys Met Gly Tyr Arg Tyr Phe Lys Ile Asp Phe Leu Phe Ala Gly Ala
                325                 330                 335

Val Pro Gly Glu Arg Lys Lys Asn Ile Thr Pro Ile Gln Ala Phe Arg
            340                 345                 350

Lys Gly Ile Glu Thr Ile Arg Lys Ala Val Gly Glu Asp Ser Phe Ile
        355                 360                 365

Leu Gly Cys Gly Ser Pro Leu Leu Pro Ala Val Gly Cys Val Asp Gly
    370                 375                 380

Met Arg Ile Gly Pro Asp Thr Ala Pro Phe Trp Gly Glu His Ile Glu
385                 390                 395                 400

Asp Asn Gly Ala Pro Ala Ala Arg Trp Ala Leu Arg Asn Ala Ile Thr
                405                 410                 415

Arg Tyr Phe Met His Asp Arg Phe Trp Leu Asn Asp Pro Asp Cys Leu
            420                 425                 430

Ile Leu Arg Glu Glu Lys Thr Asp Leu Thr Gln Lys Glu Lys Glu Leu
        435                 440                 445

Tyr Ser Tyr Thr Cys Gly Val Leu Asp Asn Met Ile Ile Glu Ser Asp
    450                 455                 460

Asp Leu Ser Leu Val Arg Asp His Gly Lys Lys Val Leu Lys Glu Thr
465                 470                 475                 480

Leu Glu Leu Leu Gly Gly Arg Pro Arg Val Gln Asn Ile Met Ser Glu
                485                 490                 495

Asp Leu Arg Tyr Glu Ile Val Ser Ser Gly Thr Leu Ser Gly Asn Val
            500                 505                 510

Lys Ile Val Val Asp Leu Asn Ser Arg Glu Tyr His Leu Glu Lys Glu
        515                 520                 525

Gly Lys Ser Ser Leu Lys Lys Arg Val Val Lys Arg Glu Asp Gly Arg
    530                 535                 540

Asn Phe Tyr Phe Tyr Glu Glu Gly Glu Arg Glu
545                 550                 555


<210> SEQ ID NO 25
<211> LENGTH: 680
<212> TYPE: PRT
<213> ORGANISM: Thermotoga maritima

<400> SEQUENCE: 25

Met Gly Ile Gly Gly Asp Asp Ser Trp Ser Pro Ser Val Ser Ala Glu
 1               5                  10                  15

Phe Leu Leu Leu Ile Val Glu Leu Ser Phe Val Leu Phe Ala Ser Asp
            20                  25                  30

Glu Phe Val Lys Val Glu Asn Gly Lys Phe Ala Leu Asn Gly Lys Glu
        35                  40                  45

Phe Arg Phe Ile Gly Ser Asn Asn Tyr Tyr Met His Tyr Lys Ser Asn
    50                  55                  60

Gly Met Ile Asp Ser Val Leu Glu Ser Ala Arg Asp Met Gly Ile Lys
65                  70                  75                  80

Val Leu Arg Ile Trp Gly Phe Leu Asp Gly Glu Ser Tyr Cys Arg Asp
                85                  90                  95

Lys Asn Thr Tyr Met His Pro Glu Pro Gly Val Phe Gly Val Pro Glu
            100                 105                 110

Gly Ile Ser Asn Ala Gln Ser Gly Phe Glu Arg Leu Asp Tyr Thr Val
        115                 120                 125

Ala Lys Ala Lys Glu Leu Gly Ile Lys Leu Val Ile Val Leu Val Asn
    130                 135                 140
```

-continued

```
Asn Trp Asp Asp Phe Gly Gly Met Asn Gln Tyr Val Arg Trp Phe Gly
145                 150                 155                 160

Gly Thr His His Asp Asp Phe Tyr Arg Asp Glu Lys Ile Lys Glu Glu
                165                 170                 175

Tyr Lys Lys Tyr Val Ser Phe Leu Val Asn His Val Asn Thr Tyr Thr
            180                 185                 190

Gly Val Pro Tyr Arg Glu Glu Pro Thr Ile Met Ala Trp Glu Leu Ala
        195                 200                 205

Asn Glu Pro Arg Cys Glu Thr Asp Lys Ser Gly Asn Thr Leu Val Glu
    210                 215                 220

Trp Val Lys Glu Met Ser Ser Tyr Ile Lys Ser Leu Asp Pro Asn His
225                 230                 235                 240

Leu Val Ala Val Gly Asp Glu Gly Phe Phe Ser Asn Tyr Glu Gly Phe
                245                 250                 255

Lys Pro Tyr Gly Gly Glu Ala Glu Trp Ala Tyr Asn Gly Trp Ser Gly
            260                 265                 270

Val Asp Trp Lys Lys Leu Leu Ser Ile Glu Thr Val Asp Phe Gly Thr
        275                 280                 285

Phe His Leu Tyr Pro Ser His Trp Gly Val Ser Pro Glu Asn Tyr Ala
    290                 295                 300

Gln Trp Gly Ala Lys Trp Ile Glu Asp His Ile Lys Ile Ala Lys Glu
305                 310                 315                 320

Ile Gly Lys Pro Val Val Leu Glu Glu Tyr Gly Ile Pro Lys Ser Ala
                325                 330                 335

Pro Val Asn Arg Thr Ala Ile Tyr Arg Leu Trp Asn Asp Leu Val Tyr
            340                 345                 350

Asp Leu Gly Gly Asp Gly Ala Met Phe Trp Met Leu Ala Gly Ile Gly
        355                 360                 365

Glu Gly Ser Asp Arg Asp Glu Arg Gly Tyr Tyr Pro Asp Tyr Asp Gly
    370                 375                 380

Phe Arg Ile Val Asn Asp Asp Ser Pro Glu Ala Glu Leu Ile Arg Glu
385                 390                 395                 400

Tyr Ala Lys Leu Phe Asn Thr Gly Glu Asp Ile Arg Glu Asp Thr Cys
                405                 410                 415

Ser Phe Ile Leu Pro Lys Asp Gly Met Glu Ile Lys Lys Thr Val Glu
            420                 425                 430

Val Arg Ala Gly Val Phe Asp Tyr Ser Asn Thr Phe Glu Lys Leu Ser
        435                 440                 445

Val Lys Val Glu Asp Leu Val Phe Glu Asn Glu Ile Glu His Leu Gly
    450                 455                 460

Tyr Gly Ile Tyr Gly Phe Asp Leu Asp Thr Thr Arg Ile Pro Asp Gly
465                 470                 475                 480

Glu His Glu Met Phe Leu Glu Gly His Phe Gln Gly Lys Thr Val Lys
                485                 490                 495

Asp Ser Ile Lys Ala Lys Val Val Asn Glu Ala Arg Tyr Val Leu Ala
            500                 505                 510

Glu Glu Val Asp Phe Ser Ser Pro Glu Glu Val Lys Asn Trp Trp Asn
        515                 520                 525

Ser Gly Thr Trp Gln Ala Glu Phe Gly Ser Pro Asp Ile Glu Trp Asn
    530                 535                 540

Gly Glu Val Gly Asn Gly Ala Leu Gln Leu Asn Val Lys Leu Pro Gly
545                 550                 555                 560
```

```
Lys Ser Asp Trp Glu Glu Val Arg Val Ala Arg Lys Phe Glu Arg Leu
                565                 570                 575

Ser Glu Cys Glu Ile Leu Glu Tyr Asp Ile Tyr Ile Pro Asn Val Glu
            580                 585                 590

Gly Leu Lys Gly Arg Leu Arg Pro Tyr Ala Val Leu Asn Pro Gly Trp
        595                 600                 605

Val Lys Ile Gly Leu Asp Met Asn Asn Ala Asn Val Glu Ser Ala Glu
    610                 615                 620

Ile Ile Thr Phe Gly Gly Lys Glu Tyr Arg Arg Phe His Val Arg Ile
625                 630                 635                 640

Glu Phe Asp Arg Thr Ala Gly Val Lys Glu Leu His Ile Gly Val Val
                645                 650                 655

Gly Asp His Leu Arg Tyr Asp Gly Pro Ile Phe Ile Asp Asn Val Arg
            660                 665                 670

Leu Tyr Lys Arg Thr Gly Gly Met
        675                 680


<210> SEQ ID NO 26
<211> LENGTH: 512
<212> TYPE: PRT
<213> ORGANISM: Thermococcus chitonophagus

<400> SEQUENCE: 26

Met Leu Pro Glu Glu Phe Leu Trp Gly Val Gly Gln Ser Gly Phe Gln
 1               5                  10                  15

Phe Glu Met Gly Asp Lys Leu Arg Arg His Ile Asp Pro Asn Thr Asp
            20                  25                  30

Trp Trp Lys Trp Val Arg Asp Pro Phe Asn Ile Lys Lys Glu Leu Val
        35                  40                  45

Ser Gly Asp Leu Pro Glu Asp Gly Ile Asn Asn Tyr Glu Leu Phe Glu
    50                  55                  60

Asn Asp His Lys Leu Ala Lys Gly Leu Gly Leu Asn Ala Tyr Arg Ile
65                  70                  75                  80

Gly Ile Glu Trp Ser Arg Ile Phe Pro Trp Pro Thr Trp Thr Val Asp
                85                  90                  95

Thr Glu Val Glu Phe Asp Thr Tyr Gly Leu Val Lys Asp Val Lys Ile
            100                 105                 110

Asp Lys Ser Thr Leu Ala Glu Leu Asp Arg Leu Ala Asn Lys Glu Glu
        115                 120                 125

Val Met Tyr Tyr Arg Arg Val Ile Gln His Leu Arg Glu Leu Gly Phe
    130                 135                 140

Lys Val Phe Val Asn Leu Asn His Phe Thr Leu Pro Ile Trp Leu His
145                 150                 155                 160

Asp Pro Ile Val Ala Arg Glu Lys Ala Leu Thr Asn Asp Arg Ile Gly
                165                 170                 175

Trp Val Ser Gln Arg Thr Val Val Glu Phe Ala Lys Tyr Ala Ala Tyr
            180                 185                 190

Ile Ala His Ala Leu Gly Asp Leu Val Asp Thr Trp Ser Thr Phe Asn
        195                 200                 205

Glu Pro Met Val Val Val Glu Leu Gly Tyr Leu Ala Pro Tyr Ser Gly
    210                 215                 220

Phe Pro Pro Gly Val Met Asn Pro Glu Ala Ala Lys Leu Ala Ile Leu
225                 230                 235                 240

Asn Met Ile Asn Ala His Ala Leu Ala Tyr Lys Met Ile Lys Arg Phe
                245                 250                 255
```

```
Asp Thr Lys Lys Ala Asp Glu Asp Ser Lys Ser Pro Ala Asp Val Gly
            260                 265                 270

Ile Ile Tyr Asn Asn Ile Gly Val Ala Tyr Pro Lys Asp Pro Asn Asp
        275                 280                 285

Pro Lys Asp Val Lys Ala Ala Glu Asn Asp Asn Tyr Phe His Ser Gly
    290                 295                 300

Leu Phe Phe Asp Ala Ile His Lys Gly Lys Leu Asn Ile Glu Phe Asp
305                 310                 315                 320

Gly Glu Asn Phe Val Lys Val Arg His Leu Lys Gly Asn Asp Trp Ile
                325                 330                 335

Gly Leu Asn Tyr Tyr Thr Arg Glu Val Val Arg Tyr Ser Glu Pro Lys
            340                 345                 350

Phe Pro Ser Ile Pro Leu Ile Ser Phe Lys Gly Val Pro Asn Tyr Gly
        355                 360                 365

Tyr Ser Cys Arg Pro Gly Thr Thr Ser Ala Asp Gly Met Pro Val Ser
    370                 375                 380

Asp Ile Gly Trp Glu Val Tyr Pro Gln Gly Ile Tyr Asp Ser Ile Val
385                 390                 395                 400

Glu Ala Thr Lys Tyr Ser Val Pro Val Tyr Val Thr Glu Asn Gly Val
                405                 410                 415

Ala Asp Ser Ala Asp Thr Leu Arg Pro Tyr Tyr Ile Val Ser His Val
            420                 425                 430

Ser Lys Ile Glu Glu Ala Ile Glu Asn Gly Tyr Pro Val Lys Gly Tyr
        435                 440                 445

Met Tyr Trp Ala Leu Thr Asp Asn Tyr Glu Trp Ala Leu Gly Phe Ser
    450                 455                 460

Met Arg Phe Gly Leu Tyr Lys Val Asp Leu Ile Ser Lys Glu Arg Ile
465                 470                 475                 480

Pro Arg Glu Arg Ser Val Glu Ile Tyr Arg Arg Ile Val Gln Ser Asn
                485                 490                 495

Gly Val Pro Lys Asp Ile Lys Glu Glu Phe Leu Lys Gly Glu Glu Lys
            500                 505                 510


<210> SEQ ID NO 27
<211> LENGTH: 360
<212> TYPE: PRT
<213> ORGANISM: Thermotoga sp.

<400> SEQUENCE: 27

Met Val Glu Arg His Phe Arg Tyr Val Leu Ile Cys Thr Leu Phe Leu
 1               5                  10                  15

Val Met Leu Leu Ile Ser Ser Thr Gln Cys Gly Lys Asn Glu Pro Asn
            20                  25                  30

Lys Arg Val Asn Ser Met Glu Gln Ser Val Ala Glu Ser Asp Ser Asn
        35                  40                  45

Ser Ala Phe Glu Tyr Asn Lys Met Val Gly Lys Gly Val Asn Ile Gly
    50                  55                  60

Asn Ala Leu Glu Ala Pro Phe Glu Gly Ala Trp Gly Val Arg Ile Glu
65                  70                  75                  80

Asp Glu Tyr Phe Glu Ile Ile Lys Lys Arg Gly Phe Asp Ser Val Arg
                85                  90                  95

Ile Pro Ile Arg Trp Ser Ala His Ile Ser Glu Lys Pro Pro Tyr Asp
            100                 105                 110

Ile Asp Arg Asn Phe Leu Glu Arg Val Asn His Val Val Asp Arg Ala
```

```
        115                 120                 125

Leu Glu Asn Asn Leu Thr Val Ile Ile Asn Thr His His Phe Glu Glu
    130                 135                 140

Leu Tyr Gln Glu Pro Asp Lys Tyr Gly Asp Val Leu Val Glu Ile Trp
145                 150                 155                 160

Arg Gln Ile Ala Lys Phe Phe Lys Asp Tyr Pro Glu Asn Leu Phe Phe
                165                 170                 175

Glu Ile Tyr Asn Glu Pro Ala Gln Asn Leu Thr Ala Glu Lys Trp Asn
            180                 185                 190

Ala Leu Tyr Pro Lys Val Leu Lys Val Ile Arg Glu Ser Asn Pro Thr
        195                 200                 205

Arg Ile Val Ile Ile Asp Ala Pro Asn Trp Ala His Tyr Ser Ala Val
    210                 215                 220

Arg Ser Leu Lys Leu Val Asn Asp Lys Arg Ile Ile Val Ser Phe His
225                 230                 235                 240

Tyr Tyr Glu Pro Phe Lys Phe Thr His Gln Gly Ala Glu Trp Val Asn
                245                 250                 255

Pro Ile Pro Pro Val Arg Val Lys Trp Asn Gly Glu Glu Trp Glu Ile
            260                 265                 270

Asn Gln Ile Arg Ser His Phe Lys Tyr Val Ser Asp Trp Ala Lys Gln
        275                 280                 285

Asn Asn Val Pro Ile Phe Leu Gly Glu Phe Gly Ala Tyr Ser Lys Ala
    290                 295                 300

Asp Met Asp Ser Arg Val Lys Trp Thr Glu Ser Val Arg Lys Met Ala
305                 310                 315                 320

Glu Glu Phe Gly Phe Ser Tyr Ala Tyr Trp Glu Phe Cys Ala Gly Phe
                325                 330                 335

Gly Ile Tyr Asp Arg Trp Ser Gln Asn Trp Ile Glu Pro Leu Ala Thr
            340                 345                 350

Ala Val Val Gly Thr Gly Lys Glu
        355                 360


<210> SEQ ID NO 28
<211> LENGTH: 772
<212> TYPE: PRT
<213> ORGANISM: Thermotoga maritima

<400> SEQUENCE: 28

Met Asp Leu Thr Lys Val Gly Ile Ile Val Arg Leu Asn Glu Trp Gln
1               5                   10                  15

Ala Lys Asp Val Ala Lys Asp Arg Phe Ile Glu Ile Lys Asp Gly Lys
            20                  25                  30

Ala Glu Val Trp Ile Leu Gln Gly Val Glu Glu Ile Phe Tyr Glu Lys
        35                  40                  45

Pro Asp Thr Ser Pro Arg Ile Phe Phe Ala Gln Ala Arg Ser Asn Lys
    50                  55                  60

Val Ile Glu Ala Phe Leu Thr Asn Pro Val Asp Thr Lys Lys Lys Glu
65                  70                  75                  80

Leu Phe Lys Val Thr Val Asp Gly Lys Glu Ile Pro Val Ser Arg Val
                85                  90                  95

Glu Lys Ala Asp Pro Thr Asp Ile Asp Val Thr Asn Tyr Val Arg Ile
            100                 105                 110

Val Leu Ser Glu Ser Leu Lys Glu Glu Asp Leu Arg Lys Asp Val Glu
        115                 120                 125
```

-continued

```
Leu Ile Ile Glu Gly Tyr Lys Pro Ala Arg Val Ile Met Met Glu Ile
    130                 135                 140

Leu Asp Asp Tyr Tyr Tyr Asp Gly Glu Leu Gly Ala Val Tyr Ser Pro
145                 150                 155                 160

Glu Lys Thr Ile Phe Arg Val Trp Ser Pro Val Ser Lys Trp Val Lys
                165                 170                 175

Val Leu Leu Phe Lys Asn Gly Glu Asp Thr Glu Pro Tyr Gln Val Val
            180                 185                 190

Asn Met Glu Tyr Lys Gly Asn Gly Val Trp Glu Ala Val Val Glu Gly
        195                 200                 205

Asp Leu Asp Gly Val Phe Tyr Leu Tyr Gln Leu Glu Asn Tyr Gly Lys
    210                 215                 220

Ile Arg Thr Thr Val Asp Pro Tyr Ser Lys Ala Val Tyr Ala Asn Ser
225                 230                 235                 240

Lys Lys Ser Ala Val Val Asn Leu Ala Arg Thr Asn Pro Glu Gly Trp
                245                 250                 255

Glu Asn Asp Arg Gly Pro Lys Ile Glu Gly Tyr Glu Asp Ala Ile Ile
            260                 265                 270

Tyr Glu Ile His Ile Ala Asp Ile Thr Gly Leu Glu Asn Ser Gly Val
        275                 280                 285

Lys Asn Lys Gly Leu Tyr Leu Gly Leu Thr Glu Glu Asn Thr Lys Gly
    290                 295                 300

Pro Gly Gly Val Thr Thr Gly Leu Ser His Leu Val Glu Leu Gly Val
305                 310                 315                 320

Thr His Val His Ile Leu Pro Phe Phe Asp Phe Tyr Thr Gly Asp Glu
                325                 330                 335

Leu Asp Lys Asp Phe Glu Lys Tyr Tyr Asn Trp Gly Tyr Asp Pro Tyr
            340                 345                 350

Leu Phe Met Val Pro Glu Gly Arg Tyr Ser Thr Asp Pro Lys Asn Pro
        355                 360                 365

His Thr Arg Ile Arg Glu Val Lys Glu Met Val Lys Ala Leu His Lys
    370                 375                 380

His Gly Ile Gly Val Ile Met Asp Met Val Phe Pro His Thr Tyr Gly
385                 390                 395                 400

Ile Gly Glu Leu Ser Ala Phe Asp Gln Thr Val Pro Tyr Tyr Phe Tyr
                405                 410                 415

Arg Ile Asp Lys Thr Gly Ala Tyr Leu Asn Glu Ser Gly Cys Gly Asn
            420                 425                 430

Val Ile Ala Ser Glu Arg Pro Met Met Arg Lys Phe Ile Val Asp Thr
        435                 440                 445

Val Thr Tyr Trp Val Lys Glu Tyr His Ile Asp Gly Phe Arg Phe Asp
    450                 455                 460

Gln Met Gly Leu Ile Asp Lys Lys Thr Met Leu Glu Val Glu Arg Ala
465                 470                 475                 480

Leu His Lys Ile Asp Pro Thr Ile Ile Leu Tyr Gly Glu Pro Trp Gly
                485                 490                 495

Gly Trp Gly Ala Pro Ile Arg Phe Gly Lys Ser Asp Val Ala Gly Thr
            500                 505                 510

His Val Ala Ala Phe Asn Asp Glu Phe Arg Asp Ala Ile Arg Gly Ser
        515                 520                 525

Val Phe Asn Pro Ser Val Lys Gly Phe Val Met Gly Gly Tyr Gly Lys
    530                 535                 540

Glu Thr Lys Ile Lys Arg Gly Val Val Gly Ser Ile Asn Tyr Asp Gly
```

```
545                 550                 555                 560

Lys Leu Ile Lys Ser Leu Ala Leu Asp Pro Glu Glu Thr Ile Asn Tyr
                565                 570                 575

Ala Ala Cys His Asp Asn His Thr Leu Trp Asp Lys Asn Tyr Leu Ala
            580                 585                 590

Ala Lys Ala Asp Lys Lys Lys Glu Trp Thr Glu Glu Glu Leu Lys Asn
        595                 600                 605

Ala Gln Lys Leu Ala Gly Ala Ile Leu Leu Thr Ser Gln Gly Val Pro
    610                 615                 620

Phe Leu His Gly Gly Gln Asp Phe Cys Arg Thr Lys Asn Phe Asn Asp
625                 630                 635                 640

Asn Ser Tyr Asn Ala Pro Ile Ser Ile Asn Gly Phe Asp Tyr Glu Arg
                645                 650                 655

Lys Leu Gln Phe Ile Asp Val Phe Asn Tyr His Lys Gly Leu Ile Lys
            660                 665                 670

Leu Arg Lys Glu His Pro Ala Phe Arg Leu Lys Asn Ala Glu Glu Ile
        675                 680                 685

Lys Lys His Leu Glu Phe Leu Pro Gly Gly Arg Arg Ile Val Ala Phe
    690                 695                 700

Met Leu Lys Asp His Ala Gly Gly Asp Pro Trp Lys Asp Ile Val Val
705                 710                 715                 720

Ile Tyr Asn Gly Asn Leu Glu Lys Thr Thr Tyr Lys Leu Pro Glu Gly
                725                 730                 735

Lys Trp Asn Val Val Val Asn Ser Gln Lys Ala Gly Thr Glu Val Ile
            740                 745                 750

Glu Thr Val Glu Gly Thr Ile Glu Leu Asp Pro Leu Ser Ala Tyr Val
        755                 760                 765

Leu Tyr Arg Glu
    770


<210> SEQ ID NO 29
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 29

ccgagaattc attaaagagg agaaattaac tatggtgaat gctatgattg tc           52


<210> SEQ ID NO 30
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 30

atacccgaag gcctcgatac ttctagaagg c                                  31


<210> SEQ ID NO 31
<211> LENGTH: 54
<212> TYPE: DNA
<213> ORGANISM: Artificial sequence
<220> FEATURE:
<223> OTHER INFORMATION: synthetically generated oligonucleotide

<400> SEQUENCE: 31

ccgagaattc attaaagagg agaaattaac tatgataaga aggtccgatt ttcc         54
```

<210> SEQ ID NO 32
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 32
ttccttaaag attttagaat ttctagaagg c 31

<210> SEQ ID NO 33
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 33
ccgagaattc attaaagagg agaaattaac tatgctacca gaaggctttc tc 52

<210> SEQ ID NO 34
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 34
ctcttcaagc ctgaacccac tccatggagg c 31

<210> SEQ ID NO 35
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 35
ccgagaattc attaaagagg agaaattaac tatgataagg tttcctgatt at 52

<210> SEQ ID NO 36
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 36
cctaatttct tggagcttat ttctagaagg c 31

<210> SEQ ID NO 37
<211> LENGTH: 57
<212> TYPE: DNA
<213> ORGANISM: Artificial sequence
<220> FEATURE:
<223> OTHER INFORMATION: synthetically generated oligonucleotide

<400> SEQUENCE: 37
ccgagaattc attcattaaa gaggagaaat taactatgct tccaggagaa ctttctc 57

<210> SEQ ID NO 38
<211> LENGTH: 31
<212> TYPE: DNA
<213> ORGANISM: Artificial sequence
<220> FEATURE:

-continued

<223> OTHER INFORMATION: synthetically generated oligonucleotide

<400> SEQUENCE: 38
ctctagaatc tcctccccat ccctaggagg c 31

<210> SEQ ID NO 39
<211> LENGTH: 40
<212> TYPE: DNA
<213> ORGANISM: Artificial sequence
<220> FEATURE:
<223> OTHER INFORMATION: synthetically generated oligonucleotide

<400> SEQUENCE: 39
ataatctaga gcatgcaatt ccccaaagac ttcatgatag 40

<210> SEQ ID NO 40
<211> LENGTH: 32
<212> TYPE: DNA
<213> ORGANISM: Artificial sequence
<220> FEATURE:
<223> OTHER INFORMATION: synthetically generated oligonucleotide

<400> SEQUENCE: 40
tcgtagaatg tgactaggtc attcgaaaat aa 32

<210> SEQ ID NO 41
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 41
ccgacaattg attaaagagg agaaattaac tatggaaagg atcgatgaaa tt 52

<210> SEQ ID NO 42
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 42
ctcttctcta agtttggtac tccatggagg c 31

<210> SEQ ID NO 43
<211> LENGTH: 52
<212> TYPE: DNA
<213> ORGANISM: Artificial sequence
<220> FEATURE:
<223> OTHER INFORMATION: synthetically generated oligonucleotide

<400> SEQUENCE: 43
ccgacaattg attaaagagg agaaattaac tatgttccct gaaaagttcc tt 52

<210> SEQ ID NO 44
<211> LENGTH: 31
<212> TYPE: DNA
<213> ORGANISM: Artificial sequence
<220> FEATURE:
<223> OTHER INFORMATION: synthetically generated oligonucleotide

<400> SEQUENCE: 44
ctccttaacg actcccctac tccatggagg c 31

<210> SEQ ID NO 45
<211> LENGTH: 27
<212> TYPE: DNA
<213> ORGANISM: Artificial sequence
<220> FEATURE:
<223> OTHER INFORMATION: synthetically generated oligonucleotide

<400> SEQUENCE: 45
aataaggatc cgtttagcga cgctcgc 27

<210> SEQ ID NO 46
<211> LENGTH: 35
<212> TYPE: DNA
<213> ORGANISM: Artificial sequence
<220> FEATURE:
<223> OTHER INFORMATION: synthetically generated oligonucleotide

<400> SEQUENCE: 46
cggataatgg cgacatgttg ggccttcgaa aataa 35

<210> SEQ ID NO 47
<211> LENGTH: 60
<212> TYPE: DNA
<213> ORGANISM: Artificial sequence
<220> FEATURE:
<223> OTHER INFORMATION: synthetically generated oligonucleotide

<400> SEQUENCE: 47
tttattgaat tcattaaaga ggagaaatta actatgatct gtgtggaaat attcggaaag 60

<210> SEQ ID NO 48
<211> LENGTH: 40
<212> TYPE: DNA
<213> ORGANISM: Artificial sequence
<220> FEATURE:
<223> OTHER INFORMATION: primer sequence

<400> SEQUENCE: 48
gaagatgctt ctcccactct ctcttacttt cgaaatatct 40

<210> SEQ ID NO 49
<211> LENGTH: 54
<212> TYPE: DNA
<213> ORGANISM: Artificial sequence
<220> FEATURE:
<223> OTHER INFORMATION: synthetically generated oligonucleotide

<400> SEQUENCE: 49
tttattcaat tgattaaaga ggagaaatta actatgggga ttggtggcga cgac 54

<210> SEQ ID NO 50
<211> LENGTH: 36
<212> TYPE: DNA
<213> ORGANISM: Artificial sequence
<220> FEATURE:
<223> OTHER INFORMATION: synthetically generated oligonucleotide

<400> SEQUENCE: 50
cctccataca cttatacttt tctattcgaa ttattt 36

<210> SEQ ID NO 51
<211> LENGTH: 60
<212> TYPE: DNA
<213> ORGANISM: Artificial sequence
<220> FEATURE:
<223> OTHER INFORMATION: synthetically generated oligonucleotide -continued

<400> SEQUENCE: 51
tttattgaat tcattaaaga ggagaaatta actatgctac cagaagagtt cctatggggc 60

<210> SEQ ID NO 52
<211> LENGTH: 39
<212> TYPE: DNA
<213> ORGANISM: Artificial sequence
<220> FEATURE:
<223> OTHER INFORMATION: synthetically generated oligonucleotide

<400> SEQUENCE: 52
ctttacttct ggtatcggca actactcttc gaattattt 39

<210> SEQ ID NO 53
<211> LENGTH: 68
<212> TYPE: DNA
<213> ORGANISM: Artificial sequence
<220> FEATURE:
<223> OTHER INFORMATION: synthetically generated oligonucleotide

<400> SEQUENCE: 53
aaaaaacaat tgaattcatt aaagaggaga aattaactat ggtagaaaga cacttcagat 60
atgttctt 68

<210> SEQ ID NO 54
<211> LENGTH: 36
<212> TYPE: DNA
<213> ORGANISM: Artificial sequence
<220> FEATURE:
<223> OTHER INFORMATION: synthetically generated oligonucleotide

<400> SEQUENCE: 54
gtccgtttct catttacttc ttaacctagg cttttt 36

<210> SEQ ID NO 55
<211> LENGTH: 56
<212> TYPE: DNA
<213> ORGANISM: Artificial sequence
<220> FEATURE:
<223> OTHER INFORMATION: synthetically generated oligonucleotide

<400> SEQUENCE: 55
ttttggaatt cattaaagag gagaaattaa ctatggaact gatcatagaa ggttac 56

<210> SEQ ID NO 56
<211> LENGTH: 36
<212> TYPE: DNA
<213> ORGANISM: Artificial sequence
<220> FEATURE:
<223> OTHER INFORMATION: synthetically generated oligonucleotide

<400> SEQUENCE: 56
cgcatgcaag acatgtctct cacttttcga agaata 36

<210> SEQ ID NO 57
<211> LENGTH: 1992
<212> TYPE: DNA
<213> ORGANISM: Thermotoga maritima

<400> SEQUENCE: 57
cttttattga tcgttgagct ctctttcgtt ctctttgcaa gtgacgagtt cgtgaaagtg 60
gaaaacggaa aattcgctct gaacggaaaa gaattcagat tcattggaag caacaactac 120
tacatgcact acaagagcaa cggaatgata gacagtgttc tggagagtgc cagagacatg 180

-continued

```
ggtataaagg tcctcagaat ctggggtttc ctcgacgggg agagttactg cagagacaag    240
aacacctaca tgcatcctga gcccggtgtt ttcggggtgc cagaaggaat atcgaacgcc    300
cagagcggtt tcgaaagact cgactacaca gttgcgaaag cgaaagaact cggtataaaa    360
cttgtcattg ttcttgtgaa caactgggac gacttcggtg gaatgaacca gtacgtgagg    420
tggtttggag gaacccatca cgacgatttc tacagagatg agaagatcaa agaagagtac    480
aaaaagtacg tctcctttct cgtaaaccat gtcaatacct acacgggagt tccttacagg    540
gaagagccca ccatcatggc ctgggagctt gcaaacgaac cgcgctgtga gacggacaaa    600
tcggggaaca cgctcgttga gtgggtgaag gagatgagct cctacataaa gagtctggat    660
cccaaccacc tcgtggctgt gggggacgaa ggattcttca gcaactacga aggattcaaa    720
ccttacggtg gagaagccga gtgggcctac aacggctggt ccggtgttga ctggaagaag    780
ctcctttcga tagagacggt ggacttcggc acgttccacc tctatccgtc ccactggggt    840
gtcagtccag agaactatgc ccagtgggga gcgaagtgga tagaagacca cataaagatc    900
gcaaaagaga tcggaaaacc cgttgttctg gaagaatatg gaattccaaa gagtgcgcca    960
gttaacagaa cggccatcta cagactctgg aacgatctgg tctacgatct cggtggagat   1020
ggagcgatgt tctggatgct cgcgggaatc ggggaaggtt cggacagaga cgagagaggg   1080
tactatccgg actacgacgg tttcagaata gtgaacgacg acagtccaga agcggaactg   1140
ataagagaat acgcgaagct gttcaacaca ggtgaagaca taagagaaga cacctgctct   1200
ttcatccttc caaaagacgg catggagatc aaaaagaccg tggaagtgag ggctggtgtt   1260
ttcgactaca gcaacacgtt tgaaaagttg tctgtcaaag tcgaagatct ggtttttgaa   1320
aatgagatag agcatctcgg atacggaatt tacggctttg atctcgacac aacccggatc   1380
ccggatggag aacatgaaat gttccttgaa ggccactttc agggaaaaac ggtgaaagac   1440
tctatcaaag cgaaagtggt gaacgaagca cggtacgtgc tcgcagagga agttgatttt   1500
tcctctccag aagaggtgaa aaactggtgg aacagcggaa cctggcaggc agagttcggg   1560
tcacctgaca ttgaatggaa cggtgaggtg ggaaatggag cactgcagct gaacgtgaaa   1620
ctgcccggaa agagcgactg ggaagaagtg agagtagcaa ggaagttcga aagactctca   1680
gaatgtgaga tcctcgagta cgacatctac attccaaacg tcgagggact caagggaagg   1740
ttgaggccgt acgcggttct gaaccccggc tgggtgaaga taggcctcga catgaacaac   1800
gcgaacgtgg aaagtgcgga gatcatcact ttcggcggaa aagagtacag aagattccat   1860
gtaagaattg agttcgacag aacagcgggg gtgaaagaac ttcacatagg agttgtcggt   1920
gatcatctga ggtacgatgg accgattttc atcgataatg tgagacttta taaaagaaca   1980
ggaggtatgt ga                                                       1992
```

<210> SEQ ID NO 58
<211> LENGTH: 2055
<212> TYPE: DNA
<213> ORGANISM: Thermotoga maritima

<400> SEQUENCE: 58

```
atgaaaagaa tcgacctgaa tggtttctgg agcgttaggg ataacgaagg gagattttcg     60
tttgaaggga ctgtgccagg ggttgtccag gcagatctgg tcagaaaagg tcttcttcca    120
cacccgtacg ttgggatgaa cgaagatctc ttcaaggaaa tagaagacag agagtggatc    180
tacgagaggg agttcgagtt caaagaagat gtgaaagagg gggaacgtgt cgatctcgtt    240
```

-continued

```
tttgagggcg tcgacacgct gtcggatgtt tatctgaacg gtgtttacct tggaagcacc    300

gaagacatgt tcatcgagta tcgcttcgat gtcacgaacg tgttgaaaga aaagaatcac    360

ctgaaggtgt acataaaatc tcccatcaga gttccgaaaa ctctcgagca gaactacggg    420

gtcctcggcg gtcctgaaga tcccatcaga ggatacataa gaaaagccca gtattcgtac    480

ggatgggact ggggtgccag aatcgttaca agcggtattt ggaaacccgt ctacctcgag    540

gtgtacaggg cacgtcttca ggattcaacg gcttatctgt tggaacttga ggggaaagat    600

gcccttgtga gggtgaacgg tttcgtacac ggggaaggaa atctcattgt ggaagtttat    660

gtaaacggtg aaaagatagg ggagtttcct gttcttgaaa agaacggaga aaagctcttc    720

gatggagtgt tccacctgaa agatgtgaaa ctatggtatc cgtggaacgt ggggaaaccg    780

tacctgtacg atttcgtttt cgtgttgaaa gacttaaacg gagagatcta cagagaagaa    840

aagaaaatcg gtttgagaag agtcagaatc gttcaggagc ccgatgaaga aggaaaaact    900

ttcatattcg aaatcaacgg tgagaaagtc ttcgctaagg gtgctaactg gattccctca    960

gaaaacatcc tcacgtggtt gaaggaggaa gattacgaaa agctcgtcaa aatggcaagg   1020

agtgccaata tgaacatgct cagggtctgg ggaggaggaa tctacgagag agagatcttc   1080

tacagactct gtgatgaact cggtatcatg gtgtggcagg atttcatgta cgcgtgtctt   1140

gaatatccgg atcatcttcc gtggttcaga aaactcgcga acgaagaggc aagaaagatt   1200

gtgagaaaac tcagatacca tccctccatt gttctctggt gcggaaacaa cgaaaacaac   1260

tggggattcg atgaatgggg aaatatggcc agaaaagtgg atggtatcaa cctcggaaac   1320

aggctctacc tcttcgattt tcctgagatt tgtgccgaag aagacccgtc cactccctat   1380

tggccatcca gtccatacgg cggtgaaaaa gcgaacagcg aaaaggaagg agacaggcac   1440

gtctggtacg tgtggagtgg ctggatgaac tacgaaaact acgaaaaaga caccggaagg   1500

ttcatcagcg agtttggatt tcagggtgct ccccatccag agacgataga gttcttttca   1560

aaacccgagg aaagagagat attccatccc gtcatgctga agcacaacaa acaggtggaa   1620

ggacaggaaa gattgatcag gttcatattc ggaaattttg gaaagtgtaa agatttcgac   1680

agttttgtgt atctgtccca gctcaaccag gcggaggcga tcaagttcgg tgttgaacac   1740

tggcgaagca ggaagtacaa aacggccggc gctctcttct ggcagttcaa cgacagctgg   1800

ccggtcttca gctggtccgc agtcgattac ttcaaaaggc ccaaagctct ctactactat   1860

gcgagaagat tcttcgctga agttctaccc gttttgaaga agagagacaa caaaatagaa   1920

ctgctggtgg gtgagcgatc tgagggagac aaaagaagtc tctctcaggc ttgcagccta   1980

cgagaagaag ggagaaaagg tattcgaaaa gacttacaga acggtactcc cagcagacgg   2040

tgtgagtttg gttga                                                    2055
```

```
<210> SEQ ID NO 59
<211> LENGTH: 2870
<212> TYPE: DNA
<213> ORGANISM: Bankia gouldi

<400> SEQUENCE: 59

atgaaaaaaa atctactaat gtttaaaagg cttacgtatc tacctttgtt tttaatgctg     60

ctctcactaa gttcagtagc tcaatctcct gtagaaaaac atggccgttt acaagttgac    120

ggaaaccgca ttcttaatgc gtctggagaa attacgagct tagctggtaa cagcctcttt    180

tggagtaatg ctggagacac ctccgatttt tataatgcag aaactgttga ttttttagca    240

gaaaactgga atagctcact tattagaata gctatgggcg taaaagaaaa ttgggatggc    300
```

-continued

```
ggaaatggct atattgatag tccgcaggag caagaagcta aaattagaaa agttattgat    360
gcagctattg ctaacggcat atatgtaata atagactggc acactcacga agcagagtta    420
tacacagatg aggctgttga ctttttttacc agaatggcag acctatacgg agatactccc    480
aatgtaatgt atgaaattta taacgagcct atataccaaa gttggcctgt tattaagaat    540
tatgcagagc aagtaattgc tggtatacgt tctaaagacc cagataattt aataattgta    600
ggtactagca attattctca gcaagttgat gtagcatcag cagacccaat atctgatact    660
aatgtggcat atactttaca tttttatgca gcatttaacc cgcatgataa cttaagaaat    720
gtagcacaga cagcattaga taataatgtt gctttgtttg ttacagaatg gggtacaatt    780
ttaaataccg gacaaggaga accagacaaa gaaagcacta atacttggat ggcctttttg    840
aaagaaaaag gtataagtca cgctaattgg tctttgagtg acaaagcttt tcctgaaaca    900
gggtctgtag ttcaagcagg acaaggtgta tctggtttaa ttagcaataa acttacagcc    960
tctggtgaaa ttgtaaaaaa catcatccaa aactgggata cagagacctc tacaggacct   1020
aaaacaacac aatgtagtac tatagaatgt attagagctg caatggaaac agcacaagca   1080
ggagatgaaa ttataattgc ccctggaaac tacaattttc aagacaagat acaaggtgcc   1140
tttaaccgta gtgtttacct ttatggtagt gctaacggaa acagtacaaa ccctattata   1200
ttaagaggcg aaagcgctac aaaccctcct gttttctcag gattagatta taacaatggc   1260
tacctattaa gtattgaagg tgattattgg aatattaaag atatagagtt taaaactggg   1320
tctaaaggta ttgttcttga caattctaat ggtagtaaat taaaaaacct tgttgttcat   1380
gatattggag aagaagctat tcacttgcgt gatggatcta gcaataatag tatagatggt   1440
tgcactatat acaatacagg tagaactaaa cctggttttg gtgaaggttt atatgtaggc   1500
tcagataaag gacaacatga cacttatgaa agagcttgta acaataacac tattgaaaac   1560
tgtaccgttg gacccaatgt aacagcagaa ggcgtagatg ttaaggaagg tacaatgaac   1620
actattataa gaaattgcgt gttttctgca gaaggaattt caggagaaaa tagctcagat   1680
gcttttattg atttaaaagg agcctatggt tttgtataca gaaacacgtt taatgttgat   1740
ggttctgaag taataaatac tggagtagac tttttagata gaggtacagg atttaataca   1800
ggttttagaa atgcaatatt tgaaaataca tataaccttg gcagtagagc ttcagaaatt   1860
tcaactgctc gtaaaaaaca aggttctcct gaacaaactc acgtttggga taatattaga   1920
aaccctaatt ctgttgattt tccaataagt gatggtacag aaaatctagt aaataaattc   1980
tgcccagatt ggaatataga accatgtaat cctgtagacg aaaccaacca agcacctaca   2040
ataagcttcc tatctcctgt taacaatatt actttagttg aaggttataa tttacaagtt   2100
gaagttaatg ctactgatgc agatggaact attgataatg taaaacttta tatagataac   2160
aatttagtta ggcaaataaa ttctacttca tataaatggg gccattctga ttctccaaat   2220
acagatgaac ttaatggtct tacagaagga acttatacct taaaagcaat tgcaactgat   2280
aacgacgggg cttctacaga aacgcaattt acgttaactg taataacaga acaaagtccg   2340
tctgagaatt gtgactttaa tacaccttct tcaactggtt tagaagattt tgacattaaa   2400
aagttttcta acgtttttga gttaggatct ggcggaccat ctttaagtaa tttaaaaaca   2460
tttactatta attggaattc gcaatacaat gggttatatc aattttcaat aaacacaaac   2520
aacggtgtac ctgattatta tataaattta aaaccaaaaa ttacctttca gtttaaaaat   2580
gcaaatccag aaatatctat tagcaatagc ttaattccta attttgatgg tgattactgg   2640
```

-continued

```
gtaacatcag ataacggtaa ttttgtgatg gtatctaaaa ctaataattt tacgatatac   2700

tttagtaatg acgctactgc tcctatttgt aatgttacgc ctagtaacca aataagtaaa   2760

attactgatg attctagtat taattttaag ctttacccta atcctgcttt agacgaaact   2820

atttttgtga gcgctgaaga tgaaaaacta gctttggtgc ttgtaccagt              2870
```

<210> SEQ ID NO 60
<211> LENGTH: 960
<212> TYPE: DNA
<213> ORGANISM: Pyrococcus furiosus

<400> SEQUENCE: 60

```
atgagcaaga aaaagttcgt catcgtatct atcttaacaa tccttttagt acaggcaata     60

tattttgtag aaaagtatca tacctctgag gacaagtcaa cttcaaatac ctcatctaca    120

ccaccccaaa caacactttc cactaccaag gttctcaaga ttagataccc tgatgacggt    180

gagtggccag gagctcctat tgataaggat ggtgatggga acccagaatt ctacattgaa    240

ataaacctat ggaacattct taatgctact ggatttgctg agatgacgta caatttaacc    300

agcggcgtcc ttcactacgt ccaacaactt gacaacattg tcttgaggga tagaagtaat    360

tgggtgcatg gataccccga aatattctat ggaaacaagc catggaatgc aaactacgca    420

actgatggcc caataccatt acccagtaaa gtttcaaacc taacagactt ctatctaaca    480

atctcctata aacttgagcc caagaacggc ctgccaatta acttcgcaat agaatcctgg    540

ttaacgagag aagcttggag aacaacagga attaacagcg atgagcaaga agtaatgata    600

tggatttact atgacggatt acaaccggct ggctccaaag ttaaggagat tgtagtccca    660

ataatagtta acggaacacc agtaaatgct acatttgaag tatggaaggc aaacattggt    720

tgggagtatg ttgcatttag aataaagacc ccaatcaaag agggaacagt gacaattcca    780

tacggagcat ttataagtgt tgcagccaac atttcaagct taccaaatta cacagaactt    840

tacttagagg acgtggagat tggaactgag tttggaacgc caagcactac ctccgcccac    900

ctagagtggt ggatcacaaa cataacacta actcctctag atagacctct tatttcctaa    960
```

<210> SEQ ID NO 61
<211> LENGTH: 663
<212> TYPE: PRT
<213> ORGANISM: Thermotoga maritima

<400> SEQUENCE: 61

```
Leu Leu Leu Ile Val Glu Leu Ser Phe Val Leu Phe Ala Ser Asp Glu
 1               5                  10                  15

Phe Val Lys Val Glu Asn Gly Lys Phe Ala Leu Asn Gly Lys Glu Phe
            20                  25                  30

Arg Phe Ile Gly Ser Asn Asn Tyr Tyr Met His Tyr Lys Ser Asn Gly
        35                  40                  45

Met Ile Asp Ser Val Leu Glu Ser Ala Arg Asp Met Gly Ile Lys Val
    50                  55                  60

Leu Arg Ile Trp Gly Phe Leu Asp Gly Glu Ser Tyr Cys Arg Asp Lys
65                  70                  75                  80

Asn Thr Tyr Met His Pro Glu Pro Gly Val Phe Gly Val Pro Glu Gly
                85                  90                  95

Ile Ser Asn Ala Gln Ser Gly Phe Glu Arg Leu Asp Tyr Thr Val Ala
            100                 105                 110

Lys Ala Lys Glu Leu Gly Ile Lys Leu Val Ile Val Leu Val Asn Asn
        115                 120                 125
```

```
Trp Asp Asp Phe Gly Gly Met Asn Gln Tyr Val Arg Trp Phe Gly Gly
    130                 135                 140

Thr His His Asp Asp Phe Tyr Arg Asp Glu Lys Ile Lys Glu Glu Tyr
145                 150                 155                 160

Lys Lys Tyr Val Ser Phe Leu Val Asn His Val Asn Thr Tyr Thr Gly
                165                 170                 175

Val Pro Tyr Arg Glu Glu Pro Thr Ile Met Ala Trp Glu Leu Ala Asn
            180                 185                 190

Glu Pro Arg Cys Glu Thr Asp Lys Ser Gly Asn Thr Leu Val Glu Trp
        195                 200                 205

Val Lys Glu Met Ser Ser Tyr Ile Lys Ser Leu Asp Pro Asn His Leu
    210                 215                 220

Val Ala Val Gly Asp Glu Gly Phe Phe Ser Asn Tyr Glu Gly Phe Lys
225                 230                 235                 240

Pro Tyr Gly Gly Glu Ala Glu Trp Ala Tyr Asn Gly Trp Ser Gly Val
                245                 250                 255

Asp Trp Lys Lys Leu Leu Ser Ile Glu Thr Val Asp Phe Gly Thr Phe
            260                 265                 270

His Leu Tyr Pro Ser His Trp Gly Val Ser Pro Glu Asn Tyr Ala Gln
        275                 280                 285

Trp Gly Ala Lys Trp Ile Glu Asp His Ile Lys Ile Ala Lys Glu Ile
    290                 295                 300

Gly Lys Pro Val Val Leu Glu Glu Tyr Gly Ile Pro Lys Ser Ala Pro
305                 310                 315                 320

Val Asn Arg Thr Ala Ile Tyr Arg Leu Trp Asn Asp Leu Val Tyr Asp
                325                 330                 335

Leu Gly Gly Asp Gly Ala Met Phe Trp Met Leu Ala Gly Ile Gly Glu
            340                 345                 350

Gly Ser Asp Arg Asp Glu Arg Gly Tyr Tyr Pro Asp Tyr Asp Gly Phe
        355                 360                 365

Arg Ile Val Asn Asp Asp Ser Pro Glu Ala Glu Leu Ile Arg Glu Tyr
    370                 375                 380

Ala Lys Leu Phe Asn Thr Gly Glu Asp Ile Arg Glu Asp Thr Cys Ser
385                 390                 395                 400

Phe Ile Leu Pro Lys Asp Gly Met Glu Ile Lys Lys Thr Val Glu Val
                405                 410                 415

Arg Ala Gly Val Phe Asp Tyr Ser Asn Thr Phe Glu Lys Leu Ser Val
            420                 425                 430

Lys Val Glu Asp Leu Val Phe Glu Asn Glu Ile Glu His Leu Gly Tyr
        435                 440                 445

Gly Ile Tyr Gly Phe Asp Leu Asp Thr Thr Arg Ile Pro Asp Gly Glu
    450                 455                 460

His Glu Met Phe Leu Glu Gly His Phe Gln Gly Lys Thr Val Lys Asp
465                 470                 475                 480

Ser Ile Lys Ala Lys Val Val Asn Glu Ala Arg Tyr Val Leu Ala Glu
                485                 490                 495

Glu Val Asp Phe Ser Ser Pro Glu Glu Val Lys Asn Trp Trp Asn Ser
            500                 505                 510

Gly Thr Trp Gln Ala Glu Phe Gly Ser Pro Asp Ile Glu Trp Asn Gly
        515                 520                 525

Glu Val Gly Asn Gly Ala Leu Gln Leu Asn Val Lys Leu Pro Gly Lys
    530                 535                 540
```

```
Ser Asp Trp Glu Glu Val Arg Val Ala Arg Lys Phe Glu Arg Leu Ser
545                 550                 555                 560

Glu Cys Glu Ile Leu Glu Tyr Asp Ile Tyr Ile Pro Asn Val Glu Gly
                565                 570                 575

Leu Lys Gly Arg Leu Arg Pro Tyr Ala Val Leu Asn Pro Gly Trp Val
            580                 585                 590

Lys Ile Gly Leu Asp Met Asn Asn Ala Asn Val Glu Ser Ala Glu Ile
        595                 600                 605

Ile Thr Phe Gly Gly Lys Glu Tyr Arg Arg Phe His Val Arg Ile Glu
    610                 615                 620

Phe Asp Arg Thr Ala Gly Val Lys Glu Leu His Ile Gly Val Val Gly
625                 630                 635                 640

Asp His Leu Arg Tyr Asp Gly Pro Ile Phe Ile Asp Asn Val Arg Leu
                645                 650                 655

Tyr Lys Arg Thr Gly Gly Met
            660


<210> SEQ ID NO 62
<211> LENGTH: 684
<212> TYPE: PRT
<213> ORGANISM: Thermotoga maritima

<400> SEQUENCE: 62

Met Lys Arg Ile Asp Leu Asn Gly Phe Trp Ser Val Arg Asp Asn Glu
 1               5                  10                  15

Gly Arg Phe Ser Phe Glu Gly Thr Val Pro Gly Val Val Gln Ala Asp
            20                  25                  30

Leu Val Arg Lys Gly Leu Leu Pro His Pro Tyr Val Gly Met Asn Glu
        35                  40                  45

Asp Leu Phe Lys Glu Ile Glu Asp Arg Glu Trp Ile Tyr Glu Arg Glu
    50                  55                  60

Phe Glu Phe Lys Glu Asp Val Lys Glu Gly Glu Arg Val Asp Leu Val
65                  70                  75                  80

Phe Glu Gly Val Asp Thr Leu Ser Asp Val Tyr Leu Asn Gly Val Tyr
                85                  90                  95

Leu Gly Ser Thr Glu Asp Met Phe Ile Glu Tyr Arg Phe Asp Val Thr
            100                 105                 110

Asn Val Leu Lys Glu Lys Asn His Leu Lys Val Tyr Ile Lys Ser Pro
        115                 120                 125

Ile Arg Val Pro Lys Thr Leu Glu Gln Asn Tyr Gly Val Leu Gly Gly
    130                 135                 140

Pro Glu Asp Pro Ile Arg Gly Tyr Ile Arg Lys Ala Gln Tyr Ser Tyr
145                 150                 155                 160

Gly Trp Asp Trp Gly Ala Arg Ile Val Thr Ser Gly Ile Trp Lys Pro
                165                 170                 175

Val Tyr Leu Glu Val Tyr Arg Ala Arg Leu Gln Asp Ser Thr Ala Tyr
            180                 185                 190

Leu Leu Glu Leu Glu Gly Lys Asp Ala Leu Val Arg Val Asn Gly Phe
        195                 200                 205

Val His Gly Glu Gly Asn Leu Ile Val Glu Val Tyr Val Asn Gly Glu
    210                 215                 220

Lys Ile Gly Glu Phe Pro Val Leu Glu Lys Asn Gly Glu Lys Leu Phe
225                 230                 235                 240

Asp Gly Val Phe His Leu Lys Asp Val Lys Leu Trp Tyr Pro Trp Asn
                245                 250                 255
```

```
Val Gly Lys Pro Tyr Leu Tyr Asp Phe Val Phe Val Leu Lys Asp Leu
            260                 265                 270

Asn Gly Glu Ile Tyr Arg Glu Glu Lys Lys Ile Gly Leu Arg Arg Val
        275                 280                 285

Arg Ile Val Gln Glu Pro Asp Glu Glu Gly Lys Thr Phe Ile Phe Glu
    290                 295                 300

Ile Asn Gly Glu Lys Val Phe Ala Lys Gly Ala Asn Trp Ile Pro Ser
305                 310                 315                 320

Glu Asn Ile Leu Thr Trp Leu Lys Glu Glu Asp Tyr Glu Lys Leu Val
                325                 330                 335

Lys Met Ala Arg Ser Ala Asn Met Asn Met Leu Arg Val Trp Gly Gly
            340                 345                 350

Gly Ile Tyr Glu Arg Glu Ile Phe Tyr Arg Leu Cys Asp Glu Leu Gly
        355                 360                 365

Ile Met Val Trp Gln Asp Phe Met Tyr Ala Cys Leu Glu Tyr Pro Asp
    370                 375                 380

His Leu Pro Trp Phe Arg Lys Leu Ala Asn Glu Glu Ala Arg Lys Ile
385                 390                 395                 400

Val Arg Lys Leu Arg Tyr His Pro Ser Ile Val Leu Trp Cys Gly Asn
                405                 410                 415

Asn Glu Asn Asn Trp Gly Phe Asp Glu Trp Gly Asn Met Ala Arg Lys
            420                 425                 430

Val Asp Gly Ile Asn Leu Gly Asn Arg Leu Tyr Leu Phe Asp Phe Pro
        435                 440                 445

Glu Ile Cys Ala Glu Glu Asp Pro Ser Thr Pro Tyr Trp Pro Ser Ser
    450                 455                 460

Pro Tyr Gly Gly Glu Lys Ala Asn Ser Glu Lys Glu Gly Asp Arg His
465                 470                 475                 480

Val Trp Tyr Val Trp Ser Gly Trp Met Asn Tyr Glu Asn Tyr Glu Lys
                485                 490                 495

Asp Thr Gly Arg Phe Ile Ser Glu Phe Gly Phe Gln Gly Ala Pro His
            500                 505                 510

Pro Glu Thr Ile Glu Phe Phe Ser Lys Pro Glu Glu Arg Glu Ile Phe
        515                 520                 525

His Pro Val Met Leu Lys His Asn Lys Gln Val Glu Gly Gln Glu Arg
    530                 535                 540

Leu Ile Arg Phe Ile Phe Gly Asn Phe Gly Lys Cys Lys Asp Phe Asp
545                 550                 555                 560

Ser Phe Val Tyr Leu Ser Gln Leu Asn Gln Ala Glu Ala Ile Lys Phe
                565                 570                 575

Gly Val Glu His Trp Arg Ser Arg Lys Tyr Lys Thr Ala Gly Ala Leu
            580                 585                 590

Phe Trp Gln Phe Asn Asp Ser Trp Pro Val Phe Ser Trp Ser Ala Val
        595                 600                 605

Asp Tyr Phe Lys Arg Pro Lys Ala Leu Tyr Tyr Tyr Ala Arg Arg Phe
    610                 615                 620

Phe Ala Glu Val Leu Pro Val Leu Lys Lys Arg Asp Asn Lys Ile Glu
625                 630                 635                 640

Leu Leu Val Gly Glu Arg Ser Glu Gly Asp Lys Arg Ser Leu Ser Gln
                645                 650                 655

Ala Cys Ser Leu Arg Glu Glu Gly Arg Lys Gly Ile Arg Lys Asp Leu
            660                 665                 670
```

```
Gln Asn Gly Thr Pro Ser Arg Arg Cys Glu Phe Gly
        675                 680


<210> SEQ ID NO 63
<211> LENGTH: 956
<212> TYPE: PRT
<213> ORGANISM: Bankia gouldi

<400> SEQUENCE: 63

Met Lys Lys Asn Leu Leu Met Phe Lys Arg Leu Thr Tyr Leu Pro Leu
 1               5                  10                  15

Phe Leu Met Leu Leu Ser Leu Ser Ser Val Ala Gln Ser Pro Val Glu
            20                  25                  30

Lys His Gly Arg Leu Gln Val Asp Gly Asn Arg Ile Leu Asn Ala Ser
        35                  40                  45

Gly Glu Ile Thr Ser Leu Ala Gly Asn Ser Leu Phe Trp Ser Asn Ala
    50                  55                  60

Gly Asp Thr Ser Asp Phe Tyr Asn Ala Glu Thr Val Asp Phe Leu Ala
65                  70                  75                  80

Glu Asn Trp Asn Ser Ser Leu Ile Arg Ile Ala Met Gly Val Lys Glu
                85                  90                  95

Asn Trp Asp Gly Gly Asn Gly Tyr Ile Asp Ser Pro Gln Glu Gln Glu
            100                 105                 110

Ala Lys Ile Arg Lys Val Ile Asp Ala Ala Ile Ala Asn Gly Ile Tyr
        115                 120                 125

Val Ile Ile Asp Trp His Thr His Glu Ala Glu Leu Tyr Thr Asp Glu
    130                 135                 140

Ala Val Asp Phe Phe Thr Arg Met Ala Asp Leu Tyr Gly Asp Thr Pro
145                 150                 155                 160

Asn Val Met Tyr Glu Ile Tyr Asn Glu Pro Ile Tyr Gln Ser Trp Pro
                165                 170                 175

Val Ile Lys Asn Tyr Ala Glu Gln Val Ile Ala Gly Ile Arg Ser Lys
            180                 185                 190

Asp Pro Asp Asn Leu Ile Ile Val Gly Thr Ser Asn Tyr Ser Gln Gln
        195                 200                 205

Val Asp Val Ala Ser Ala Asp Pro Ile Ser Asp Thr Asn Val Ala Tyr
    210                 215                 220

Thr Leu His Phe Tyr Ala Ala Phe Asn Pro His Asp Asn Leu Arg Asn
225                 230                 235                 240

Val Ala Gln Thr Ala Leu Asp Asn Asn Val Ala Leu Phe Val Thr Glu
                245                 250                 255

Trp Gly Thr Ile Leu Asn Thr Gly Gln Gly Glu Pro Asp Lys Glu Ser
            260                 265                 270

Thr Asn Thr Trp Met Ala Phe Leu Lys Glu Lys Gly Ile Ser His Ala
        275                 280                 285

Asn Trp Ser Leu Ser Asp Lys Ala Phe Pro Glu Thr Gly Ser Val Val
    290                 295                 300

Gln Ala Gly Gln Gly Val Ser Gly Leu Ile Ser Asn Lys Leu Thr Ala
305                 310                 315                 320

Ser Gly Glu Ile Val Lys Asn Ile Ile Gln Asn Trp Asp Thr Glu Thr
                325                 330                 335

Ser Thr Gly Pro Lys Thr Thr Gln Cys Ser Thr Ile Glu Cys Ile Arg
            340                 345                 350

Ala Ala Met Glu Thr Ala Gln Ala Gly Asp Glu Ile Ile Ile Ala Pro
        355                 360                 365
```

-continued

```
Gly Asn Tyr Asn Phe Gln Asp Lys Ile Gln Gly Ala Phe Asn Arg Ser
    370                 375                 380

Val Tyr Leu Tyr Gly Ser Ala Asn Gly Asn Ser Thr Asn Pro Ile Ile
385                 390                 395                 400

Leu Arg Gly Glu Ser Ala Thr Asn Pro Pro Val Phe Ser Gly Leu Asp
                405                 410                 415

Tyr Asn Asn Gly Tyr Leu Leu Ser Ile Glu Gly Asp Tyr Trp Asn Ile
            420                 425                 430

Lys Asp Ile Glu Phe Lys Thr Gly Ser Lys Gly Ile Val Leu Asp Asn
        435                 440                 445

Ser Asn Gly Ser Lys Leu Lys Asn Leu Val Val His Asp Ile Gly Glu
    450                 455                 460

Glu Ala Ile His Leu Arg Asp Gly Ser Ser Asn Asn Ser Ile Asp Gly
465                 470                 475                 480

Cys Thr Ile Tyr Asn Thr Gly Arg Thr Lys Pro Gly Phe Gly Glu Gly
                485                 490                 495

Leu Tyr Val Gly Ser Asp Lys Gly Gln His Asp Thr Tyr Glu Arg Ala
            500                 505                 510

Cys Asn Asn Asn Thr Ile Glu Asn Cys Thr Val Gly Pro Asn Val Thr
        515                 520                 525

Ala Glu Gly Val Asp Val Lys Glu Gly Thr Met Asn Thr Ile Ile Arg
    530                 535                 540

Asn Cys Val Phe Ser Ala Glu Gly Ile Ser Gly Glu Asn Ser Ser Asp
545                 550                 555                 560

Ala Phe Ile Asp Leu Lys Gly Ala Tyr Gly Phe Val Tyr Arg Asn Thr
                565                 570                 575

Phe Asn Val Asp Gly Ser Glu Val Ile Asn Thr Gly Val Asp Phe Leu
            580                 585                 590

Asp Arg Gly Thr Gly Phe Asn Thr Gly Phe Arg Asn Ala Ile Phe Glu
        595                 600                 605

Asn Thr Tyr Asn Leu Gly Ser Arg Ala Ser Glu Ile Ser Thr Ala Arg
    610                 615                 620

Lys Lys Gln Gly Ser Pro Glu Gln Thr His Val Trp Asp Asn Ile Arg
625                 630                 635                 640

Asn Pro Asn Ser Val Asp Phe Pro Ile Ser Asp Gly Thr Glu Asn Leu
                645                 650                 655

Val Asn Lys Phe Cys Pro Asp Trp Asn Ile Glu Pro Cys Asn Pro Val
            660                 665                 670

Asp Glu Thr Asn Gln Ala Pro Thr Ile Ser Phe Leu Ser Pro Val Asn
        675                 680                 685

Asn Ile Thr Leu Val Glu Gly Tyr Asn Leu Gln Val Glu Val Asn Ala
    690                 695                 700

Thr Asp Ala Asp Gly Thr Ile Asp Asn Val Lys Leu Tyr Ile Asp Asn
705                 710                 715                 720

Asn Leu Val Arg Gln Ile Asn Ser Thr Ser Tyr Lys Trp Gly His Ser
                725                 730                 735

Asp Ser Pro Asn Thr Asp Glu Leu Asn Gly Leu Thr Glu Gly Thr Tyr
            740                 745                 750

Thr Leu Lys Ala Ile Ala Thr Asp Asn Asp Gly Ala Ser Thr Glu Thr
        755                 760                 765

Gln Phe Thr Leu Thr Val Ile Thr Glu Gln Ser Pro Ser Glu Asn Cys
    770                 775                 780
```

-continued

```
Asp Phe Asn Thr Pro Ser Ser Thr Gly Leu Glu Asp Phe Asp Ile Lys
785                 790                 795                 800

Lys Phe Ser Asn Val Phe Glu Leu Gly Ser Gly Gly Pro Ser Leu Ser
                805                 810                 815

Asn Leu Lys Thr Phe Thr Ile Asn Trp Asn Ser Gln Tyr Asn Gly Leu
            820                 825                 830

Tyr Gln Phe Ser Ile Asn Thr Asn Asn Gly Val Pro Asp Tyr Tyr Ile
        835                 840                 845

Asn Leu Lys Pro Lys Ile Thr Phe Gln Phe Lys Asn Ala Asn Pro Glu
    850                 855                 860

Ile Ser Ile Ser Asn Ser Leu Ile Pro Asn Phe Asp Gly Asp Tyr Trp
865                 870                 875                 880

Val Thr Ser Asp Asn Gly Asn Phe Val Met Val Ser Lys Thr Asn Asn
                885                 890                 895

Phe Thr Ile Tyr Phe Ser Asn Asp Ala Thr Ala Pro Ile Cys Asn Val
            900                 905                 910

Thr Pro Ser Asn Gln Ile Ser Lys Ile Thr Asp Asp Ser Ser Ile Asn
        915                 920                 925

Phe Lys Leu Tyr Pro Asn Pro Ala Leu Asp Glu Thr Ile Phe Val Ser
    930                 935                 940

Ala Glu Asp Glu Lys Leu Ala Leu Val Leu Val Pro
945                 950                 955


<210> SEQ ID NO 64
<211> LENGTH: 319
<212> TYPE: PRT
<213> ORGANISM: Pyrococcus furiosus

<400> SEQUENCE: 64

Met Ser Lys Lys Lys Phe Val Ile Val Ser Ile Leu Thr Ile Leu Leu
 1               5                  10                  15

Val Gln Ala Ile Tyr Phe Val Glu Lys Tyr His Thr Ser Glu Asp Lys
            20                  25                  30

Ser Thr Ser Asn Thr Ser Ser Thr Pro Pro Gln Thr Thr Leu Ser Thr
        35                  40                  45

Thr Lys Val Leu Lys Ile Arg Tyr Pro Asp Asp Gly Glu Trp Pro Gly
    50                  55                  60

Ala Pro Ile Asp Lys Asp Gly Asp Gly Asn Pro Glu Phe Tyr Ile Glu
65                  70                  75                  80

Ile Asn Leu Trp Asn Ile Leu Asn Ala Thr Gly Phe Ala Glu Met Thr
                85                  90                  95

Tyr Asn Leu Thr Ser Gly Val Leu His Tyr Val Gln Gln Leu Asp Asn
            100                 105                 110

Ile Val Leu Arg Asp Arg Ser Asn Trp Val His Gly Tyr Pro Glu Ile
        115                 120                 125

Phe Tyr Gly Asn Lys Pro Trp Asn Ala Asn Tyr Ala Thr Asp Gly Pro
    130                 135                 140

Ile Pro Leu Pro Ser Lys Val Ser Asn Leu Thr Asp Phe Tyr Leu Thr
145                 150                 155                 160

Ile Ser Tyr Lys Leu Glu Pro Lys Asn Gly Leu Pro Ile Asn Phe Ala
                165                 170                 175

Ile Glu Ser Trp Leu Thr Arg Glu Ala Trp Arg Thr Thr Gly Ile Asn
            180                 185                 190

Ser Asp Glu Gln Glu Val Met Ile Trp Ile Tyr Tyr Asp Gly Leu Gln
        195                 200                 205
```

```
Pro Ala Gly Ser Lys Val Lys Glu Ile Val Val Pro Ile Ile Val Asn
    210                 215                 220

Gly Thr Pro Val Asn Ala Thr Phe Glu Val Trp Lys Ala Asn Ile Gly
225                 230                 235                 240

Trp Glu Tyr Val Ala Phe Arg Ile Lys Thr Pro Ile Lys Glu Gly Thr
                245                 250                 255

Val Thr Ile Pro Tyr Gly Ala Phe Ile Ser Val Ala Ala Asn Ile Ser
            260                 265                 270

Ser Leu Pro Asn Tyr Thr Glu Leu Tyr Leu Glu Asp Val Glu Ile Gly
        275                 280                 285

Thr Glu Phe Gly Thr Pro Ser Thr Thr Ser Ala His Leu Glu Trp Trp
    290                 295                 300

Ile Thr Asn Ile Thr Leu Thr Pro Leu Asp Arg Pro Leu Ile Ser
305                 310                 315


<210> SEQ ID NO 65
<211> LENGTH: 52
<212> TYPE: DNA
<213> ORGANISM: Artificial Sequence
<220> FEATURE:
<223> OTHER INFORMATION: synthetically generated oligonucleotide

<400> SEQUENCE: 65

ccgacaattg attaaagagg agaaattaac tatggaaagg atcgatgaaa tt             52


<210> SEQ ID NO 66
<211> LENGTH: 31
<212> TYPE: DNA
<213> ORGANISM: Artificial Sequence
<220> FEATURE:
<223> OTHER INFORMATION: synthetically generated oligonucleotide

<400> SEQUENCE: 66

ctcttctcta agtttggtac tccatggagg c                                    31


<210> SEQ ID NO 67
<211> LENGTH: 52
<212> TYPE: DNA
<213> ORGANISM: Artificial Sequence
<220> FEATURE:
<223> OTHER INFORMATION: synthetically generated oligonucleotide

<400> SEQUENCE: 67

ccgacaattg attaaagagg agaaattaac tatgttccct gaaaagttcc tt             52


<210> SEQ ID NO 68
<211> LENGTH: 31
<212> TYPE: DNA
<213> ORGANISM: Artificial Sequence
<220> FEATURE:
<223> OTHER INFORMATION: synthetically generated oligonucleotide

<400> SEQUENCE: 68

ctccttaacg actcccctac tccatggagg c                                    31


<210> SEQ ID NO 69
<211> LENGTH: 27
<212> TYPE: DNA
<213> ORGANISM: Artificial Sequence
<220> FEATURE:
<223> OTHER INFORMATION: synthetically generated oligonucleotide

<400> SEQUENCE: 69
```

-continued

```
aataaggatc cgtttagcga cgctcgc                                    27


<210> SEQ ID NO 70
<211> LENGTH: 35
<212> TYPE: DNA
<213> ORGANISM: Artificial Sequence
<220> FEATURE:
<223> OTHER INFORMATION: synthetically generated oligonucleotide

<400> SEQUENCE: 70

cggataatgg cgacatgttg ggccttcgaa aataa                           35


<210> SEQ ID NO 71
<211> LENGTH: 52
<212> TYPE: DNA
<213> ORGANISM: Artificial Sequence
<220> FEATURE:
<223> OTHER INFORMATION: synthetically generated oligonucleotide

<400> SEQUENCE: 71

aataacaatt gaaggaggaa tttaaatggc ttatcatacc tctgaggaca ag        52


<210> SEQ ID NO 72
<211> LENGTH: 32
<212> TYPE: DNA
<213> ORGANISM: Artificial Sequence
<220> FEATURE:
<223> OTHER INFORMATION: synthetically generated oligonucleotide

<400> SEQUENCE: 72

ctatctggag aataaaggat tcagctgaat aa                              32
```